(12) United States Patent
Soderberg et al.

(10) Patent No.: US 9,138,030 B2
(45) Date of Patent: Sep. 22, 2015

(54) REEL BASED LACING SYSTEM

(71) Applicant: Boa Technology Inc., Denver, CO (US)

(72) Inventors: Mark S. Soderberg, Conifer, CO (US); Michael Joseph Nickel, Golden, CO (US); Sean Cavanagh, Golden, CO (US); James Paul Goodman, Fort Collins, CO (US)

(73) Assignee: Boa Technology Inc., Denver, CO (US)

( * ) Notice: Subject to any disclaimer, the term of this patent is extended or adjusted under 35 U.S.C. 154(b) by 0 days.

(21) Appl. No.: 14/472,055

(22) Filed: Aug. 28, 2014

(65) Prior Publication Data

US 2015/0101160 A1   Apr. 16, 2015

Related U.S. Application Data

(60) Continuation of application No. 13/924,426, filed on Jun. 21, 2013, which is a division of application No. 12/623,362, filed on Nov. 20, 2009, now Pat. No. 8,468,657.

(60) Provisional application No. 61/116,905, filed on Nov. 21, 2008.

(51) Int. Cl.
| | |
|---|---|
| *A43C 11/20* | (2006.01) |
| *A43C 11/00* | (2006.01) |
| *B65H 75/00* | (2006.01) |
| *A43C 11/16* | (2006.01) |

(Continued)

(52) U.S. Cl.
CPC .............. *A43C 11/165* (2013.01); *A43C 11/16* (2013.01); *A45C 13/10* (2013.01); *A61F 5/0118* (2013.01); *A63C 10/06* (2013.01); *B65H 75/30* (2013.01); *B65H 75/4434* (2013.01); *A41F 1/06* (2013.01); *A41F 9/025* (2013.01); *A45F 3/00* (2013.01); *A45F 3/04* (2013.01); *A45F 3/16* (2013.01);

(Continued)

(58) Field of Classification Search
USPC ........... 24/68 SK, 712.6, 712.9, 714.8, 714.3, 24/709.2; 36/50.1, 50.5; 242/388.3, 393, 242/395, 396.3, 397.2
See application file for complete search history.

(56) References Cited

U.S. PATENT DOCUMENTS

| 8,231,074 B2 * | 7/2012 | Hu et al. .................... 242/388.1 |
| 2006/0156517 A1 * | 7/2006 | Hammerslag et al. ...... 24/68 SK |

FOREIGN PATENT DOCUMENTS

| DE | 19945045 | 3/1994 |
| EP | 0651954 | 10/2006 |

(Continued)

OTHER PUBLICATIONS

European Search Report mailed on Oct. 10, 2014 for application EP 14168875, 20 pages.

*Primary Examiner* — Jack W Lavinder
(74) *Attorney, Agent, or Firm* — Kilpatrick Townsend & Stockton LLP

(57) ABSTRACT

A lacing system configured to selectively adjust the size of an opening on an object and allow for the incremental release of the lace within the lacing system. The lacing system can have a reel comprising a housing, a spool supported by the housing, and a knob supported by the housing. The reel can be configured so that cable is gathered in the channel formed in the spool when the spool is rotated in a first direction relative to the housing, and so that cable can be incrementally released from the spool when the spool is rotated in a second direction relative to the housing. In some embodiments, the reel can include a rotation limiter which can be configured to prevent over-tightening of the lacing system and/or to prevent rotation past the substantially fully loosened state.

19 Claims, 41 Drawing Sheets

(51) Int. Cl.
*A45C 13/10* (2006.01)
*A61F 5/01* (2006.01)
*A63C 10/06* (2012.01)
*B65H 75/44* (2006.01)
*B65H 75/30* (2006.01)
*A41F 1/06* (2006.01)
*A41F 9/02* (2006.01)
*A45F 3/00* (2006.01)
*A45F 3/04* (2006.01)
*A45F 3/16* (2006.01)

(52) U.S. Cl.
CPC .............. *Y10T 24/21* (2015.01); *Y10T 24/2183* (2015.01); *Y10T 24/37* (2015.01)

(56) References Cited

FOREIGN PATENT DOCUMENTS

| | | |
|---|---|---|
| IT | 01220811 | 6/1990 |
| WO | 01/15559 | 3/2001 |

\* cited by examiner

REEL BASED LACING SYSTEM

CROSS-REFERENCE TO RELATED APPLICATIONS

This application is a continuation of Ser. No. 13/924,426, filed Jun. 21, 2013, and titled REEL BASED LACING SYSTEM, which is a divisional of Ser. No. 12/623,362, filed on Nov. 20, 2009, and titled REEL BASED LACING SYSTEM, which claims the benefit under 35 U.S.C. §119(e) of U.S. Provisional Patent Application No. 61/116,905, filed on Nov. 21, 2008, and titled REEL BASED LACING SYSTEM. The entire contents of each of the above-listed references are hereby incorporated herein by reference.

INCORPORATION

Additionally, this application hereby incorporates by reference the entirety of the following documents: U.S. patent application Ser. No. 11/263,253, filed on Oct. 31, 2005 and published as U.S. Application Publication No. 2006/0156517 and U.S. patent application Ser. No. 11/650,665, filed Jan. 8, 2007 and published as U.S. Application Publication No. 2007/0169378.

BACKGROUND OF THE INVENTION

1. Field of the Invention

Embodiments of the present invention relate to lacing or closure systems and their related components used alone or in combination in any of a variety of articles including closeable bags, footwear, protective gear, or other wear.

2. Description of the Related Art

There currently exist a number of mechanisms and methods for tightening articles. Nevertheless, there remains a need for improved devices and methods.

SUMMARY OF THE INVENTION

Some embodiments provide a footwear lacing system. Although many of the lacing systems described herein are described in the context of footwear, one of ordinary skill in the art will recognize that any of the lacing systems described herein can be used in a wide range of articles without undue examination or modification. As such, any of the embodiments of the lacing systems disclosed herein are intended to be used in any of a wide range articles such as, but not limited to, footwear, hats or other headwear, belts, gloves, helmets, backpacks or other packs, luggage or other bags, bindings for snowboarding, water skiing, or other similar objects, wrist guards, and other similar or suitable articles.

In some embodiments, the system can be configured for use with a footwear member including first and second opposing sides configured to fit around a foot. The opening can be arranged along the midline of the foot or can be offset to the side of the midline. A plurality of lace guide members can be positioned on the opposing sides of the footwear member. One or more laces (also referred to herein as cable or cables) can be guided by the guide members, the lace being connected to one or more spools that can be rotatable in a winding direction and incrementally rotatable in an unwinding direction, allowing for the incremental release of lace from the spool.

In some embodiments, one or more embodiments of the spools disclosed herein can be used in conjunction with other suitable or traditional lace tightening systems, which may or may not have incremental release characteristics. For example, in some embodiments, one or more embodiments of the spools disclosed herein can be used in conjunction with any of the tightening systems disclosed in U.S. Application Publication No. 2006-0156517, which is incorporated by reference as if fully set forth herein.

In some embodiments, the lace can be slideably positioned around the guide members to provide a dynamic fit in response to movement of the foot within the footwear. The guide members can have a substantially C-shaped cross-section.

In some embodiments, the lacing system can have a spool supported within a cavity or opening formed in a housing, and a knob directly or indirectly supported by the housing. The spool can be configured to receive one or both ends of a cable routed through the lacing system. In some embodiments, one end of the cable can be attached to the housing. The spool can be configured to rotate in a first, winding direction relative to the housing in response to a user winding the knob in the first direction relative to the housing. Additionally, the spool can be configured to rotate in a second, unwinding direction relative to the housing in response to a user winding the knob in the second direction relative to the housing.

In some embodiments, the lace or cable in a tightened or partially tightened lacing system can result in a rotational force being exerted on the spool in the second, unwinding direction. The lacing system can be configured so that lace can be selectively incrementally released from the spool in the second, unwinding direction as a user actuates the incremental release of the spool. In some embodiments, the incremental release of the lace can be indicated by an audible noise or other discernable physical click.

In some embodiments, a user can actuate the incremental release of the spool by rotating the knob in the second, unwinding direction relative to the housing, causing arms projecting from the spool to become disengaged with their respective depression that each of the arms is engaged with, permitting the spool to rotate until the arms become engaged with the next successive depression formed in the housing. The arms can be caused to be disengaged by deflecting the ends of the arms away from the depressions. The user can continue to actuate the incremental release of the spool by continuing to rotate the knob in the second, unwinding direction relative to the housing.

In some embodiments, the spool can be fully released relative to the housing (i.e., the spool can be unlocked relative to the housing so as to be freely rotatable in the second, unwinding direction) so that the spool can freely release lace. In some embodiments, the release can be facilitated by moving the spool away from the housing so that the arms projecting from the spool are no longer engaged with the respective depressions formed in the housing. Once the desired amount of cable is released from the spool, the spool can be moved back toward the housing so that the arms projecting from the spool are again engaged with respective depressions formed in the housing, so that the spool can again be in the locked position relative to the housing so as to prevent the free rotation of the spool in the second, unwinding direction.

In some embodiments, a lacing system is provided for footwear having an upper with a lateral side and a medial side, the lacing system comprising at least a first lace guide attached to the lateral side of the upper, at least a second lace guide attached to the medial side of the upper, and each of the first and second lace guides comprising a lace pathway, a lace slideably extending along the lace pathway of each of the first and second lace guides. Additionally, a tightening reel of the footwear for retracting the lace and thereby advancing the first lace guide towards the second lace guide to tighten the footwear can be positioned on the footwear, and a lock can be moveable between a coupled position and an uncoupled position wherein the lock allows the reel to be only rotatable in a first, winding direction when the lock can be engaged, and allows the reel to be rotatable in a second, unwinding direction when the lock is disengaged.

Some embodiments can also include a closed loop lace wherein the lace can be mounted in the reel. Accordingly, each of the at least first and second lace guides comprise an open channel to receive the closed loop lace. In some embodiments, the lace is releasably mounted to the reel.

According to another embodiment of the footwear lacing system, a spool and lace unit can be provided for use in conjunction with a footwear lacing system comprising a spool having ratchet teeth disposed on its periphery configured to interact with a pawl for inhibiting relative rotation of the spool in at least one direction, and a lace securely attached to the spool. Optionally, the lace can be formed of a lubricious polymer having a relatively low elasticity and high tensile strength. Alternatively, the lace can be formed of a multi-strand polymeric cable. Alternatively, the lace can be formed of a multi-strand metallic cable, that can have a lubricious polymer casing.

Some embodiments provide a mechanism for tightening and loosening a lace comprising a spool rotatable about a central axis and comprising a plurality of elongate members projecting away from the axis, each elongate member having a free end. The mechanism can also include a housing comprising a plurality of teeth configured to engage the free ends of the elongate members so that as the spool is rotated in a first direction, the engagement of the free ends and the teeth prevent the spool from rotating in the opposite direction but do not prevent rotation of the spool in the first direction so that the lace can be tightened and wound around the spool. A plurality of drive members can be configured to displace the free ends of the elongate members from the teeth when the spool is rotated in a direction opposite to the first direction so as to loosen the lace.

Some embodiments provide a mechanism for tightening and loosening a lace comprising a spool rotatable about a central axis. The mechanism can also comprise a plurality of elongate members projecting away from the axis, each elongate member having a free end, and a plurality of projections also projecting away from the axis. A housing may also be provided comprising a plurality of teeth configured to engage the free ends of the elongate members so that as the spool is rotated in a first direction, the engagement of the free ends and the teeth prevent the spool from rotating in the opposite direction but do not prevent rotation of the spool in the first direction so that the lace can be tightened and wound around the spool. A knob may also be included comprising a plurality of drive members having first and second drive surfaces, the first drive surfaces configured to engage the projections as the knob is rotated in the first direction and the second drive surfaces configured to engage the free ends of the elongate members and displace them from the teeth when the knob is rotated in the opposite direction.

Some embodiments include a stop cord which can prevent a spool from being over-tightened. The stop cord can wind around a separate channel from the lace channel as the spool rotates to tighten the lace. The stop cord's channel can be, for example, a channel formed in the spool, or a channel defined by the bottom surface of the spool and the base of the housing so that the stop cord can wind around the shaft that the spool rotates on. When the stop cord becomes tightly wound around its channel the spool can be prevented from further tightening. By choosing a stop cord of appropriate length the amount that the spool is able to tighten the lace can be limited. In some embodiments, a stop cord length can be chosen that "locks" the spool against further tightening at approximately the position where the lace channel of the spool becomes filled with the lace so that further tightening would risk jamming the spool. In some embodiments, the stop cord can also prevent the spool from being rotated in the loosening direction after the lace has been substantially fully loosened.

Some embodiments provide a reel for use in a lacing system. The reel can include a housing that has a plurality of depressions formed therein, and a spool supported by the housing. The spool can include one or more arms extending therefrom and an annular channel formed therein. The reel can also include a knob supported by the housing. The reel can be configured so that the spool gathers cable in the channel formed in the spool when the spool is rotated in a first direction relative to the housing. The reel can also be configured so that cable can be released from the channel formed in the spool when the spool is rotated in a second direction relative to the housing. In some embodiments, each of the arms extending from the spool defines an unrestrained end portion. Each end portion can be configured to be selectively engageable with each of the plurality of depressions so as to prevent the spool from rotating in the second direction relative to the housing when one or more of the arms is in a relaxed, undisplaced position. In some embodiments, each of the arms is configured so as to not substantially impede the rotatability of the spool in the first direction relative to the housing. The knob can be configured such that, when the knob is rotated in the second direction relative to the housing, the knob causes each of the arms extending from the spool to deflect from the relaxed position of each of the arms so as to disengage each of the arms from the each of the respective depressions with which each of the arms is engaged.

Some embodiments provide a method of gathering and releasing cable from a cable reel. The method can include providing a reel that includes a housing having a plurality of depressions formed therein. The reel can include a spool supported by the housing configured to gather cable around a portion of the spool when the spool is rotated in a first direction relative to the housing and configured to incrementally release an incremental portion of the cable when the spool is rotated in a second direction that is opposite the first direction relative to the housing. The reel can also include a knob supported by the housing. The method can also include rotating the spool relative to the housing in a first direction so as to retract a portion of a cable into the reel by wrapping the cable around a portion of the spool. The method can also include rotating the spool relative to the housing in a second direction that is opposite the first direction so as to incrementally release an incremental portion of the cable from the reel. In some embodiments, a rotational position of the spool relative to the housing is selectively lockable in the second direction but not the first direction.

Some embodiments provide a reel for use in a lacing system. The reel can include a housing and a spool rotatably supported by the housing. The spool can include an annular lace channel formed therein, and the spool can be configured to gather lace into the annular lace channel when the spool is rotated. The reel can further include a stop cord configured to wrap around an annular stop cord channel when the spool is rotated, the stop cord having a length selected to prevent over-tightening of the lace.

Some embodiments provide a method of preventing over-tightening of a lacing system. The method can include rotating a spool relative to a housing thereby gathering lace into an annular lace channel formed in the spool, causing a stop cord to wind around an annular stop cord channel as the spool rotates relative to the housing, and tightening the stop cord around the annular stop cord channel thereby preventing further rotation of the spool.

DETAILED DESCRIPTION OF PREFERRED EMBODIMENTS

Figure 1:
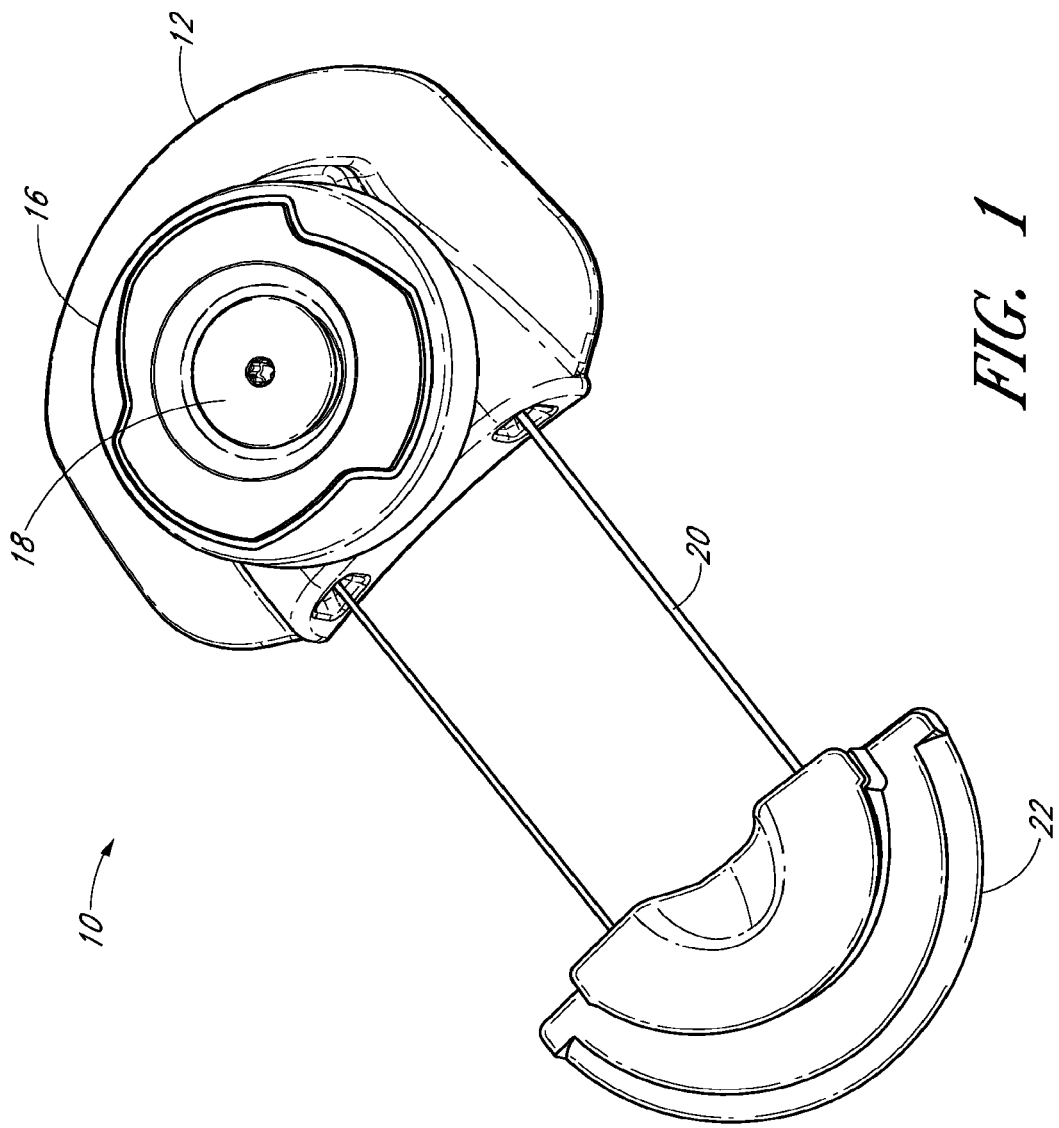
FIG. 1 is a perspective view of an embodiment of a reel based lacing system.
Figure 2:
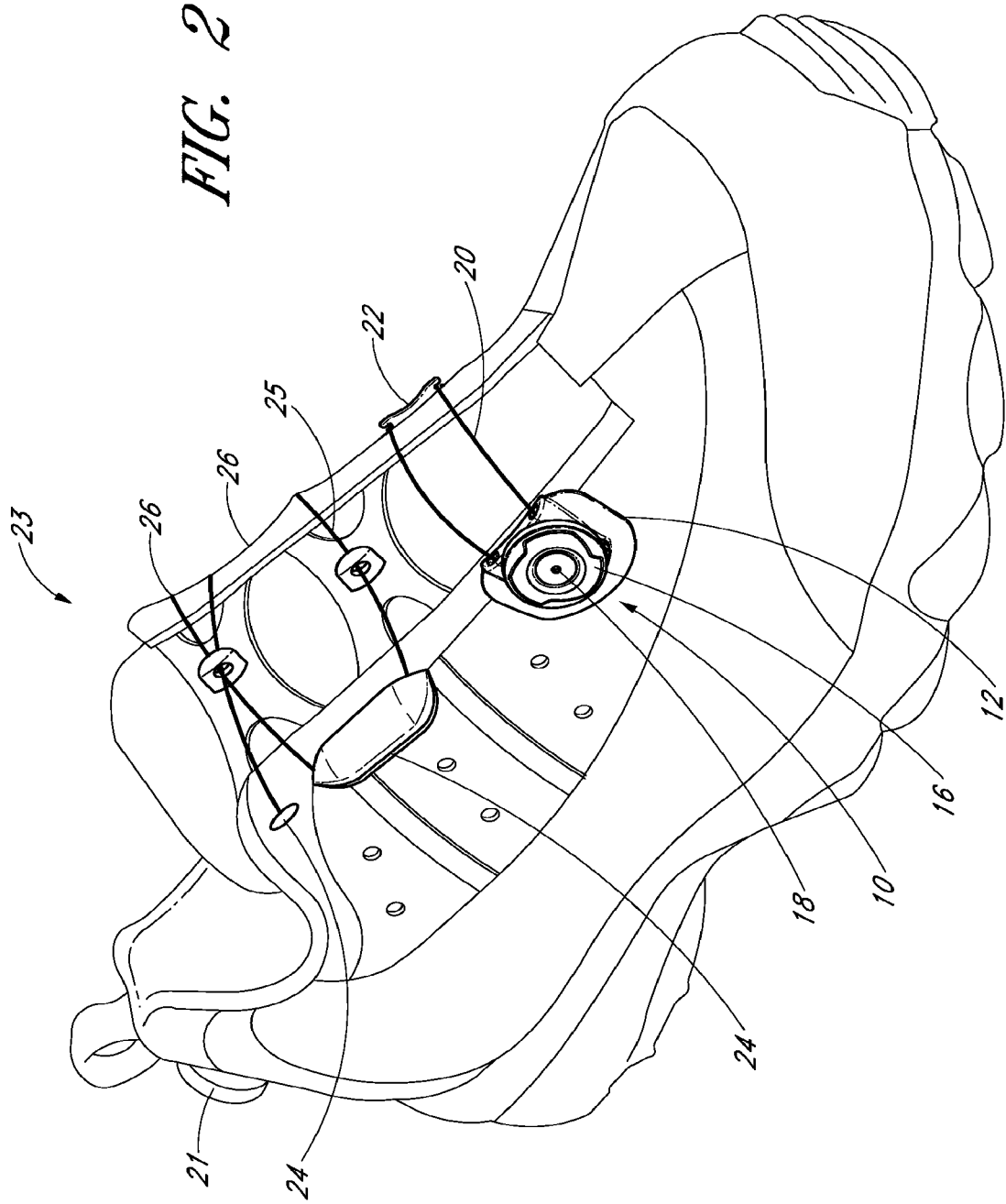
FIG. 2 is a perspective view of a sport shoe comprising the embodiment of the reel based lacing system of FIG. 1.
Figure 3:
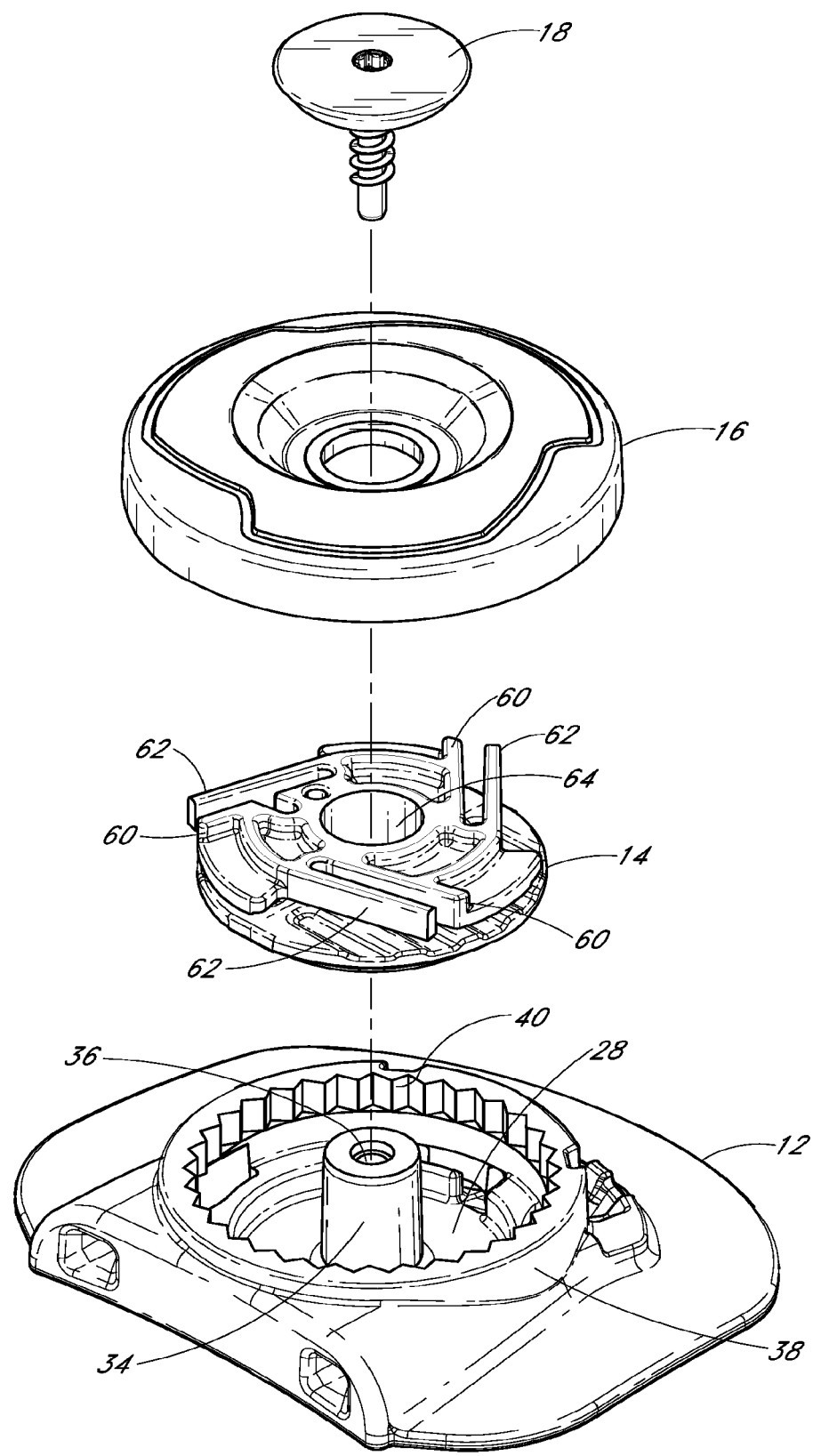
FIG. 3 is an exploded perspective view of the embodiment of the reel based lacing system of FIG. 1.

FIG. 1 is a perspective view of an embodiment of a reel based lacing system 10. FIG. 2 is a perspective view of a sport shoe comprising the embodiment of the reel based lacing system 10 shown in FIG. 1. The sport shoe can be an athletic shoe, including a running shoe, basketball shoe or otherwise, an ice skating or other action sport shoe, a snowboarding boot, or any other suitable footwear that can be tightened around a wearer's foot (collectively referred to as a shoe or sport shoe). The lacing system 10 can be removably mounted to the front, back, top, side, or any other suitable portion of the sport shoe. FIG. 3 is an exploded perspective view of the embodiment of the reel based lacing system of FIG. 1.

Any of the embodiments of the lacing systems disclosed herein, or any suitable component or feature of the lacing systems disclosed herein, can be used with any of the closure or reel systems described in any of the documents incorporated herein by reference. Any of the embodiments, components, or features of the lacing systems disclosed or incorporated herein can be combined to create additional embodiments of lacing systems not explicitly described herein or in the disclosures incorporated herein, forming new embodiments that are contemplated as being a part of the present disclosure.

Additionally, although various embodiments of lacing systems are described herein, the various components, features, or other aspects of the embodiments of the lacing systems described herein can be combined or interchanged to form additional embodiments of lacing systems not explicitly described herein, all of which are contemplated as being a part of the present disclosure.

With reference to FIGS. 1-3, the lacing system 10 can include a housing 12, a spool 14, a knob 16, a fastener 18, a lace member or cable 20, and a lace guide or guide member 22. As used herein, the terms lace and cable have the same meaning unless specified otherwise. As shown in FIG. 2, in some embodiments, the lacing system 10 can be used with other lacing or tightening systems such as, for example and without limitation, tightening system 23 having lace 25, heal-mounted lace winder 21, and lace guides 24, 26. Other suitable or desired lace guides can be supported by the sport shoe in any desired position for routing the lace 20, lace 25, or any other lace over portions of the sport shoe. Typically, the housing 12, tightening system 23, and guides 22, 24, 26, will be attached to the outer shell of the sport shoe, but the sport shoe can have additional guides supported by the tongue of the sport shoe through which the lace 20 can be threaded. In some embodiments, more or fewer than the number of lace guides shown in FIG. 2 can be attached to the sport shoe. As will be described in greater detail below, in some embodiments, one end of the lace 20 can be fixed to the housing 12, while the other end of the lace 20 can be threaded through the lace guides attached to the sport shoe and be attached to the spool 16 so as to permit the lace 20 to be tightened around the spool 16 when the knob 18 is turned. In some embodiments, the lace 25 can be omitted, and the lace 20 can be threaded through the guides 24 and 26 such that the lacing system 10 can operate to tighten the tightening system 23 as well as to draw the guide 22 closer to the housing 12.

The lace 20 can be a low friction lace that slides easily through the boot and/or lace guides and automatically equilibrates tightening of the boot over the length of the lacing zone, which can extend along the ankle and foot. Although the present embodiments will be described with reference to a sport shoe, as mentioned above, it is to be understood that the principles discussed herein are readily applicable to any of a wide variety of footwear, outer wear, bags, bindings, or other similar or suitable objects.

Generally, the lace 20 can be tensioned to draw the guide 22 closer to the housing 12. Similarly, the tightening system 23 can be tensioned to draw the guides 24, 26 closer to one another. Thus, references herein to drawing opposing sides of footwear towards each other refers to the portion of the footwear designed to be drawn together to hold the footwear to the foot of a user. Often, these portions of the footwear are disposed along a centerline on the sides of the foot. In some embodiments, access to the footwear is disposed off the centerline of the footwear, for example, to the side of the centerline or at the rear of the footwear. This reference can be thus generic to footwear in which opposing edges remain spaced apart even when tight (e.g. tennis shoes) and footwear in which opposing edges can overlap when tight (e.g. certain snow skiing boots). In both, tightening can be accomplished by drawing opposing sides of the footwear towards each other.

As shown in FIG. 2, the lace 20 can be threaded through a guide 22 located on the shell of the sport shoe on the opposite side of the tongue of the sport shoe from the housing 12. As also illustrated in FIG. 2 and mentioned above, the reel based lacing system 10 can be used in conjunction with any other suitable or desired tightening system or systems, such as but not limited to the heel mounted tightening system 23 illustrated in FIG. 2 and disclosed more fully in U.S. Application Publication No. 2006-0156517.

As illustrated, the tightening system 23 can be threaded through the heel or ankle portion, or other portions of the sport shoe. The tightening system 23 can have lace 25 that can slide through the guides 24, 26 during tightening and untightening of the lace 25, and can form a crossing pattern along the midline of the foot between the guides 24, 26. In the illustrated embodiment, three guides 22, 24, 26 are attached to the sport shoe. However, any suitable number of guides can be attached to the sport shoe. In some embodiments, three, four, five, or six or more guides can be positioned on each side of the boot, each of the guides being similar or different to one another. In some embodiments, more than one reel based lacing system 10 can be mounted at different locations on a shoe, each reel based lacing system having lace and a guide (such as, but not limited to, guide 22) mounted at various locations on the shoe.

The housing 12, tightening system 23, and any of the guides, including guides 22, 24, 26, can be attached to the sport shoe by any suitable fastener or fastening method including but not limited to rivets, screws, pins, stitching, adhesives, or by using other suitable fasteners or fastening methods. As will be described in greater detail below, the housing 12 and the guides 22, 24, 26, can be sized and shaped, or otherwise configured, to be suitable for any type of sport shoe, shoe, or other object to which the housing and guides will be attached, or based on other performance characteristics such as tension requirements, weight, size, or other considerations. In some embodiments, stitching the housing 12 or guides 22, 24, 26 directly to the outer shell of the sport shoe can permit optimal control over the force distribution along the length of the guides. For example, when the lace 20 is under relatively high levels of tension, the guides can tend to want to bend and to possibly even kink or buckle. Bending of the guide member under tension can increase friction between the guide member and the lace 20, and, severe bending or kinking of the guides can undesirably interfere with the intended operation of the lacing system. Thus, the size, materials, and shape of the housing 12 and/or guides, as well as the attachment mechanism for attaching the housing 12 and/or guides to the sport shoe, can have a bearing on the ability of the housing 12 and/or guides to resist bending and/or kinking.

In some embodiments, the footwear lacing system 10 described herein can allow a user to incrementally tighten the boot around the user's foot. In some embodiments, the low friction lace 20 combined with low friction guide members can produce easy sliding of lace 20 within the guide members. The lace 20 can equilibrate tension along its length so that the lacing system 10 can provide an even distribution of tightening pressure across the foot. As will be described in greater detail below, the tightening pressure can be incrementally adjusted by turning the knob 16 relative to the housing 12. For example, in some embodiments, as will be described in greater detail below, a user can incrementally tighten the lacing system 10 and, hence, the sport shoe, by turning the knob 16 in a first direction relative to the housing 12. Similarly, in some embodiments, a user can incrementally loosen the lacing system 10 and, hence, the sport shoe, by turning the knob 16 in a second direction relative to the housing 12. In some embodiments, a user can also loosen the lacing system 10 by lifting or pressing the knob 16 so as to disengage the spool 14 from the housing 12 or operating any alternative release mechanism to automatically release the lace 20 from the spool 14.

With reference to FIG. 3, the spool member 14 can be supported within the depression 28 formed in the housing 12. As will be described in greater detail below, in some embodiments, the spool 14 and the housing 12 can be configured so that the spool 14 generally freely rotates in a first direction (a tightening direction) relative to the housing 12. Additionally, in some embodiments, the spool 14 and the housing 12 can be configured so that the spool 14 is generally restrained from freely rotating in a second direction (a loosening direction) relative to the housing 12. The knob 16 can be mechanically coupled to the housing 12 using the fastener 18 or any other suitable fastener or fastening method. In some embodiments, the knob 16 can be coupled to the housing 12 so that the knob 16 is axially restrained but rotationally free so that the knob 16 can generally freely rotate relative to the housing 12 except as described herein.

The knob 16 can be configured to drive the spool member 14 in a first direction to gather lace 20 on the spool 14 so as to tighten the lacing system 10. Additionally, the knob 16 can be configured to drive the spool member 14 in a second direction so as to cause the spool member 14 to incrementally release lace 20 that has gathered on the spool 14 so as to incrementally loosen the lacing system 10. Therefore, in some embodiments, the spool member 14 can be configured to serve the function of gathering lace 20 as the lacing system 10 is tightened, and also can be configured to function with features on the housing 12 and knob 16 to provide for the incremental release of lace 20 of the lacing system 10 when the lacing system 10 is loosened.

Figure 4:
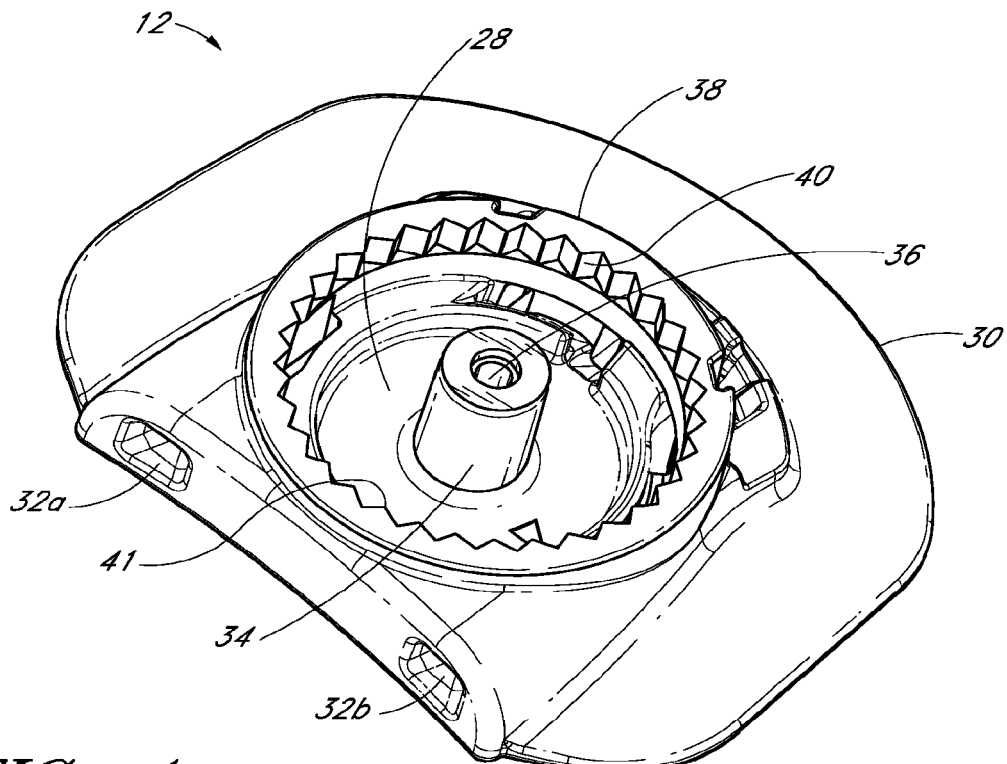
FIG. 4 is a perspective view of the embodiment of the housing of the embodiment of the reel based lacing system of FIG. 1.
Figure 5:
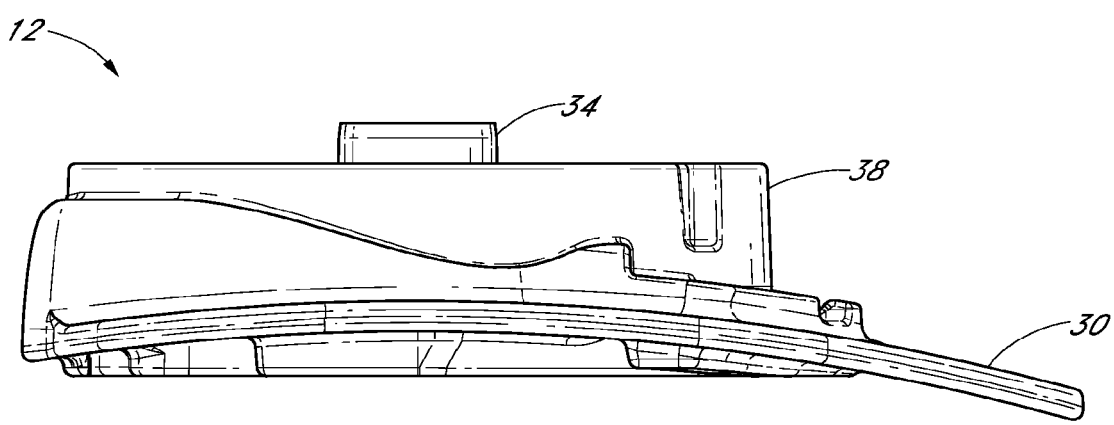
FIG. 5 is a side view of the embodiment of the housing shown in FIG. 4.
Figure 6:
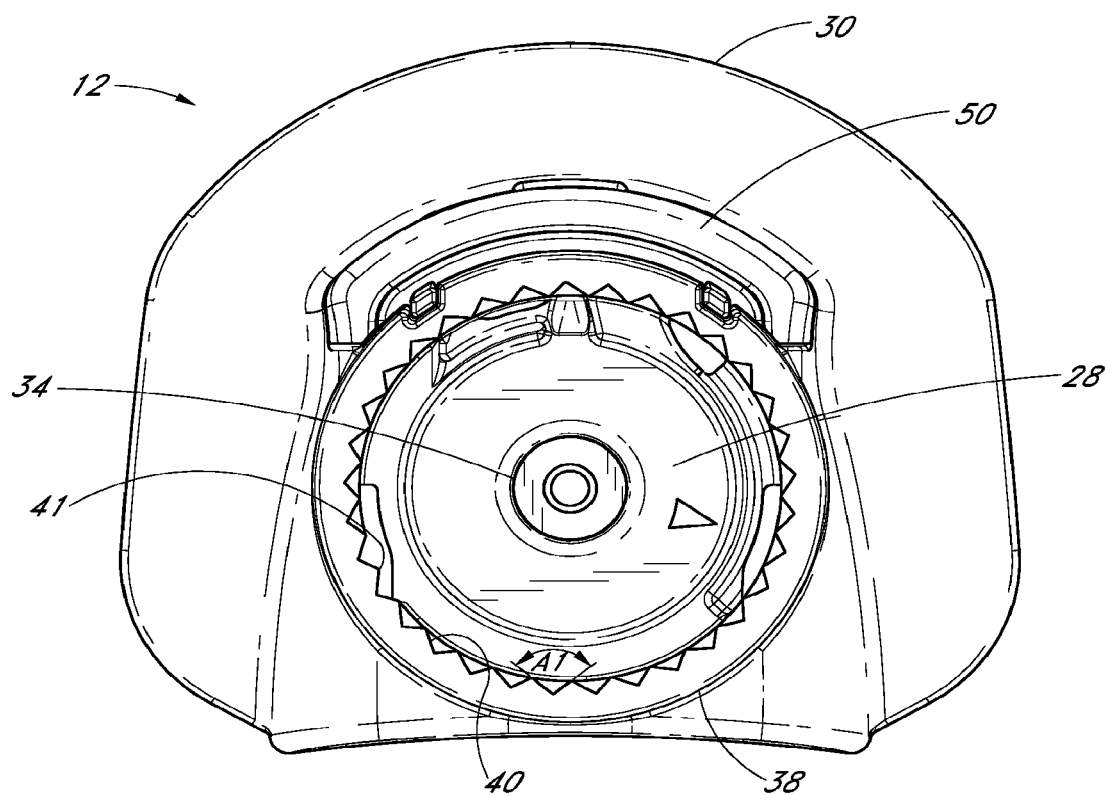
FIG. 6 is a top view of the embodiment of the housing shown in FIG. 4.

FIG. 4 is a perspective view of the embodiment of the housing 12 of the embodiment of the reel based lacing system 10 of FIG. 1. FIGS. 5 and 6 are a side view and top view, respectively, of the embodiment of the housing 12 shown in FIG. 4. With reference to FIGS. 4-6, in some embodiments, the housing 12 can comprise a mounting flange 30 that can be configured to permit the housing 12 to be attached to the sport shoe. The mounting flange 30 can be configured in accordance with the desired mounting method or mounting fasteners, the contour shape of the sport shoe or other object to which it is to be fastened, the performance characteristics of the lacing system 10, or other factors. For example, as shown most clearly in FIG. 5, the mounting flange 30 can be curved to facilitate attaching the housing 12 to a curved surface of the sport shoe or other objects to which the housing 12 can be mounted. Additionally, as mentioned, the mounting flange 30 can be sized and configured to accommodate stitching, rivets, or any other suitable or desired fasteners or fastening method to fasten the housing 12 to the desired object.

In some embodiments, the housing 12 can be configured so as to be mountable to the sport shoe or other object without the existence or use of the flange 30. For example, in some embodiments (not shown), when the housing 12 does not have a flange 30, screws or other fasteners can be used to mount the housing 12 to the sport shoe or other desired object by threading into a bottom surface of the housing 12. In some embodiments, a housing 12 with a flange 30 can be attached to the sport shoe or other object using screws.

With reference to FIG. 4, the housing 12 further comprises a pair of lace inlet openings 32. The lace inlet openings 32 can be configured to permit the lace 20 to be threaded into the housing 12. Depending on the desired configuration of the lacing system 10, for example, in some embodiments, the portion of the lace 20 (not shown) that is desired to be wound around the spool 14 can enter the housing 12 through the lace inlet 32a, while the portion of the lace 20 that enters the housing 12 through the lace inlet 32b can be anchored to the housing 12 so that it is not wound around the spool 14 when the spool 14 is rotated relative to the housing 12. Additionally, in some embodiments, the portion of the lace 20 (not shown) that is desired to be wound around the spool 14 can enter the housing 12 through the lace inlet 32b, while the portion of the lace 20 that enters the housing 12 through the lace inlet 32a can be anchored to the housing 12 so that it is not wound around the spool 14 when the spool 14 is rotated relative to the housing 12. Additionally, some embodiments of the lacing system 10 can be configured such that the portions of the lace 20 (not shown) entering both of the lace inlets 32a, 32b are wrapped around the spool 14, which can be a single layer spool, a double layer spool or otherwise.

As will be described in greater detail below, one or more of the openings 32 can be configured to provide a conduit for lace 20 to be threaded through the housing 12 so as to be in communication with the depression 28. In this configuration, lace 20 threaded through either or both of the openings 32 can be threaded into the depression 28 of the housing 12 so that it can be wound around the spool 14 as the spool 14 is rotated relative to the housing 12. Additionally, in some embodiments, one or more of the openings 32 can be configured to route the lace 20 through the housing 12 into a channel or other object that allows an end portion of the lace 20 that is not intended to be wound around the spool 14 to be anchored or otherwise secured to the housing 12. In some embodiments, the lacing system 10 can be configured such that only one end of the lace 20 is attached to the housing 12.

Some embodiments of the housing 12 can comprise a shaft 34 that can project from the depression 28 and, as will be described, can provide a generally cylindrical supporting surface for the spool 14. The shaft 34 can provide a supporting surface about which the spool 14 can freely rotate. In some embodiments, the shaft 34 can be fixed to the housing so as to not rotate relative to the housing 12. However, in some embodiments, the shaft 34 can be configured so as to rotate freely relative to the housing 12 to further facilitate the free rotation of the spool 14 relative to the housing. As shown in FIG. 4, the shaft 34 can also have an opening 36 that can be generally coaxially aligned with the longitudinal axis of the shaft 34. The opening 36 can be configured to receive the fastener 18 or other fastener used to couple the knob 16 to the housing 12. In some embodiments, the opening 36 can be threaded. In some embodiments, the opening 36 can be unthreaded but configured so that, when a threaded fastener such as the fastener 18 is rotationally inserted into the opening, the fastener 18 threads into the opening 36 so as to generally axially secure the fastener 18 to the shaft 34. In some embodiments, the knob 16 can be coupled to housing 12 using a rivet formed from plastic, metal, or any other suitable material. In some embodiments, the fastener 18 can be ultrasonically welded to the housing 12 to attach the knob 16 to the housing 12.

With reference to FIG. 4, the housing 12 can have a generally cylindrical shaped wall 38 projecting generally coaxially with the shaft 34. The interior space between the wall 38 and the shaft 34 defines the volume of space referred to above as the cavity or depression 28. A plurality of radially positioned notches or depressions 40 can be formed on an inside surface of the wall 38 so as to form a series of radially position ratcheting teeth 41 for controlling the incremental rotation of the spool 14, as will be described in greater detail below. In the illustrated embodiment, the depressions 40 can define a generally triangular cross-sectional shape. However, the shape, size, or other details of the depressions 40 are not confined to those shown in FIG. 4. The depressions can define any shape, size, or other configuration suitable for controlling the rotation of the spool 14 as described herein. For example, in some embodiments, the points of the teeth 41 projecting from the depressions 40 can be rounded. Additionally, the corners of the depressions 40 can have a rounded but generally triangular shape.

In some embodiments, any number of depressions 40 can be formed in the wall 38. The number of depressions 40 that can be formed in the wall 38 can affect the level of adjustability of the lacing system 10 in both tightening and loosening since, as will be described in greater detail, the depressions can provide stops or ratchet points which can secure a portion of the spool member 14 in any of the multitude of depressions 40. Thus, increasing the number of uniformly spaced depressions 40 can decrease the amount of angular rotation required by the spool 14 relative to the housing 12 for the spool 14 to move relative to each of the depressions 40. As the size of the housing 12 increases, the size of the depressions 40 formed in the wall 38 can also be increased to maintain the same amount of angular rotation required by the spool 14 relative to the housing 12 for the spool 14 to move from one depression 40 to the next depression 40.

In the illustrated embodiment, approximately 33 depressions 40 can be formed in the wall 38 of the housing 12. In some embodiments, between approximately 33 and approximately 40 or more depressions can be formed in the wall of the housing 12. In some embodiments, between approximately 25 or less and approximately 33 depressions 40 can be formed in the wall of the housing 12. However, any desired number of depressions 40 can be formed in the housing 12. In general, the degree of adjustability can be controlled by the number of depressions 40. With more depressions, each step of the spool 14 along those depressions 40 is reduced and therefore the incremental amount of tension applied to or released from the system is reduced. Similarly, decreasing the number of depressions 40 increases the distance between steps and increases the incremental tension applied to or released from the system with each step.

The angle A defining each depression 40 can be uniform such that the shape of each depression 40 is substantially the same. In some embodiments, the angle A defining each depression 40 can be an obtuse angle (greater than 90 degrees), as shown in FIG. 6. In some embodiments, the angle A defining each depression 40 can be approximately 100 degrees, or can be between approximately 90 degrees or less and approximately 100 degrees, or between approximately 90 degrees and approximately 100 degrees, or between approximately 100 degrees and approximately 110 degrees, or between approximately 110 degrees and approximately 120 degrees or more.

Figure 7:
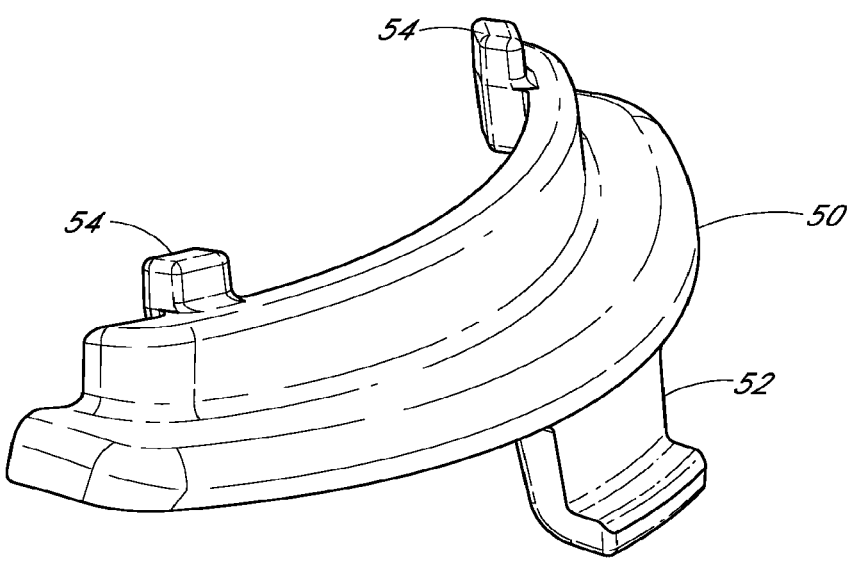
FIG. 7 is a perspective view of an embodiment of a cover member that can be coupled to the embodiment of the housing shown in FIGS. 4-6.
Figure 8:
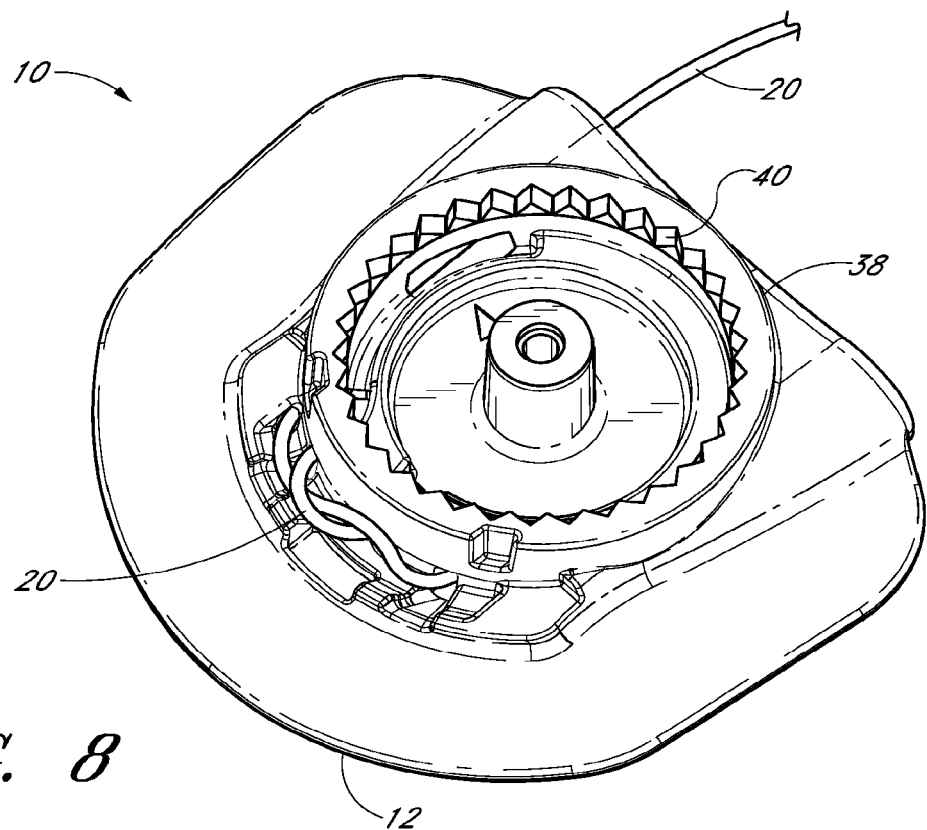
FIG. 8 is a perspective view of the embodiment of the housing shown in FIGS. 4-6 without the embodiment of the cover member shown in FIG. 7 attached, showing a portion of lace threaded through a portion of the embodiment of the housing.

FIG. 7 is a perspective view of an embodiment of a cover member 50 that can be coupled to the embodiment of the housing 12 shown in FIGS. 4-6. FIG. 8 is a perspective view of the embodiment of the housing 12 shown in FIGS. 4-6 without the cover member 50 attached, showing a portion of lace 20 threaded through a portion of the housing 12. In some embodiments, as is shown in FIG. 6, the cover member 50 can be coupled to the housing 12 to substantially enclose a portion of the housing 12 adjacent to the wall 38 that provides the receiving area for an end portion the lace 20, as is shown in FIG. 8. The cover member 50 can be removable from the housing 12 so that a user or manufacturer can have access to the end portion of the lace 20 threaded through the housing 12 to for example, without limitation, have the ability to replace the lace 20.

In the illustrated embodiment, as shown in FIG. 8, the lace 20 can be woven through a series of three or more openings (not shown) formed in the housing 12 or woven through any suitable geometry that substantially prevents the lace 20 from becoming inadvertently removed from the housing 12. Each opening can cause the lace 22 to be deflected over an edge that defines an angle between approximately 30 and approximately 100 degrees, which can create a sufficient level of friction to prevent the lace 20 from becoming disengaged from the housing 12. In this manner, one of the end portions of the lace 20 can be anchored to the housing 12. A free end of the lace 20 can then be passed under a loop of lace 20 created by weaving the lace through the three or more openings. In some embodiments, the lace 20 can be woven through a greater or lesser number of openings to properly anchor or secure the end portion of the lace 20 to the housing 12.

Additionally, the lace 20 can be knotted or an anchor member can be removably or non-removably attached to the end portion of the lace 20 to prevent the lace 20 from inadvertently sliding out of the housing 12. In some embodiments, a labyrinth knot can be used to secure the end portion of the lace 20 to the housing 12. After the end portion of the lace 20 has been sufficiently secured to the housing 12, the cover member 50 can be removably or non-removably attached or affixed to the housing 12. With reference to FIG. 7, some embodiments the cover member 50 can define a tabbed protrusion 52 and tabbed protrusions 54 that can be configured to engage with suitable complementary features on the housing 12 to prevent the inadvertent removal of the cover member 50.

Figure 9:
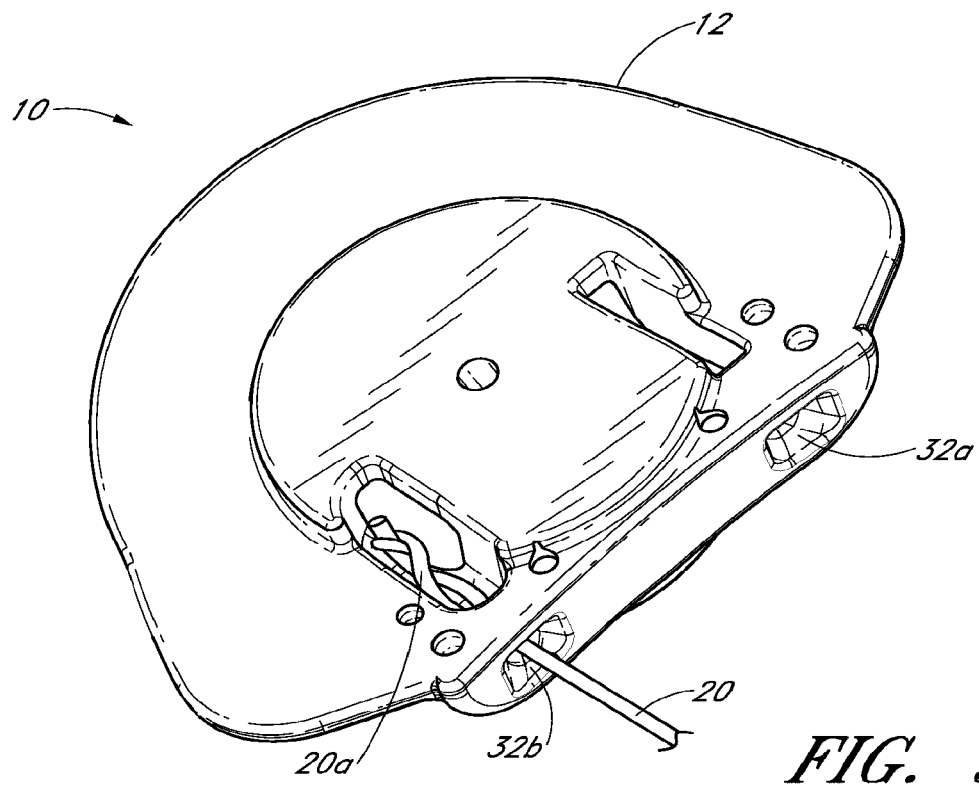
FIG. 9 is a perspective view of the bottom portion of another embodiment of a housing, showing a portion of lace threaded through a portion of the embodiment of the housing.

FIG. 9, which is a perspective view of the bottom portion of another embodiment of a housing 12, shows a portion of lace 20 threaded through a portion of the embodiment of the housing 12. In this embodiment, a knot 20a can be formed in the end portion of the lace 20 to prevent the lace 20 from being inadvertently pulled through the opening 32b as the lacing system 10 is being tightened or otherwise. In some embodiments, an anchor member (not shown) having a size and geometry that is larger than the size and geometry of the cross-section of the opening 32b can be attached to the end portion of the lace 20 to prevent the lace 20 from becoming inadvertently pulled out or removed from the housing 12. For example, without limitation, a spherical or other shaped object can be molded on the end of the lace 20, the object being sized and configured to prevent the lace 20 from becoming inadvertently pulled out of or removed from the housing 12. In some embodiments, the object molded on the end of the lace 20 can be a melted ball.

In this configuration, a user can have access to the knot or anchor member attached to the lace 20 in order to remove and replace the lace 20 of the lacing system 10. While, in the configuration shown in FIG. 9, the user can access the knot 20a by accessing the bottom surface of the housing 12, in some embodiments, the housing 12 can be configured so that the knot 20a can be accessed from the top surface or top portion of the housing 12 so that a user is not required to remove the housing 12 from the sport shoe or other object in order to remove and replace the lace 20. In some embodiments, the lacing system 10 can be configured such that any knot (for example, but not limited to, knot 20a) or other end portion of the lace 20 can be accessed from the top or external portion of the housing 12. In some embodiments one end of the lace 20 can be attached to the housing 12 using an adhesive and/or the other end of the lace 20 can be attached to the spool 14 using an adhesive.

In some embodiments, one end of the lace 20 can be attached to the spool member 14, while the distal end of the lace 20 can be attached to the article to which the lace system 10 is supported, the distal end of the lace 20 being attached to a portion of the object that is peripheral to the housing 12 and spool member 14 so that only one end of the lace 20 is routed through the housing 12 and/or spool member 14.

Figure 10:
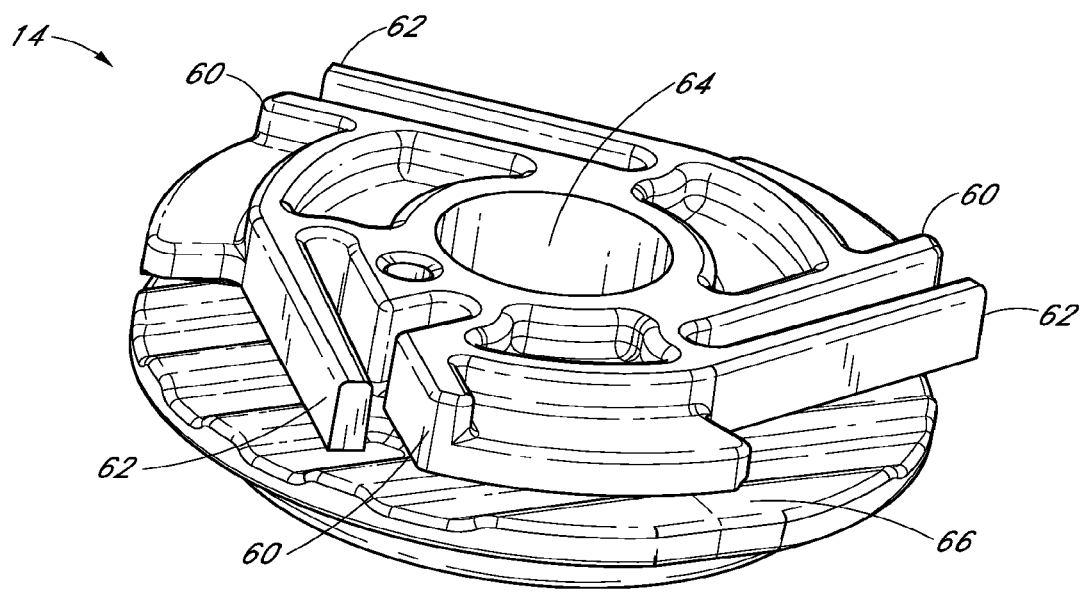
FIG. 10 is a perspective view of the embodiment of the spool member of shown in FIG. 3.
Figure 11:
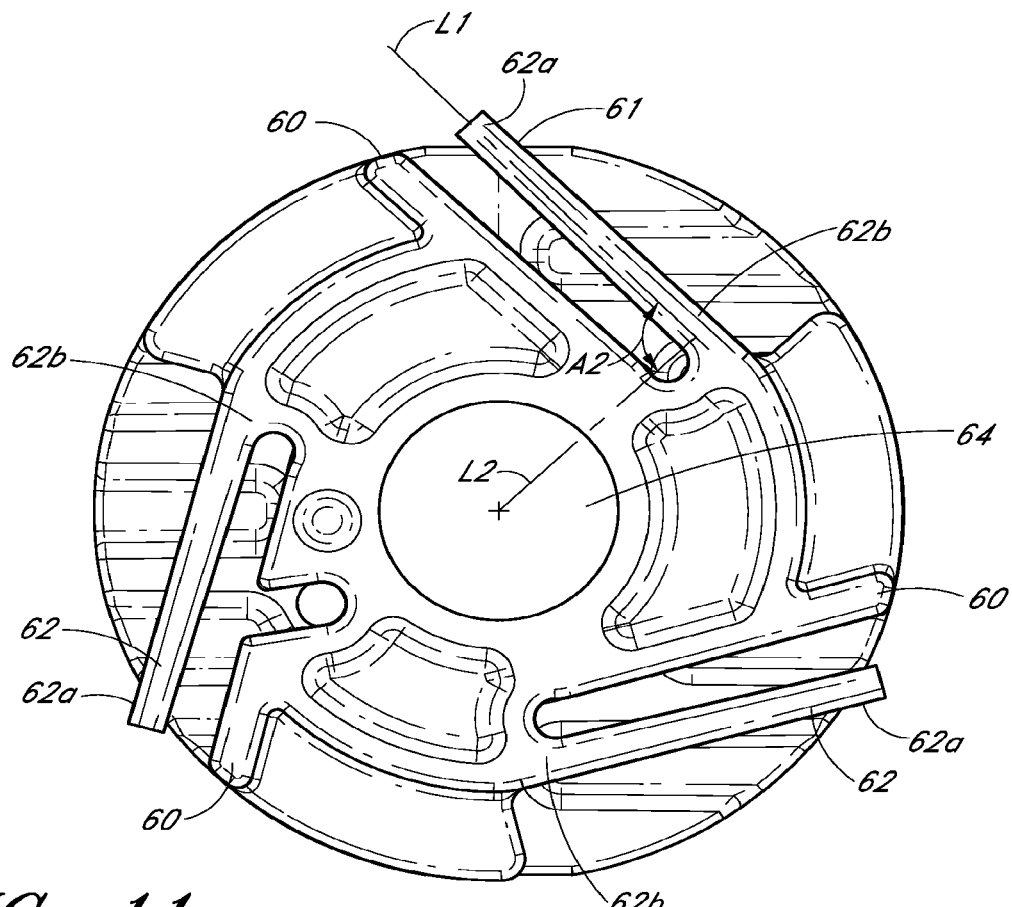
FIG. 11 is a top view of the embodiment of the spool member shown in FIG. 3.
Figure 12:
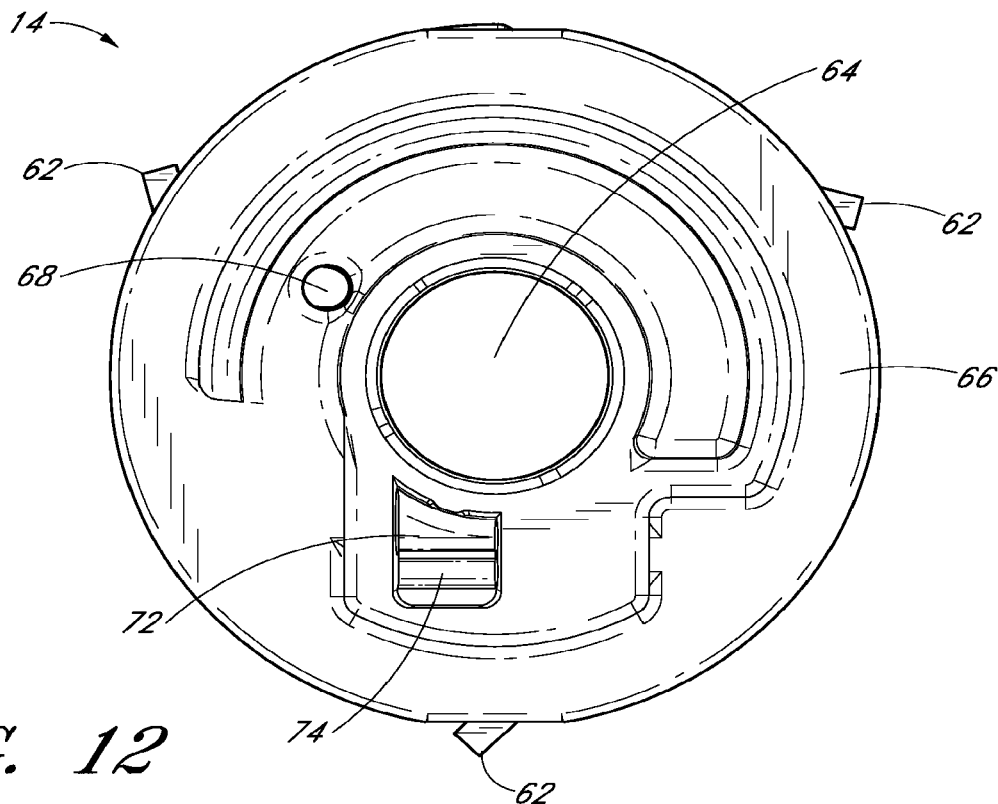
FIG. 12 is a bottom view of the embodiment of the spool member shown in FIG. 3.
Figure 13:
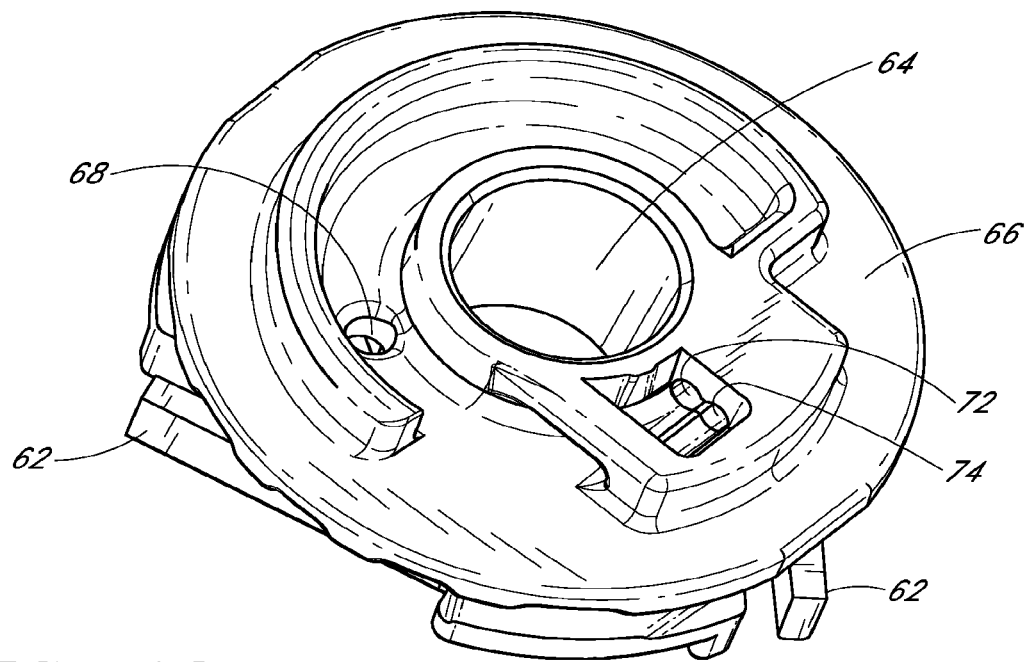
FIG. 13 is a perspective view of the bottom portion of the embodiment of the spool member shown in FIG. 3.

FIGS. 10-12 are a perspective view, top view, and bottom view, respectively, of the embodiment of the spool member of the lacing system shown in FIG. 3. FIG. 13 is a perspective view of the bottom portion of the embodiment of the spool member 14 shown in FIG. 3. As most clearly shown in FIGS. 10-11, in some embodiments, the spool member 14 can have one or more driven members or projections 60 and one or more pawls 62 (also referred to herein as arms). In the illustrated embodiment, the spool member 14 can have three driven members 60 and three pawls 62. In some embodiments, as in the illustrated embodiment, the number of pawls 62 can correspond with the number of driven members 60. In some embodiments, the number of pawls 62 can be different than the number of driven members 60. In some embodiments, the spool member 14 can have less than or greater than three driven members 60 and/or pawls 62.

Additionally, the spool member 14 can have an opening 64 having a centerline axis that is generally aligned with the symmetrical centerline axis of the spool member 14. With reference to FIGS. 10-13, the opening 64 can be generally cylindrical in shape and sized and configured to be slightly larger than the outer surface of the shaft 34 of the housing 12. In this configuration, the spool member 14 can be supported by the housing 12 so that the opening 64 of the spool member 14 is positioned around the outside of the shaft 34 of the housing 12 and so that the spool member 14 is able to freely rotate around the shaft 34 of the housing.

As most clearly shown in FIG. 11, the spool member 14 can be configured such that each of the pawls 62 is essentially a cantilevered tab or protrusion having an unsupported end portion 62a while having a supported base portion 62b that can provide moment support to the base portion 62b of the pawl 62. As such, the spool member 14 can be configured so as to prevent each of the pawls 62 from pivoting at the base portion 62b of each of the pawls 62. Additionally, as shown in FIG. 11, the spool 14 can be configured such that each of the pawls 62 is positioned so as to form an approximately 90 degree angle relative to a radial line projecting from the center point of the generally circular spool member 14 and intersecting with the base portion 62b of each of the pawls 62. In particular, with reference to FIG. 11, each of the pawls 62 can be positioned such that a centerline of each of the pawls 62 (represented by line L1) forms an approximately 90 degree angle (represented by angle A2) relative to the line L2 projecting from the approximate center point of the spool member 14 when line L2 intersects with the base portion 62b of each of the pawls 62. Additionally, each of the pawls 62 can be sized, positioned, and configured so as to bend or deflect a desired amount relative to the centerline L1 of the relaxed pawl 62 without obstruction from other components or features of the spool member 14, such as, but not limited to, the driven members 60.

Figure 14:
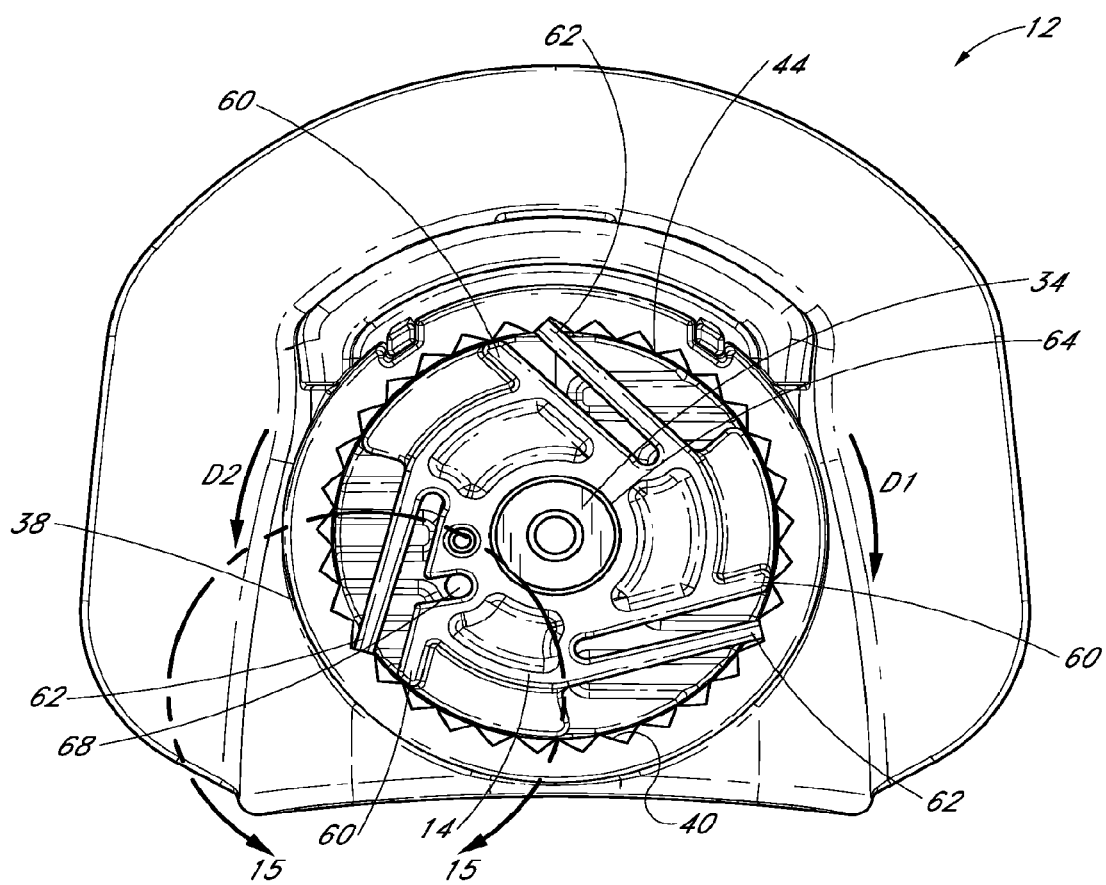
FIG. 14 is a top view of the embodiment of the spool member shown in FIG. 3 positioned in the embodiment of the housing shown in FIG. 1.
Figure 15:
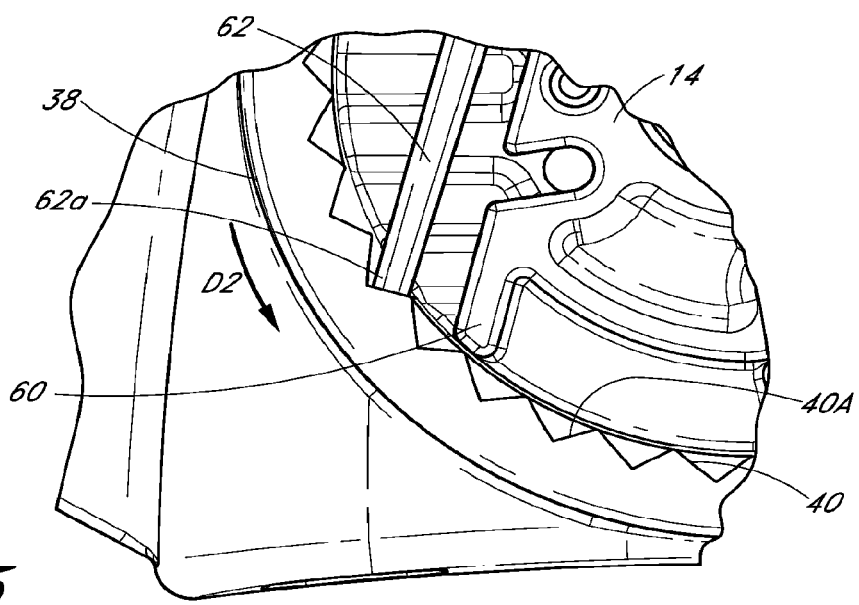
FIG. 15 is an enlarged view of a portion of FIG. 14.

FIG. 14 is a top view of the embodiment of the spool member 14 shown in FIG. 3 positioned in the depression 28 of the embodiment of the housing 12 shown in FIG. 1. FIG. 15 is an enlarged view of a portion of FIG. 14. With reference to FIGS. 14-15, the end portions 62a of each of the pawls 62 can be sized and configured so as to settle into each of the depressions 40 formed in the wall 38 of the housing 12 (i.e., such that the end portions 62a abut against the first surface 40a of each of the depressions 40, as illustrated most clearly in FIG. 15). In this configuration, when each of the pawls 62 is engaged with each of the depressions 40 as described above, the spool member 14 can be prevented from rotating in a second direction (represented by arrow D2 in FIG. 14) relative to the housing 12.

As mentioned above, the pawls 62 and the depressions 40 can be sized and configured so that the end portions 62a of each of the pawls 62 do not engage with the first surfaces 40a of each of the depressions 40 as the spool member 14 is rotated in a first direction (represented by arrow D1 in FIG. 14) relative to the housing 12. However, in this configuration, the pawls 62 can contact each of the teeth or protrusions 44 as the spool member 14 is rotated in a first direction D1. In this manner, the pawls 62 and depressions 40 can be configured to generally allow the spool member 14 to generally freely rotate in the first direction D1 to tighten the lacing system 10, while being incrementally releasable, as will be described in greater detail below, so as to allow the spool member 14 to rotate incrementally in a second direction D2 to incrementally release the tension in the lacing system 10. As mentioned above, with reference to FIG. 15, the end portion 62a of each of the pawls 62 can be configured to contact and abut the first surface 40a of each of the depressions 40, which would inhibit the spool member 14 from rotating in the second direction D2 relative to the housing 12. In some embodiments, the depressions 40 can be sized and shaped so that one or more surfaces of the depression 40 are approximately perpendicular to longitudinal axis of the pawls 62.

Figure 16:
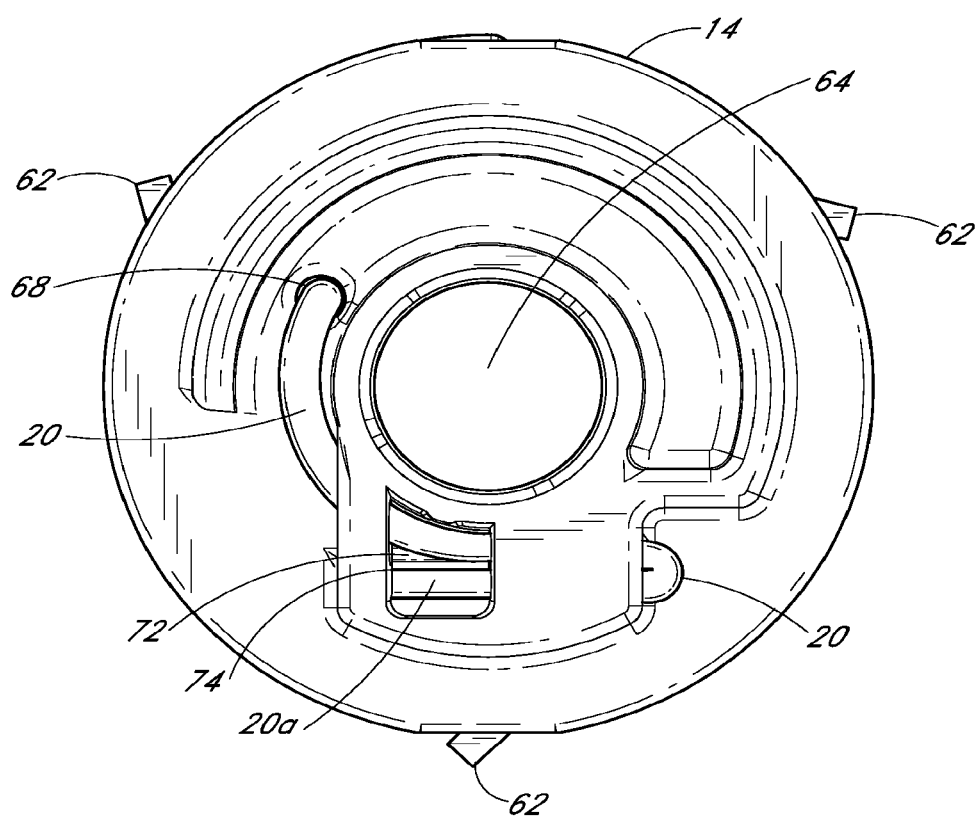
FIG. 16 is a bottom view of the embodiment of the spool member shown in FIG. 3, illustrating a portion of lace supported by the spool member.
Figure 17:
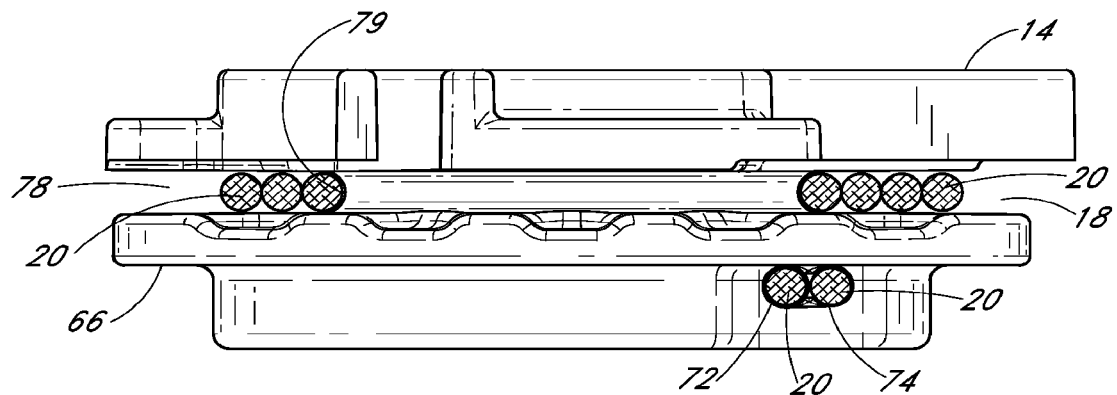
FIG. 17 is a side view of the embodiment of the spool member shown in FIG. 3, illustrating a portion of lace supported by the spool member.

FIGS. 16 and 17 are a bottom view and a side view, respectively, of the embodiment of the spool member 14 shown in FIG. 3 illustrating a portion of lace 20 supported by the spool member 14. The end portion of the lace 20 can be attached to the spool member 14 using any of a number of suitable fasteners or fastening means, including those described above in connection with attaching the lace 20 to the housing 12. In the embodiment illustrated in FIGS. 16-17, the end portion of the lace 20 can be threaded through the opening 68 in the bottom portion 66 of the spool member 14 and routed through a first channel 72 and then a second channel 74 formed in the spool member 14 as illustrated. In particular, the lace 20 can be routed through the spool member 14 so that the lace 20 is routed through the first channel 72, then forms an approximately 180 degree bend, and is then routed so that the end portion 20a of the lace 20 is positioned within the channel 72 formed in spool 14. In this manner, the end portion 20a of the lace 20 can be secured to the spool member 14. However, as mentioned above, any other suitable fasteners or fastening methods can be used to secure the lace 22 the spool member 14.

Additionally, as illustrated in FIG. 17, as the spool 14 is turned in a tightening direction relative to the housing 12, lace 20 can be wound around the channel 78 formed in the spool 14. The channel 78 can be configured to receive lace as the lace is gathered by the spool 14. As is illustrated in FIG. 17, the channel 78 can have a radially outwardly facing surface 79 having an approximately semicircular, "C" shaped, or "U" shaped cross-section for receiving the lace 20, or any other suitable cross-section. In the illustrated embodiment, the spool member 14 can have a channel 78 configured to wind the lace 20 in generally a single plane or level. However, in some embodiments, the spool member can have more than one channel 78 each configured to wind the lace 20 in generally a single plane. Additionally, in some embodiments, the size of the channel 78 can be increased so that multiple levels or layers of lace 20 can be wound around the spool 14.

Figure 18:
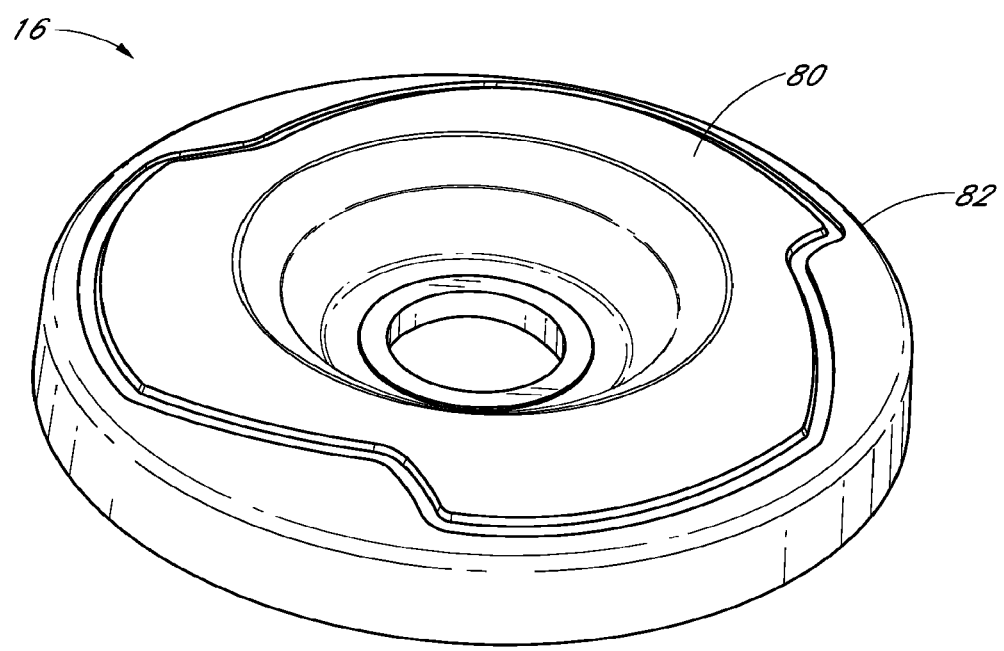
FIG. 18 is a perspective view of the top portion of the embodiment of the knob shown in FIG. 1.
Figure 19:
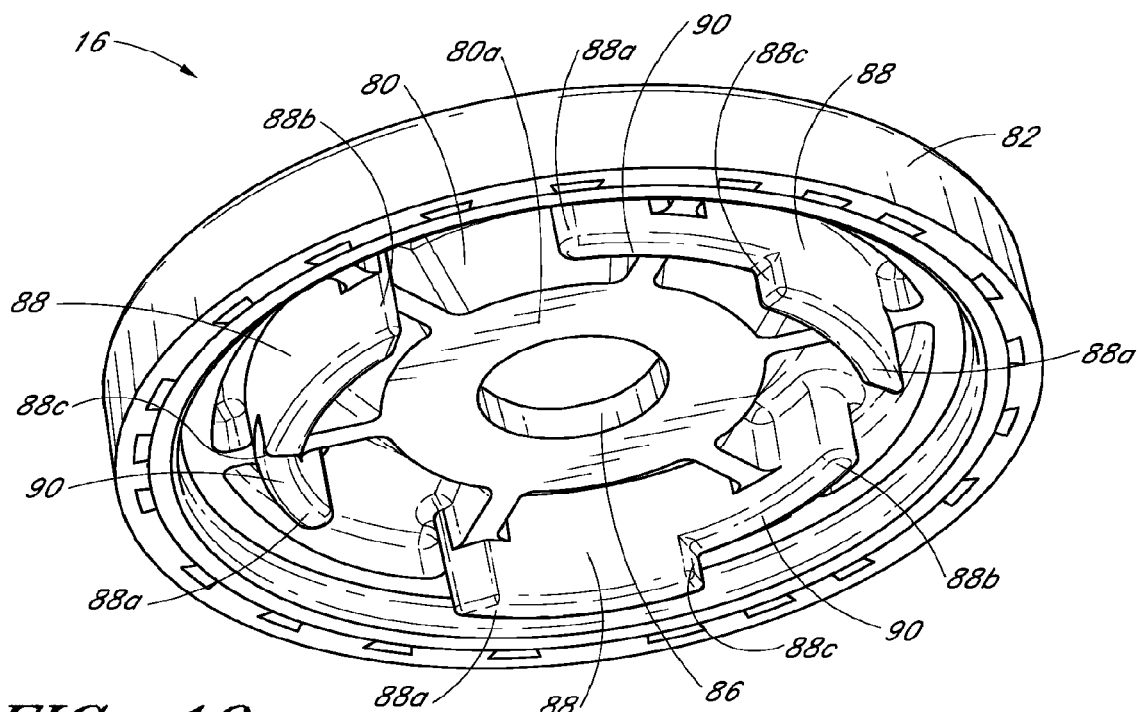
FIG. 19 is a perspective view of the bottom portion of the embodiment of the knob shown in FIG. 1.
Figure 20:
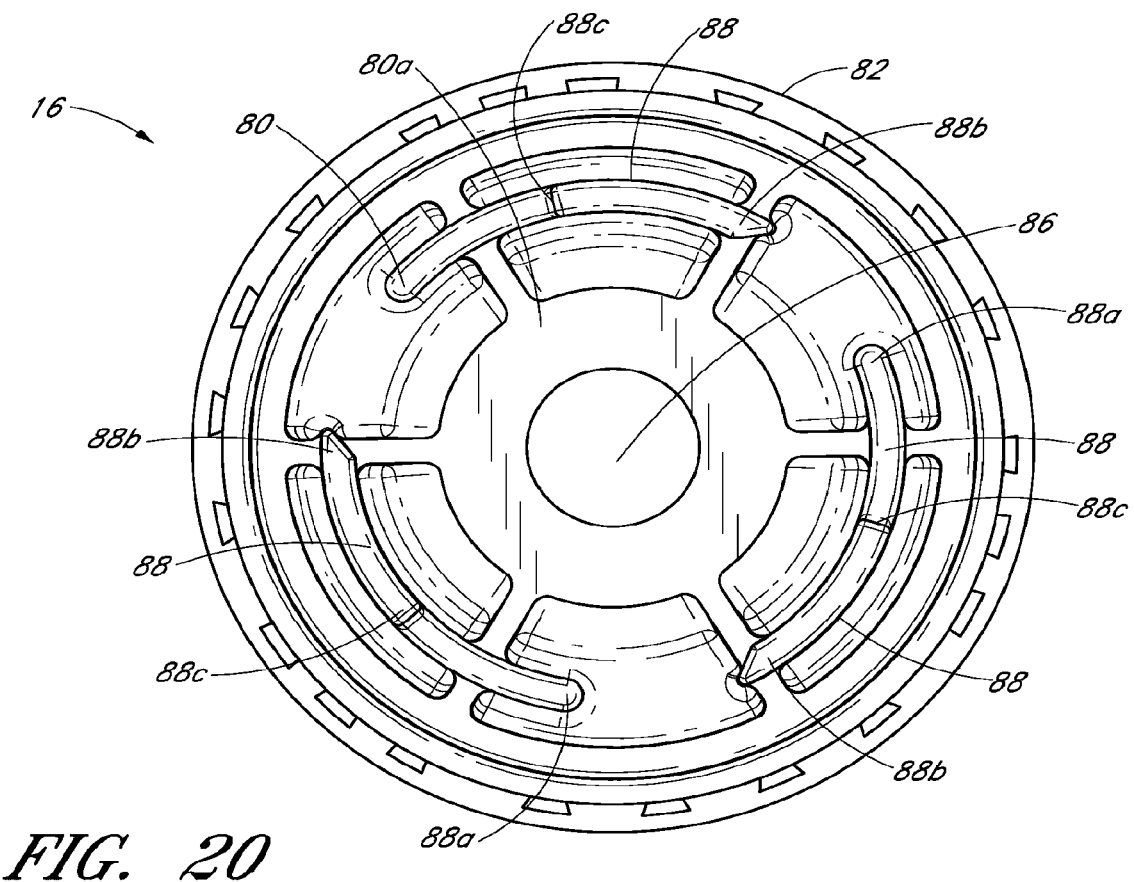
FIG. 20 is a bottom view of the embodiment of the knob shown in FIG. 1.

FIGS. 18-19 are a perspective view of the top and bottom portions, respectively, of the embodiment of the knob 16 shown in FIG. 1. FIG. 20 is a bottom view of the embodiment of the knob 16 shown in FIG. 1. With reference to FIGS. 18-20, in some embodiments, the knob 16 can be formed from a generally rigid body member 80 and can optionally have a rubber overmold or overlay 82 to increase the user's grip of the knob 16.

Figure 21:
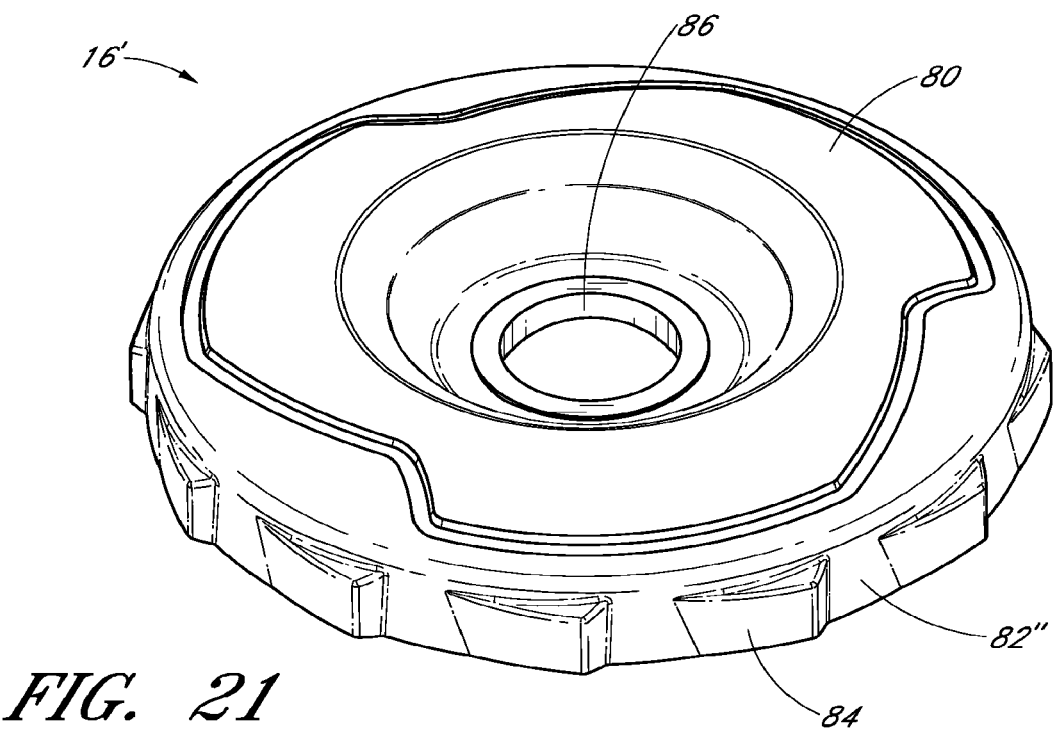
FIG. 21 is a perspective view of another embodiment of a knob that can be used with the embodiment of the lacing system shown in FIG. 1.
Figure 22:
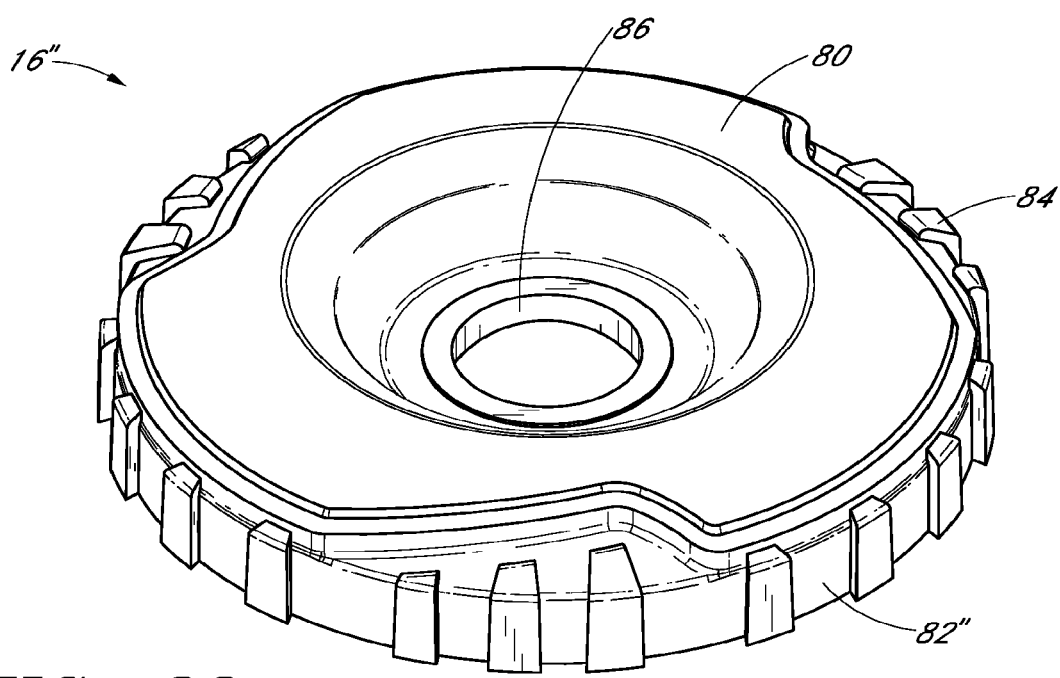
FIG. 22 is a perspective view of yet another embodiment of a knob that can be used with the embodiment of the lacing system shown in FIG. 1.

FIG. 21 is a perspective view of another embodiment of a knob 16' that can be used with the embodiment of the lacing system 10 shown in FIG. 1. FIG. 22 is a perspective view of yet another embodiment of a knob 16" that can be used with the embodiment of the lacing system 10 shown in FIG. 1. With reference to FIGS. 21-22, in some embodiments, each of the knobs 16', 16" can have a generally rigid body member 80 and a rubber overlay 82', 82", respectively, having raised portions 84 configured to increase a user's grip of the knobs 16', 16" or otherwise enhance a user's ability to rotate the knobs 16', 16".

Each of the knobs disclosed herein can have an opening 86 formed in the body member 80 so as to be coaxial with the centerline of the knob 16. The opening 86 can be sized and configured to receive a fastener member, such as the fastener member 18 illustrated in FIG. 1, for coupling the knob 16 to the housing 12. In some embodiments, the lacing system 10, including the housing 12, the spool member 14, the knob 16, and the fastener 18 can be configured so that the spool member 14 and the knob 16 are generally axially coupled to the housing 12 by the fastener 18, while permitting the spool member 14 and the knob 16 to generally rotate freely relative to the housing 12, except as affected by the interaction of the pawls 62 of the spool member 14 with the depressions 40 formed in the housing 12, as described above.

With reference to FIGS. 19-20, the knob 16 can have one or more protrusions or drive members 88 formed on the body member 80 protruding downwardly from the generally planar bottom surface 80a of the body member 80. As most clearly illustrated in FIG. 20, each of the drive members 88 can define a generally arcuate or partially cylindrical shape, with the centerline of the arc or partial cylinder being coaxial with the centerline of the knob 16 and opening 86. Additionally, each of the drive members 88 can define a first end portion 88a and a second end portion 88b. In some embodiments, the geometry and size of the first end portion 88a can be the same as or similar to the geometry and size of the second end portion 88b. However, in some embodiments, as in the illustrated embodiment, the geometry and size of the first end portion 88a can be different as compared to the geometry and size of the second end portion 88b. In particular, with reference to FIG. 20, the first end portion 88a of each drive member 88 can define a generally flat end surface, while the second end portion 88b of each drive member 88 can define a generally angled, planar end surface.

Figure 23:
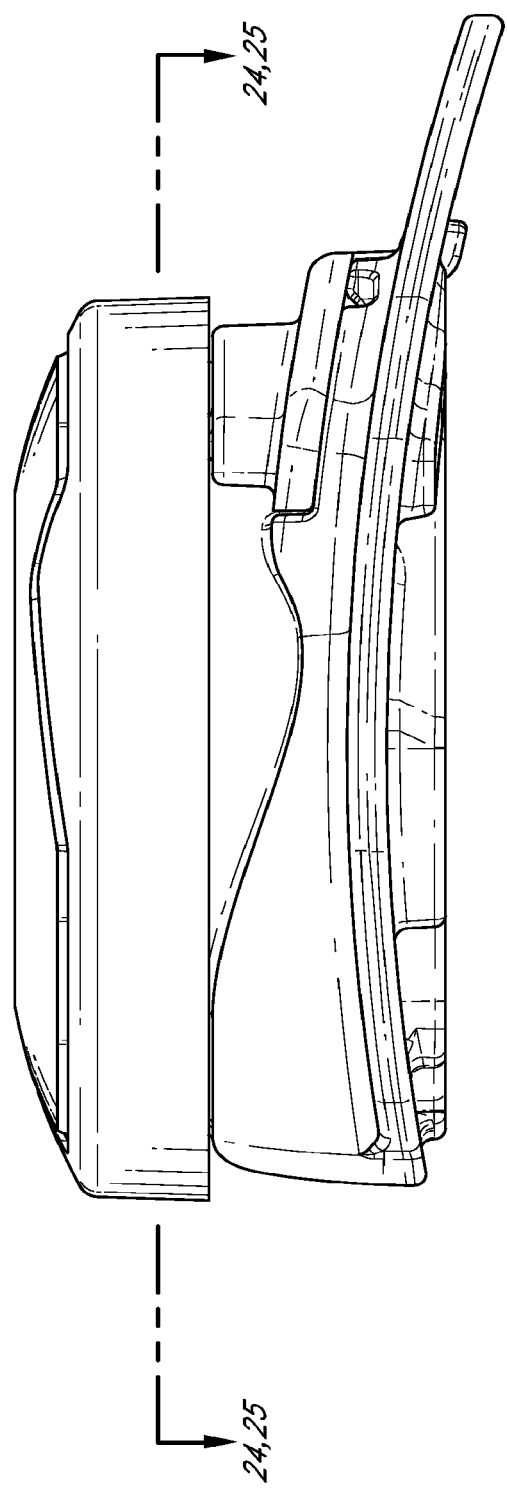
FIG. 23 is a side view of the embodiment of the lacing system shown in FIG. 1.
Figure 24:
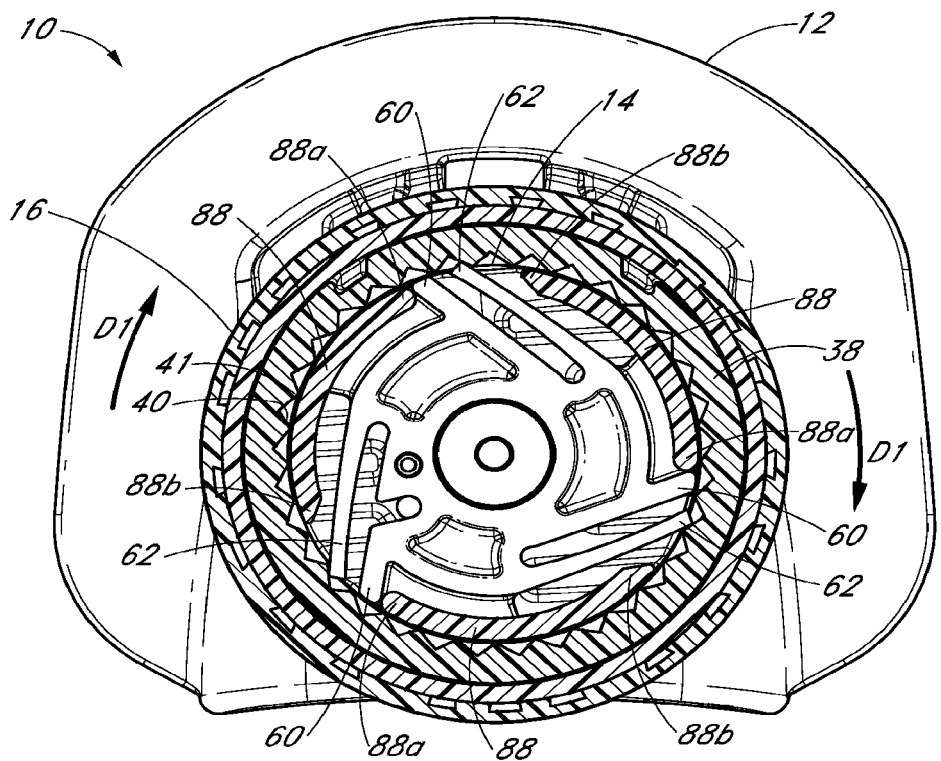
FIG. 24 is a section view of the embodiment of the lacing system shown in FIG. 1, taken through line 24-24 of FIG. 23, showing the lacing system being rotated in a first direction.
Figure 25:
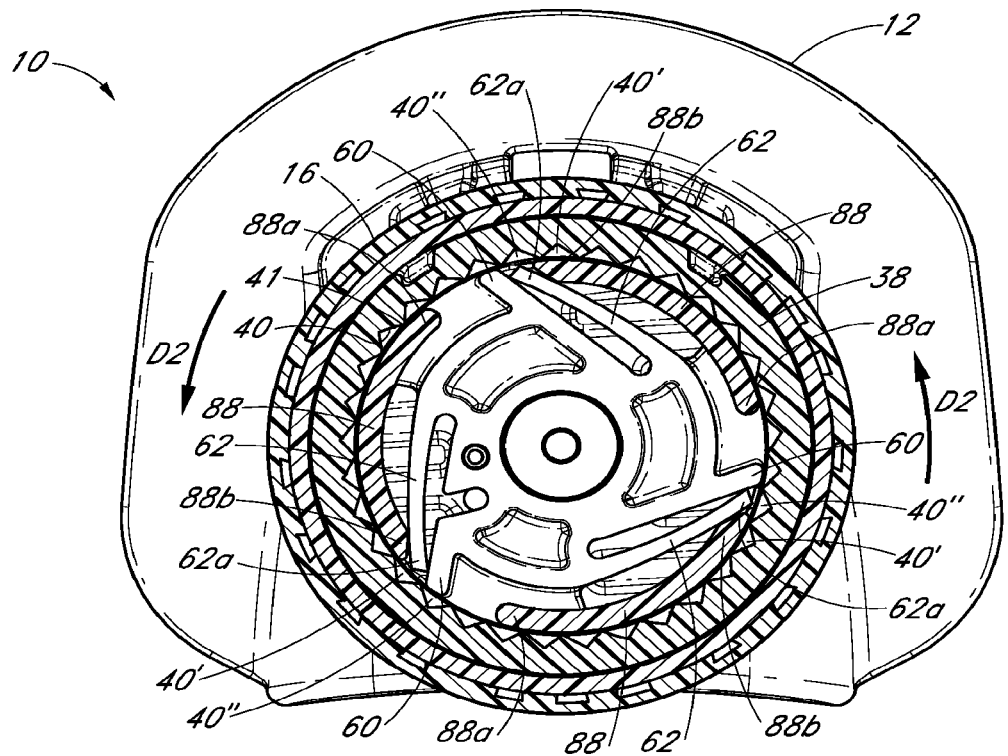
FIG. 25 is a section view of the embodiment of the lacing system shown in FIG. 1, taken through line 25-25 of FIG. 23, showing the lacing system being rotated in a second direction.

FIG. 23 is a side view of the embodiment of the lacing system 10 shown in FIG. 1. FIGS. 24, 25 are section views of the embodiment of the lacing system 10 shown in FIG. 1, taken through lines 24-24 and 25-25, respectively, of FIG. 23. With reference to FIGS. 24-25, the method of rotating the spool member 14 and, hence, tightening or incrementally loosening the lacing system 10, will now be described in greater detail.

FIG. 24 illustrates the interaction between the drive members 88 of the knob 16 with the driven members 60 of the spool member 14, as the spool member 14 is rotated in the first direction (represented by arrow D1 in FIG. 24). In particular, the lacing system 10 can be configured such that, when a user rotates the knob 16 in the first direction D1, the first end portion 88a of each of the drive members 88 formed on the knob 16 can contact each of the driven members 60 formed on the spool member 14 so as to transfer the rotational force from the knob 16 to the spool 14 and, hence, rotate the spool member 14 in the first direction D1. As the spool member 14 is rotated in the first direction D1, each of the pawls 62 formed on the spool member 14 can be bent or deflected away from each of the protrusions or teeth 41 formed in the wall 38 of the housing 12, because the pawls 62 can be sufficiently flexible for such deflection.

When the user stops rotating the knob 16 so as to eliminate the rotational force that the user exerts on the knob 16, the tension created in the tightened lace system 10 can exert a force on the spool member 14 that tends to rotate the spool member 14 in the second, loosening direction D2. The lacing system 10 can be configured to counteract this loosening force. In some embodiments, the lacing system 10 can be configured such that the pawls 62 are engaged by the depressions 40 (as illustrated in FIGS. 14-15) to inhibit or prevent the spool member 14 from rotating in the loosening direction. When the pawls 62 are engaged by the depressions 40, as illustrated in FIGS. 14-15, the spool 14 can be generally prevented from rotating in the loosening direction until the pawls 62 are disengaged from the depressions 40. In some embodiments, the pawls 62 can be disengaged from the depressions 40 by deflecting the end portions 62a of each of the pawls 62 so as to move the end portions 62a of each of the pawls 62 from the depressions 40, as will be described below.

FIG. 25 illustrates the interaction between the drive members 88 of the knob 16 with the driven members 60 of the spool member 14, as the knob 16 and the spool member 14 are rotated in the second direction (represented by arrow D2 in FIG. 25). In particular, the lacing system 10 can be configured such that, when a user rotates the knob 16 in the second direction D2, the second end portion 88b of each of the drive members 88 formed on the knob 16 contacts each of the pawls 62 formed on the spool member 14. As the second end portion 88b of each of the drive members 88 formed on the knob 16 continues to exert a pressure on each of the pawls 62, the end portions 62a of each of the pawls 62 can be deflected from the engaged position with respect to the depressions 40 to a position where the end portions 62a of each of the pawls 62 can be rotated past each of the teeth 41 formed in the housing 12 in the second direction D2, as illustrated in FIG. 25.

If the lacing system 10 is under tension so that the laces 20 exert a rotational force on the spool 14, when end portions 62a of each of the pawls 62 are deflected from the engaged position with respect to the depressions 40, the lacing system 10 can be configured such that the spool 14 rotates in the second direction D2 and such that each of the pawls 62 engages with the next successive depression 40. In other words, with reference to FIG. 25, FIG. 25 represents the position of each of the pawls 62 after each of the pawls 62 has been contacted with each of the drive members 88 so as to disengage each of the drive members from the depressions 40'. If the drive members 88 deflect each of the pawls 62 an amount sufficient for each of the pawls 62 to move past each of the teeth 41 as the tension in the lacing system 10 rotates the spool 14 in the loosening direction D2, the lacing system 10 can be configured such that each of the pawls 62 are biased to move into and be engaged by the next successive depression 40", again inhibiting the rotation of the spool 14 in the loosening direction D2 until the pawls 62 are disengaged from the depressions 40". In this manner, the spool member 14 can be incrementally loosened or released.

In some embodiments, as in the embodiment of the knob 16 illustrated in FIGS. 19-20, each drive member 88 can define a cut-out or notch 90 formed in a portion of the drive member 88. However, such cut out or notch 90 is not required and can be eliminated from some embodiments of the knob 16. In some embodiments, with reference to FIGS. 19-20, the end portion 88c formed by the notch 90 can define the surface that can contact the driven members 60 of the spool member 14 to turn the spool member 14. The size of the notch 90 and, hence, the position of the end portion 88c relative to the end portion 88b, can be configured to provide a desired amount of free-play of the knob 16 relative to the spool member 14.

Due to the orientation of the pawls 62 in the lacing system 10 described above, in some embodiments, the lacing system 10 described above can be configured such that the lacing system can only be tightened if the spool 14 is rotated in a first direction, and can only be loosened if the spool 14 is rotated in a second, opposite direction. Thus, in some embodiments, the spool member 14 can be configured to be unidirectional. Further, the orientation of the pawls 62 and the position of the driven member 60 can be reversed so that the tightening direction of the spool 14 relative to the housing 12 can be reversed. This configuration is also unidirectional because the lacing system can only be tightened by rotating the spool 14 in the second direction, and can only be loosened by rotating the spool 14 in the first direction. However, in some embodiments, described in greater detail below, the lacing system can be configured to have a spool member 14 that is bidirectional, such that the lacing system can be tightened by rotating the spool in either direction D1 or D2.

Figure 26:
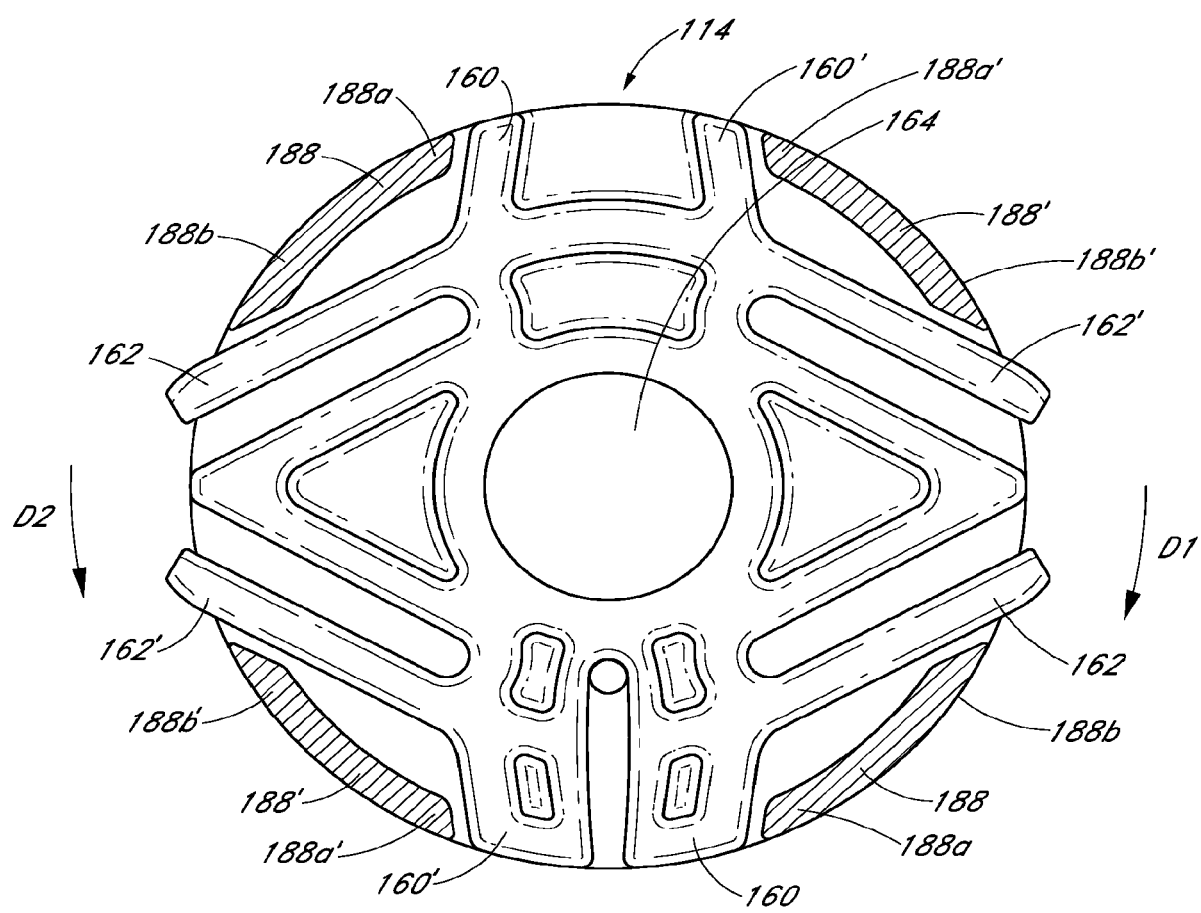
FIG. 26 is a top view of another embodiment of a spool member that can be configured to be used in any of the lacing systems disclosed herein.

FIG. 26 is a top view of another embodiment of a spool member 114 that can be configured to be used in any of the lacing systems disclosed herein. As will be described, the spool member 114 illustrated in FIG. 26 can be used as a bidirectional spool. Any suitable lacing system or any of the lacing systems disclosed herein can be configured for use with the spool number 114 illustrated in FIG. 26. To facilitate the description, portions of a knob member, in particular, four drive members 188, are also illustrated in FIG. 26. The drive members 188 can be configured to be the same as or similar to the drive members 88 described above with respect to knob 16.

The embodiment of the spool member 114 illustrated in FIG. 26 can have a total of four pawls 162, though in alternative embodiments more or less may be used. The pawls 162' can be positioned and configured to engage depressions formed in the housing similar to the housing 12 so as to prevent the spool member 114 from rotating in a first direction represented by arrow D1, in a manner that is similar to the pawls 62 described above. The pawls 162 can be positioned and configured to engage with the depressions formed in the housing (not shown) so as to prevent the spool member 114 from rotating in a second direction represented by arrow D2, also in a manner that is similar to the pawls 62 described above. As will be described below in greater detail, with a bidirectional spool member 114, lace can be gathered by the empty spool 114 by rotating the spool 114 in either direction D1 or D2.

Therefore, in this configuration, to rotate the spool member 114 in the first direction D1, each of the two pawls 162' can be deflected and disengaged by the knob's drive members 188' (in particular, the second end portion 188b' of drive members 188') from the respective depressions that the pawls 162' are engaged with (depressions not illustrated). The spool member 114 can be configured such that, as the pawls 162' are deflected by the knob's drive members 188' (i.e., by turning the knob and, hence, the knob's drive members 188' in a first direction D1), the knob's drive members 188 (in particular, the first end portion 188a of drive members 188) can contact the driven members 160 formed on the spool member 114 so as to cause the spool member 114 to rotate in the first direction D1. In this manner, the spool member 114 can be incrementally rotated in the first direction D1, i.e., the spool member 114 can be rotated in the first direction D1 until each of the two pawls 162' is engaged by the next successive depressions (not illustrated). In some embodiments, each of the two pawls 162 can be configured so as to generally not impede the rotation of the spool member 114 in the first direction D1, such as by bending and displacing away from the depressions. However, as will be described, each of the two pawls 162 can be configured to generally prevent or impede the rotation of the spool member 114 in a second direction D2.

Similarly, in this configuration, to rotate the spool member 114 in the second direction D2, each of the two pawls 162 can be deflected and disengaged by the knob's drive members 188 (in particular, the second end portion 188b of the drive members 188) from the respective depressions (not shown) that the pawls 162 are engaged with. The spool member 114 can be configured such that, as the pawls 162 are deflected by the knob's drive members 188 (i.e., by turning the knob and, hence, the knob's drive members 188, in a second direction D2), the knob's drive members 188' can contact the driven members 160' formed on the spool member 114 so as to cause the spool member 114 to rotate in the second direction D2. In this manner, the spool member 114 can be incrementally rotated in the second direction D2, i.e., the spool member 114 can be rotated in the second direction D2 until each of the two pawls 162 is engaged by the next successive depressions (not illustrated). In some embodiments, each of the two pawls 162' can be configured so as to generally not impede the rotation of the spool member 114 in the second direction D2.

Figure 27:
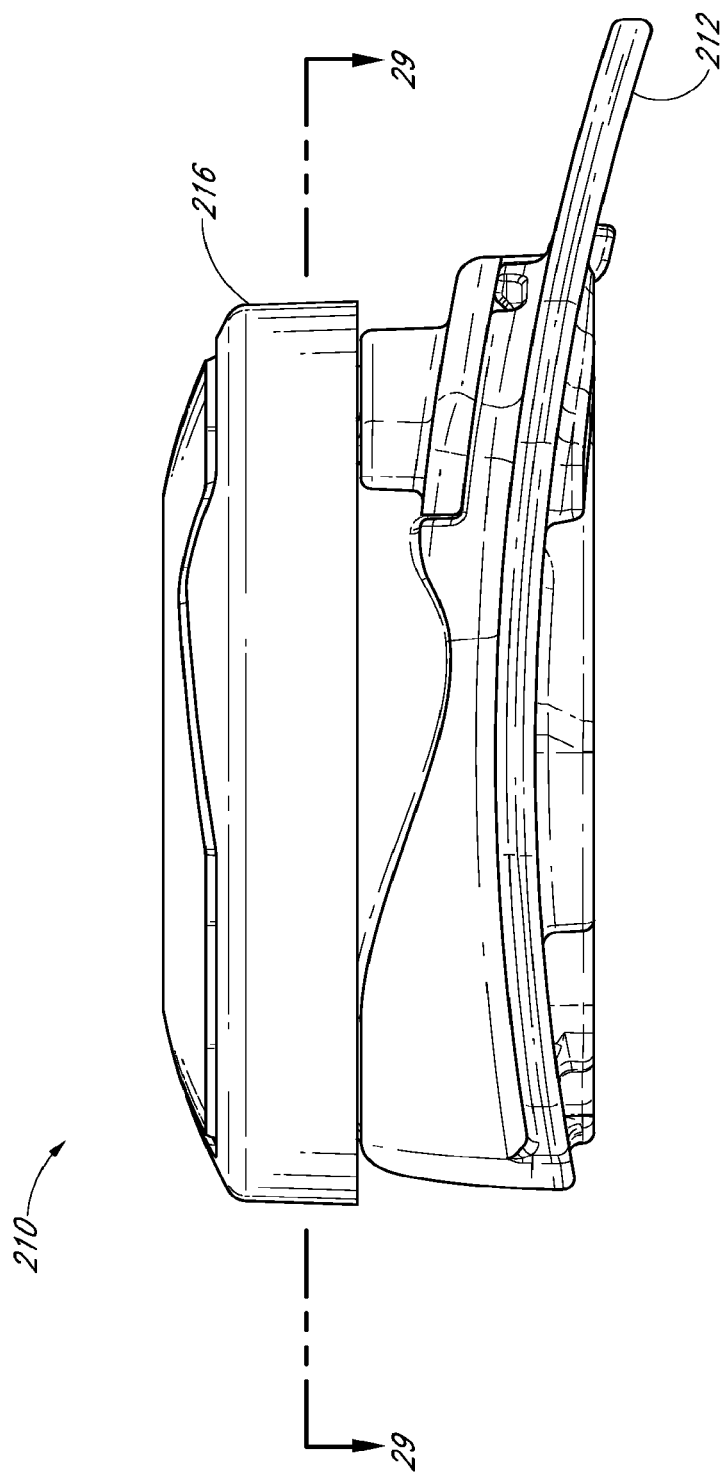
FIG. 27 is a side view of another embodiment of a reel based lacing system, having the embodiment of the spool member illustrated in FIG. 26.
Figure 28:
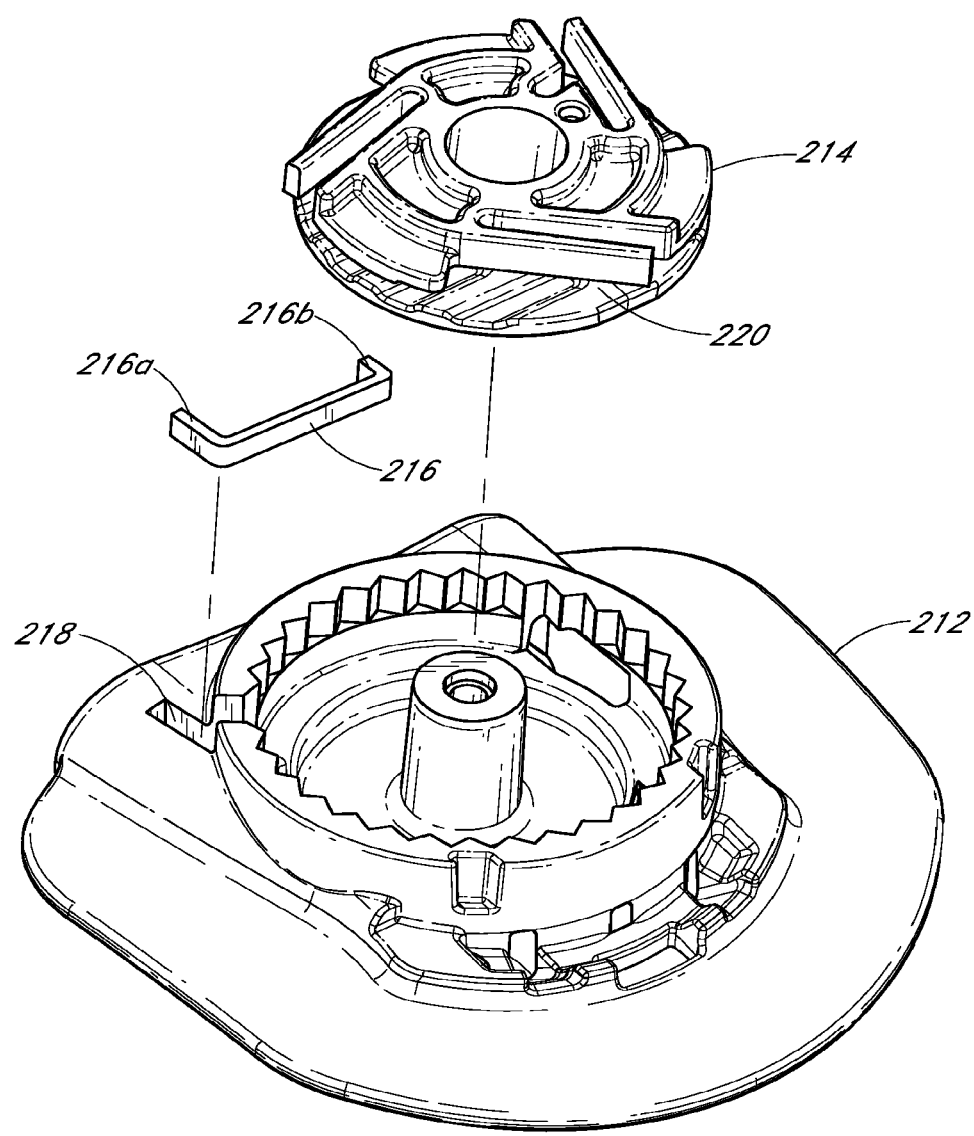
FIG. 28 is an exploded perspective view of some of the components of the lacing system shown in FIG. 27.
Figure 29:
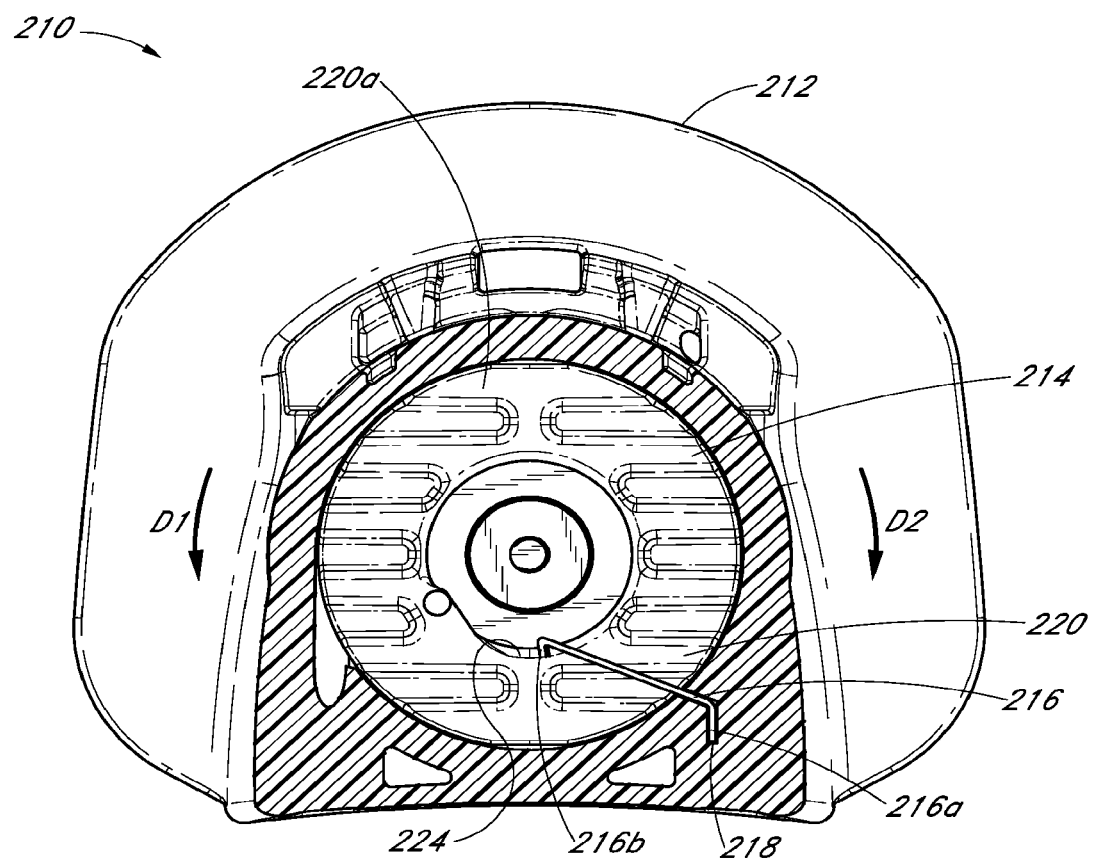
FIG. 29 is a section view of the embodiment of the lacing system shown in FIG. 27, taken through line 29-29 FIG. 27.

FIG. 27 is a side view of another embodiment of a reel based lacing system 210. FIG. 28 is an exploded perspective view of an embodiment of a housing 212, the spool member 214, and spring member 216 of the lacing system 210 shown in FIG. 27. FIG. 29 is a section view of the embodiment of the lacing system shown in FIG. 27, taken through line 29-29 FIG. 27. Any of the components of the lacing system 210 can be the same or similar to any of the components of any of the other lacing systems described herein, or can have any of the features or distinctions described below. Additionally, any of the lacing systems described herein can be configured to have any of the components or features of the lacing system 210 described below.

In particular, with reference to FIGS. 28-29, the housing 212 of the lacing system 210 can be can figured to define an opening or channel 218 configured to receive the spring member 216. As will be described, the lace system 210 can be configured so that the spring member 216 substantially prevents the spool member 214 from rotating in a second direction (represented by arrow D2) when no lace has yet been gathered by the spool member 214. This can be useful for unidirectional spools or lace systems to prevent a user from winding lace on the spool in the wrong direction (i.e., the direction that cannot counteract the force exerted on the spool by the tension from a tightened lacing system).

As illustrated in FIG. 29, the spring member 216 can be assembled with the spool member 214 and the housing 212 so that a first portion 216a of the spring member 216 can be received within the channel 218 that can be formed in the housing 212 and so that a second portion 216b of the spring member 216 can be received within the lace gathering channel 220 formed in the spool member 214. As with the other lace systems described herein, the channel 220 can be configured to define an approximately semicircular, "C" shaped, or "U" shaped cross-section, and can be sized and configured to gather a single or double level of lace (not illustrated) therein, or otherwise.

FIG. 29 illustrates a configuration wherein the spring member 216 has been assembled with the housing 212 such that the first end portion 216a of the spring member is received within the channel 218 of the housing 212 and a second portion 216b of the spring member 216 has been positioned within the channel 220 formed in the spool member 214. FIG. 29 illustrates the lacing system 210 before any lace has been gathered in the channel 220 of the spool member 214. Before any lace has been gathered in the channel 220 of the spool member, the spring member 216 can be biased to move towards the inner surface 220b of the channel 220 such that the second end portion 216b of the spring member 216 is biased to move into and engage with the channel or cutout 224 formed in the spool member 214. In some embodiments, the cutout 224 is formed on an inner surface 220b of the channel 220.

When the second end portion 216b of the spring member 216 is engaged with the cutout 224 (i.e., before any lace has been gathered in the channel 220 formed in the spool 214), the lacing system 210 can be configured such that the second end portion 216b of the spring member 216 engages with the cutout 224 so as to substantially prevent the spool member 214 from rotating in the second direction D2, while not substantially preventing or impeding the spool member 214 from rotating in the first direction D1. In particular, the second portion 216b of the spring member 216 can be configured to slide relative to the cutout 224 when the spool 214 is rotated in the first direction D1. Similarly, the second portion 216b of the spring member 216 can be configured to engage with teeth, tabs, protrusions, holes, or other features formed in the cutout 224 to prevent the spool 214 from rotating in the second direction D2 before any lace has been gathered in the channel 220 of the spool 214.

However, in some embodiments, the lacing system 210 can be configured such that, when lace is gathered in the channel 220 of the spool 214 by winding the spool 214 in the first direction D1, the lace (not illustrated) can gather against the inner surface 220b of the channel 220, causing the spring member 216 to deflect so that the second portion 216b of the spring member 216 is not able to engage with the cutout 224 formed in the spool 214. In this arrangement, with the second portion 216b of the spring member 216 deflected away from the cutout 224, in the user can then rotate the spool 214 in the second direction D2 without obstruction from the spring member 216 until all of the lace has been unwound from the spool member 214, at which time the bias of the second portion 216b of the spring member 216 can cause the second portion 216b of the spring member 216 to engage with the cutout 224. In some embodiments, the spring member 216 can be biased against a different portion of the spool, for example the bottom surface 220a to substantially prevent accidental winding in the reverse direction. In some embodiments, the fixed and moveable ends of the spring member 216 are reversed. As such, the spring member 216 could be fixed to the spool 214 and selectively engageable with a portion of the housing 212.

Figure 30:
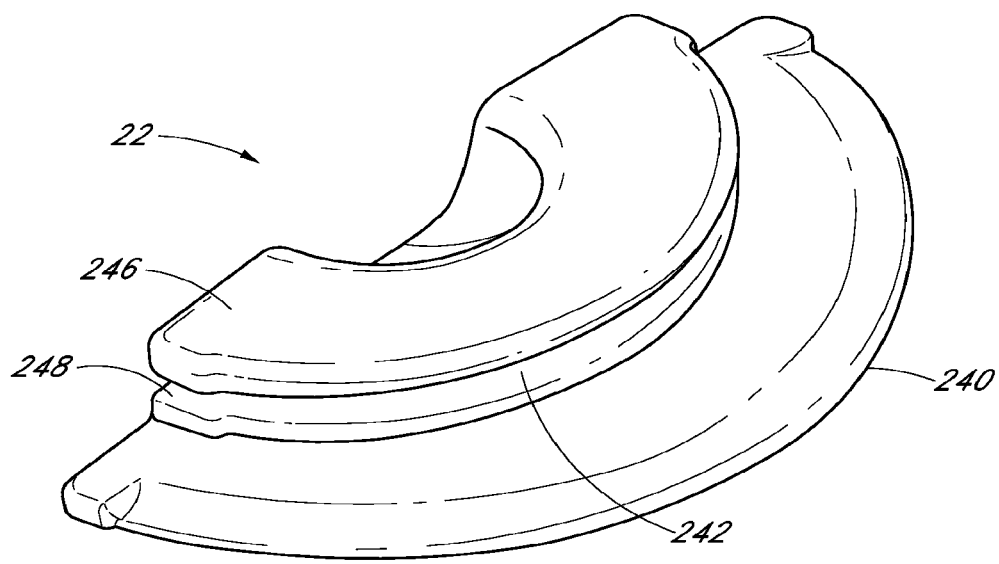
FIG. 30 is a perspective view the embodiment of the guide member illustrated in FIG. 1.
Figure 31:
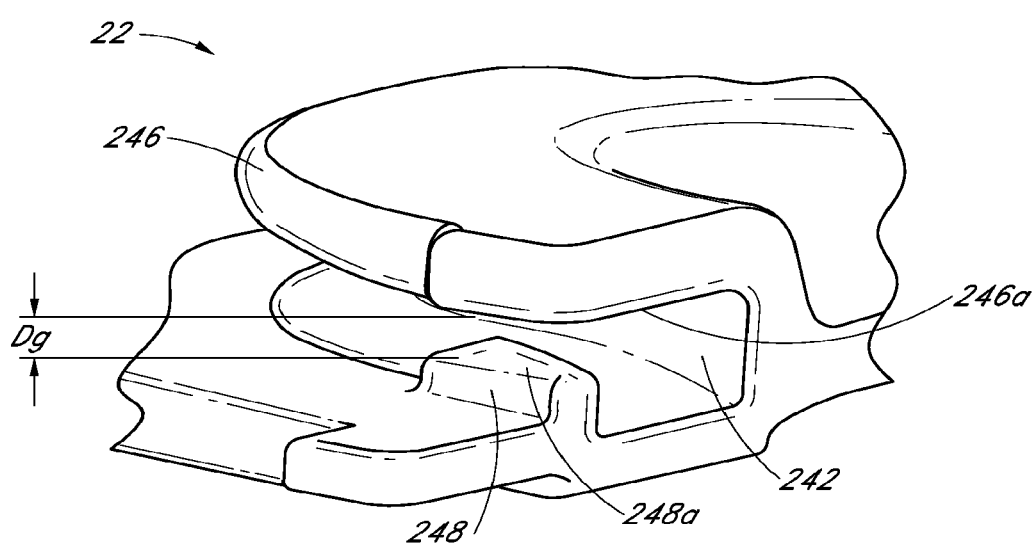
FIG. 31 is an enlarged perspective view of a portion of the guide member illustrated in FIG. 1.

FIG. 30 is a perspective view the embodiment of the guide member 22 illustrated in FIG. 1. FIG. 31 is an enlarged perspective view of a portion of the guide member 22 illustrated in FIG. 1. The guide member 22 can have a mounting flange 240 that can be configured to permit the guide member 22 to be attached to the sport shoe illustrated in FIG. 2. The mounting flange 240 can be configured in accordance with the desired mounting method or mounting fasteners, the contour shape of the sport shoe or other object to which it is to be fastened, the performance characteristics of the lacing system, or other factors. For example, in some embodiments, the mounting flange 240 can be curved to facilitate attaching the guide member 22 to a curved surface of the sport shoe or other objects to which the guide member 22 can be mounted. Additionally, as mentioned, the mounting flange 240 can be sized and configured to accommodate stitching, rivets, or any other suitable or desired fasteners or fastening method to fasten the guide member 22 to the desired object.

In some embodiments, the guide member 22 or any other guide members described herein can be configured so as to be mountable to the sport shoe or other object without the existence or use of the flange 240. For example, in some embodiments (not shown), when the guide member 22 does not have a flange 240, screws or other fasteners can be used to mount the guide member 22 to the sport shoe or other desired object by threading into a bottom surface of the guide member 22.

Additionally, with reference to FIGS. 30-31, a channel 242 can be formed in the guide member 22 to receive lace that has been inserted into the channel 242. As is illustrated, the channel 242 can have an approximately semicircular, "C" shaped, or "U" shaped cross-section, or any other suitable cross-section. To facilitate the tightening of lace in the lacing system, a guide member 22 or guide members 22, if more than one, can be configured so that lace easily slides along the channel 242 formed in each of the guide members 22 as the lace is being tightened. As illustrated in FIGS. 30-31, the guide member 22 can have an upper flange 246 to prevent the lace (not illustrated) from becoming inadvertently disengaged with the channel 242. Additionally, as most clearly illustrated in FIG. 31, the guide member 22 can define one or more guides 248 also configured to retain the lace (not illustrated) within the channel 242.

In some embodiments, the guide member 22 can be configured such that the distance between the upper surface 248a of the guide 248 and the lower surface 246a of the upper flange 246 (this distance being represented by Dg in FIG. 31) is generally less than the thickness or diameter defined by the lace (not shown) received by the channel 242. In this configuration, the lace (not illustrated) could be inserted into the channel 242 by forcing or squeezing the lace through the space between the guide 248 and the upper flange 246 so that lace is biased to remain positioned within at least a portion of the channel 242 during operation of the lacing system. The lace can be removed in a similar fashion.

Figure 32:
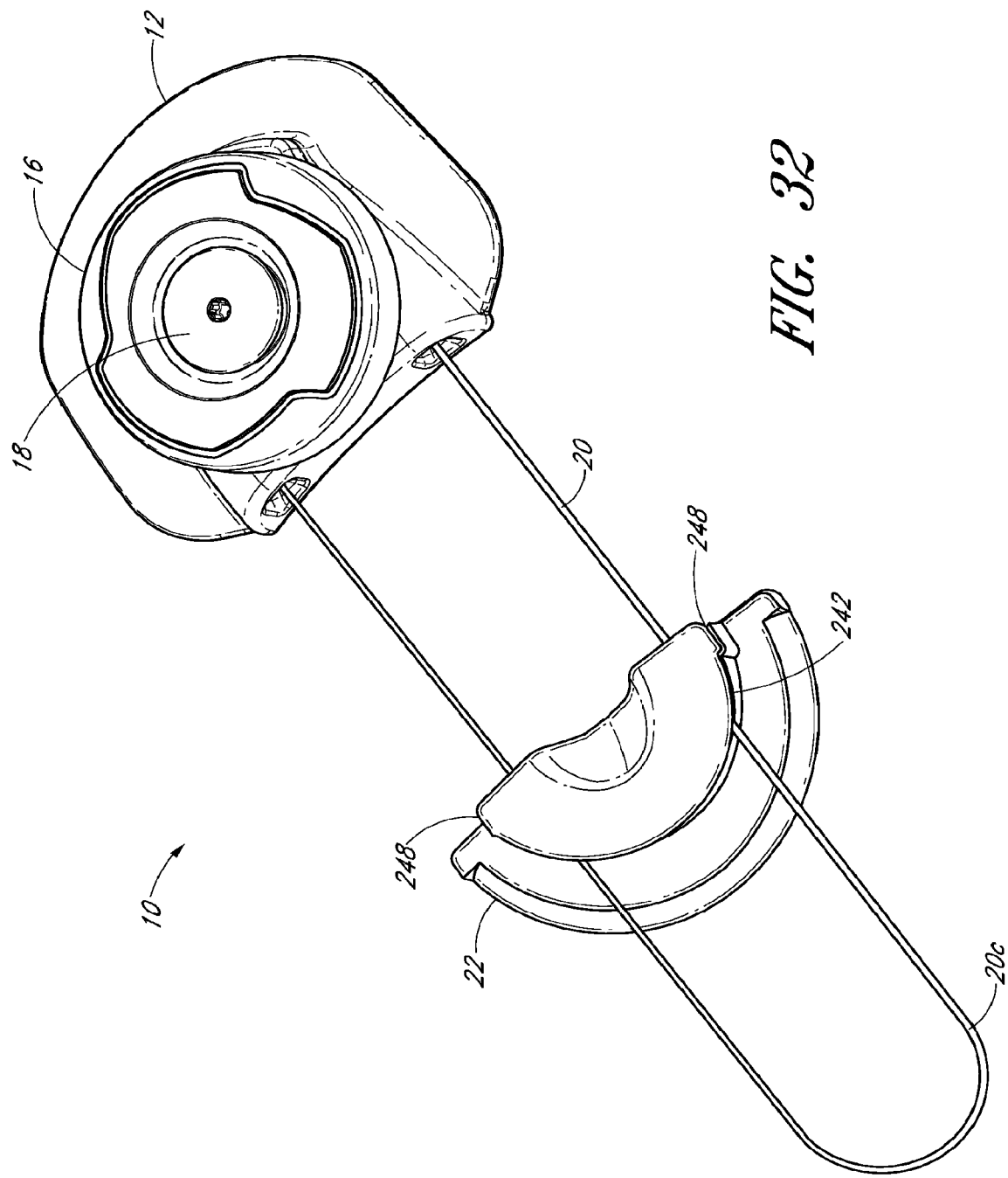
FIG. 32 is a perspective view of the embodiment of the lacing system illustrated in FIG. 1, showing the lace in a loosened state.

Additionally, in this configuration, as the guides 248 can bias the lace to remain positioned within at least a portion of the channel 242, a loop of lace can be formed to facilitate a user's loosening of the lace 20. For example, with reference to FIG. 32, which is a perspective view of the embodiment of the lacing system 10 illustrated in FIG. 1, showing the lace 20 in a loosened state, because the guides 248 can retain the lace 20 within that portion of the channel 242, as the lace 20 is loosened from the spool (not shown), the lace 20 can form a loop 20c which the user can grasp to facilitate further loosening of the lacing system 10. Additionally, the guide 22 can be configured such that a user can grasp the portion of the lace 20 that spans over the shoe or other object (i.e., the portion of the lace 20 that has not yet passed through the guide 22) and withdraw the lace 20 from the guide 22 by pulling the lace 20 laterally through the opening formed between the upper surface 248a of the guide 248 and the lower surface 246a of the upper flange 246 (this distance being represented by Dg in FIG. 31).

Figure 33:
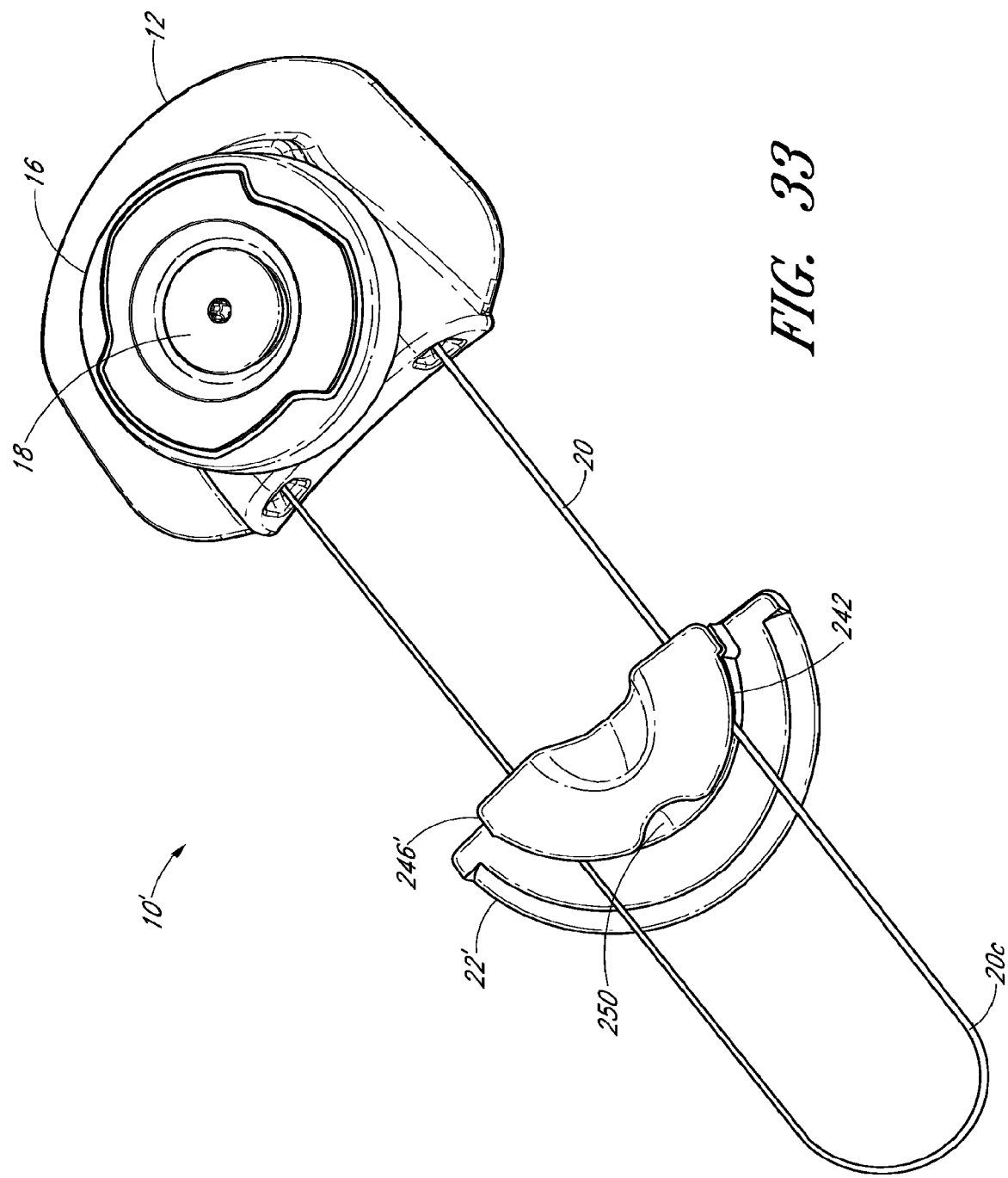
FIG. 33 is a perspective view of the embodiment of the lacing system illustrated in FIG. 32, having a modified guide member.

In some configurations, the guide member 22 can be configured to define a cutout or other features to assist the user in grasping the lace with his or her fingers. One example of a cutout to assist the user in grasping the lace is illustrated in FIG. 33, which is a perspective view of another embodiment of a lacing system 10' that can be similar to the lacing system 10 illustrated in FIG. 32, except having a modified guide member 22'. With reference to FIG. 33 the modified guide member 22' can have a cutout 250 formed in the upper flange 246' so that the user can more easily grasp the looped portion of the lace 20c from the channel 242 formed in the guide member 22'.

Figure 34:
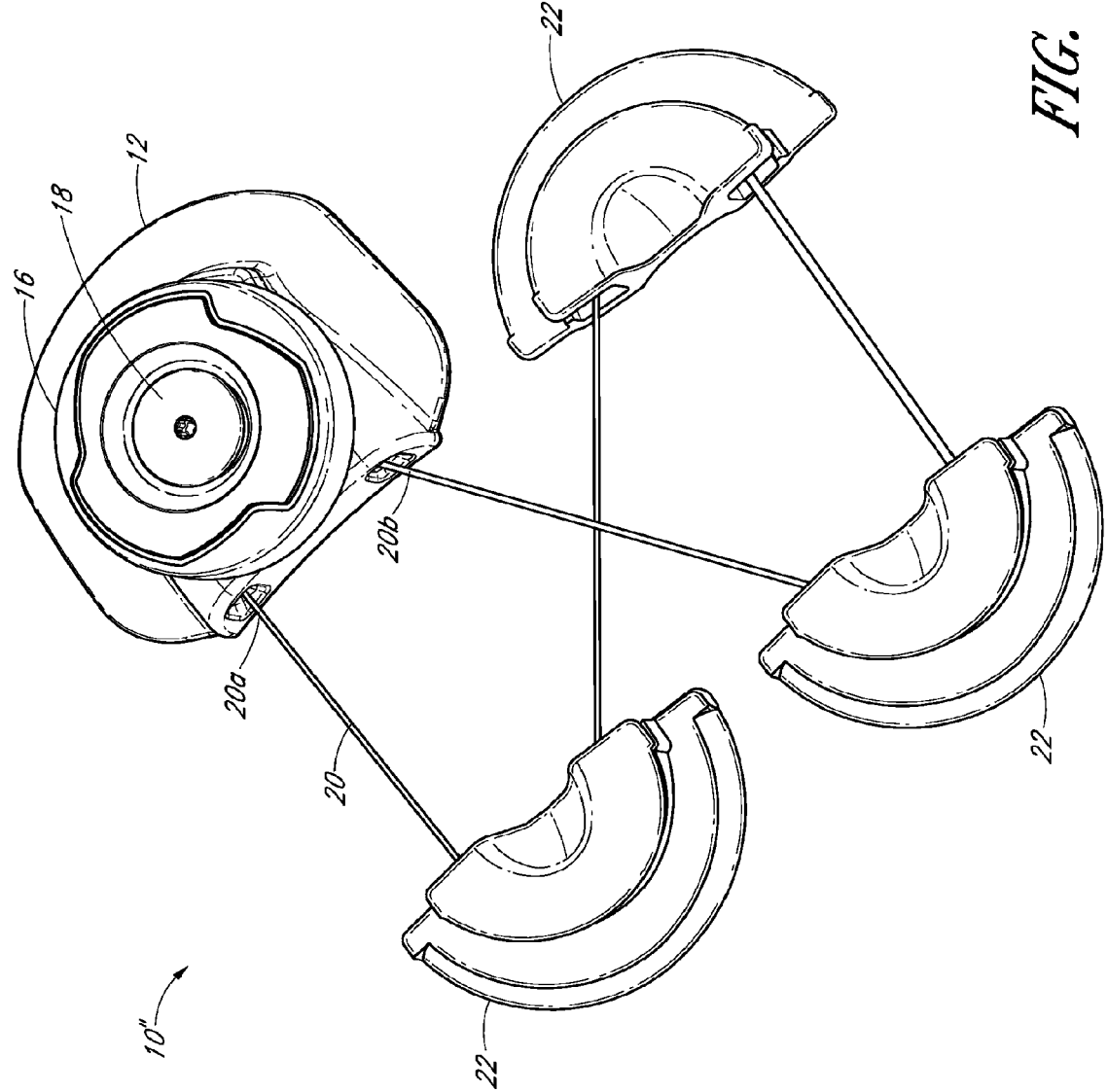
FIG. 34 is a perspective view of another embodiment of a lacing system, having multiple guide members.

FIG. 34 is a perspective view of another embodiment of a lacing system 10", having multiple guide members 22. As illustrated in FIG. 34, the lace 20 can be routed through at least three separate guide members 22. In some embodiments, a first end 20a of the lace can be fixed to the housing 12, while the second end 20b of the lace 20 can be fixed to the spool (not shown) so that the second end 20b of the lace 20 can be wound up by the spool. In some embodiments, a second end 20b of the lace can be fixed to the housing 12, while the first end 20a of the lace 20 can be fixed to the spool (not shown) so that the first end 20a of the lace 20 can be wound up by the spool. Any number or configuration of guide members 22 can be used depending on the desired application of and configuration of the lacing system.

Figure 35:
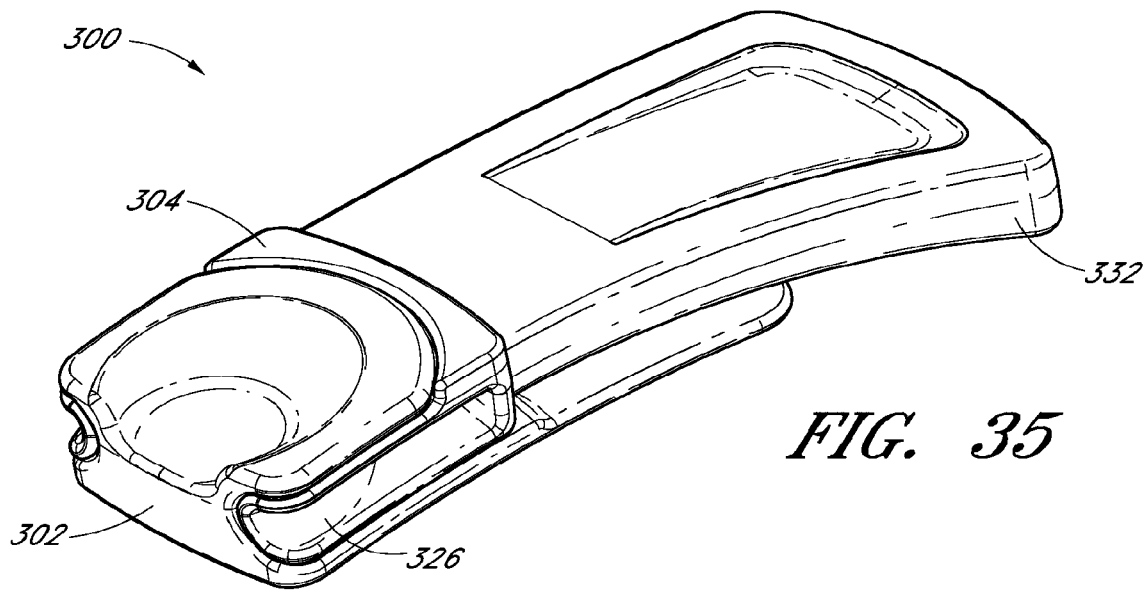
FIG. 35 is a perspective view of an embodiment of a guide member assembly.
Figure 36:
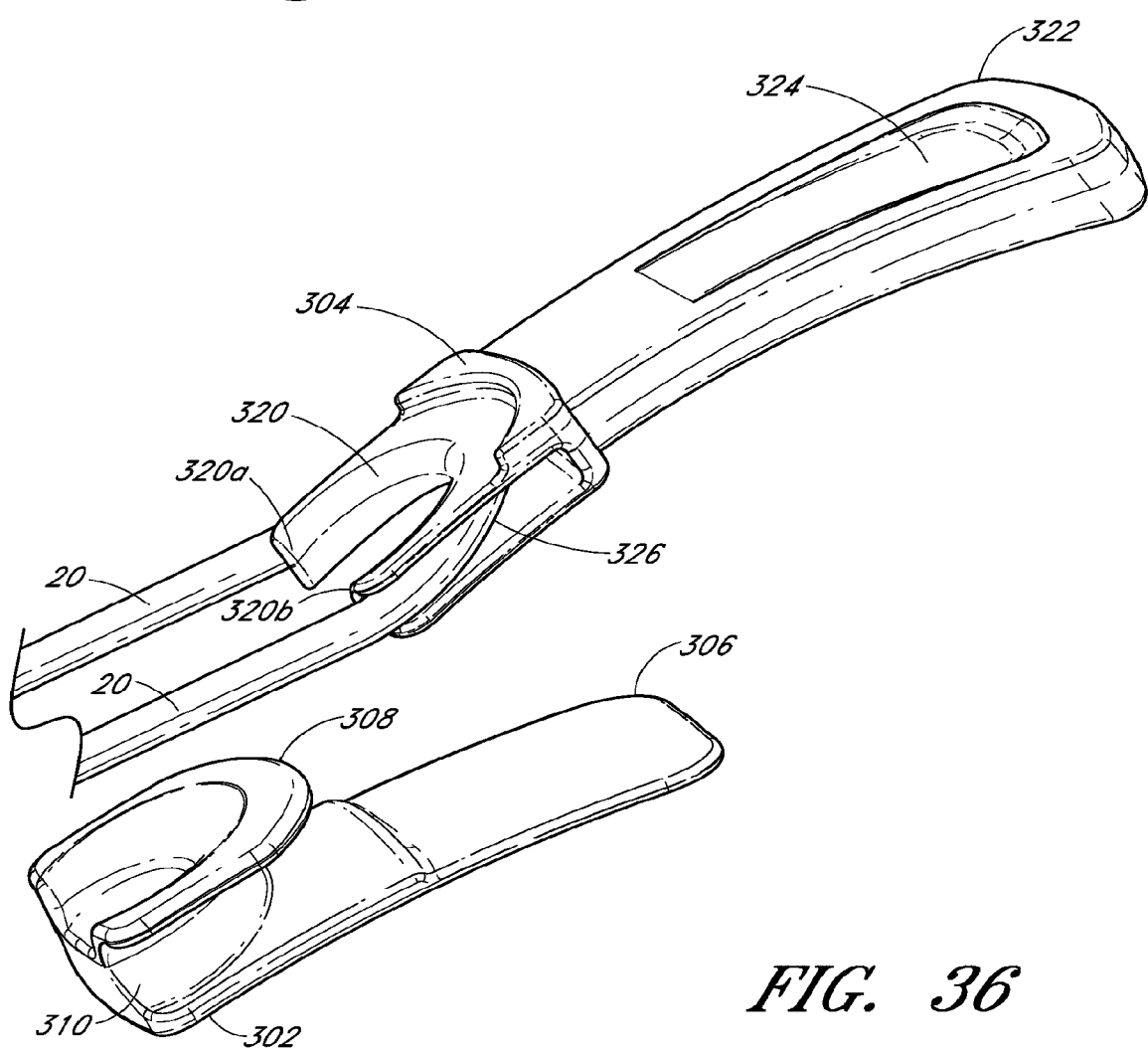
FIG. 36 is a perspective view of the partially exploded assembly comprising the embodiment of the guide member assembly shown in FIG. 35.

In some embodiments, the lacing system can be configured to permit the user to quickly and easily increase or reduce the tension of the lacing system by, for example, temporarily attaching and removing a portion of a guide member through which the lace of the lacing system is routed. An example of one such configuration is described below with reference to FIGS. 35-36. FIG. 35 is a perspective view of an embodiment of a guide member assembly 300. FIG. 36 is a perspective view of the partially exploded assembly comprising the embodiment of the guide member assembly 300 shown in FIG. 35. With reference to FIGS. 35-36, the embodiment of the guide member 300 illustrated therein can comprise a base member 302 and a tab member 304. In some embodiments, the base member 302 can have a mounting flange 306, an upper flange 308, and a channel 310.

In some embodiments, the mounting flange 306 can be configured to permit the base member 302 to be attached to the sport shoe. The mounting flange 306 can be configured in accordance with the desired mounting method or mounting fasteners, the contour shape of the sport shoe or other object to which it is to be fastened, the performance characteristics of the lacing system, or other factors. For example, in some embodiments, the mounting flange 308 can be curved to facilitate attaching the base member 302 to a curved surface of the sport shoe or other object to which the base member 302 can be mounted. The mounting flange 308 can be sized and configured to accommodate stitching, rivets, or any other suitable or desired fasteners or fastening method to fasten the base member 302 to the desired object.

In some embodiments, the base member 302 can be configured so as to be mountable to the sport shoe or other object without the existence or use of the flange 306. For example, in some embodiments (not shown), when the base member 302 does not have a flange 306, screws or other fasteners can be used to mount the base member 302 to the sport shoe or other desired object by threading into a bottom surface of the base member 302.

In some embodiments, the upper flange 308 and the channel 310 can be configured to receive and removably secure the coupling portion 320 of the tab member 304. The coupling portion 320 can be configured to define an outer surface that is similar to and complements the inner surface of the channel 310. Additionally, the upper flange 308, the channel 310, and/or the coupling portion 320 can be configured such that tab member 304 resists or is biased against separation from the base member 302 once tab member 304 is coupled with a base member 302 as illustrated in FIG. 35. For example, in some embodiments, the coupling portion 320 can define a first point 320a and a second point 320b separated by a distance that is narrower than the widest width of the channel 310 so that the first and second points 320a, 320b of the coupling portion 320 must be deflected outwardly in order to be engaged with the channel 310. After the tab member 304 has been coupled with the base member 302 such that the coupling portion 320 is positioned adjacent to the channel 310, the first and second points 320a, 320b can thus inhibit the inadvertent removal or decoupling of the tab member 304 from the base member 302. Additionally, as the laces 20 are put in tension by tightening the lacing system, the laces 20 can also exert a force on the tab member 304 to prevent a tab member 304 from becoming decoupled from the base member 302.

With continued reference to FIGS. 35-36, in some embodiments, the tab member 304 can define a gripping portion 322 that can be over-molded onto, adhered to, or otherwise affixed to or supported by the coupling portion 320. The gripping portion 322 can be formed from a pliable rubber or webbing, a loop of cable, or any other suitable material. The gripping portion 322 can have features that assist the user in maintaining a grip on the gripping portion 322 such as, but not limited to, dimples, protrusions, channels, depressions such as the depression 324 illustrated in FIG. 36, or any other suitable features to enhance the gripability of the gripping portion 322. Additionally, the tab member 302 can define a channel 326 configured to receive lace 20. The channel 326 can be configured such that lace 20 can easily slide through the channel 326 during tightening and loosening of the lacing system.

In some embodiments, a lacing system can include a rotation limiter that can restrict the amount that the spool can be rotated with respect the housing. In some embodiments, the rotation limiter can restrict rotation of the spool in both a clockwise direction and a counter-clockwise direction. In some embodiments, the rotation limiter can allow for a predetermined amount of spool rotation between the furthest clockwise position and the furthest counter-clockwise position. For example, if the spool begins at the position where the rotation limiter prevents further rotation in the clockwise direction, the spool can then be rotated in the counter-clockwise direction by approximately four, or six, or some other predetermined number of revolutions with respect to the housing before the rotation limiter "locks" the spool against further rotation in the counter-clockwise direction. Thus, the rotation limiter can restrict the spool to a predetermined rotation range.

Figure 37:
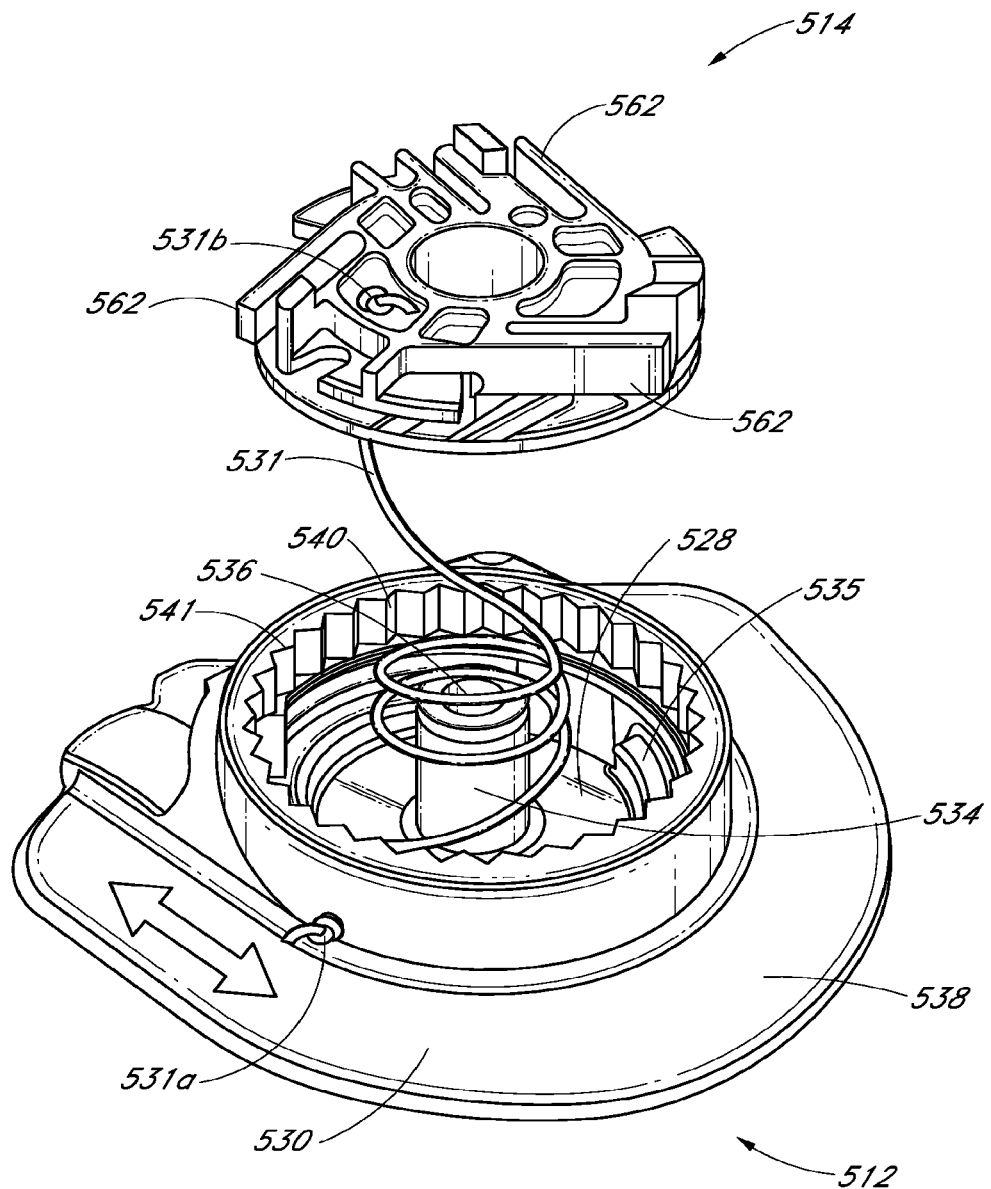
FIG. 37 is an exploded perspective view of certain elements of another embodiment of a lacing system.
Figure 38:
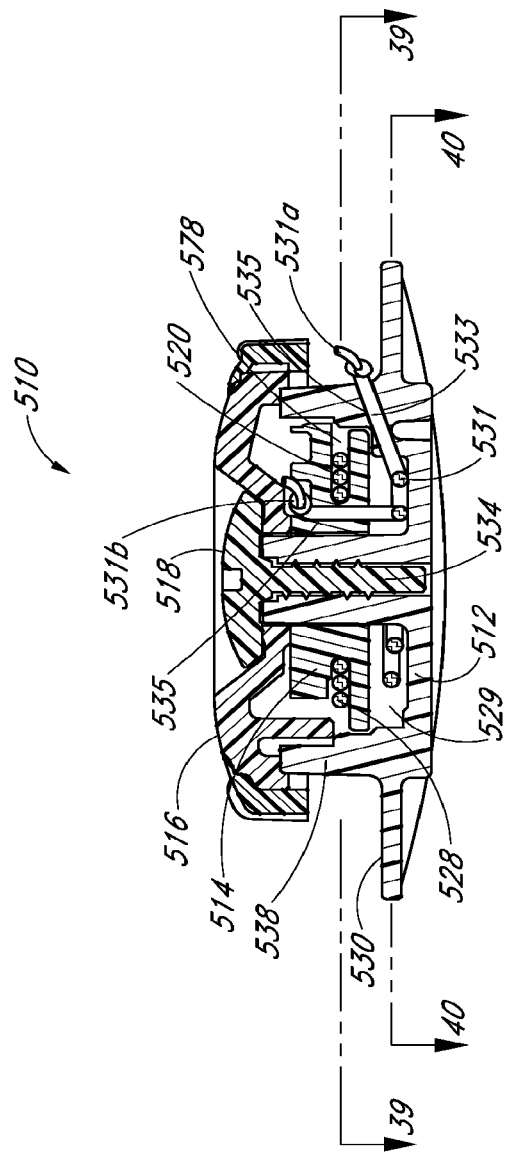
FIG. 38 is a section view of the lacing system illustrated in FIG. 37.
Figure 39:
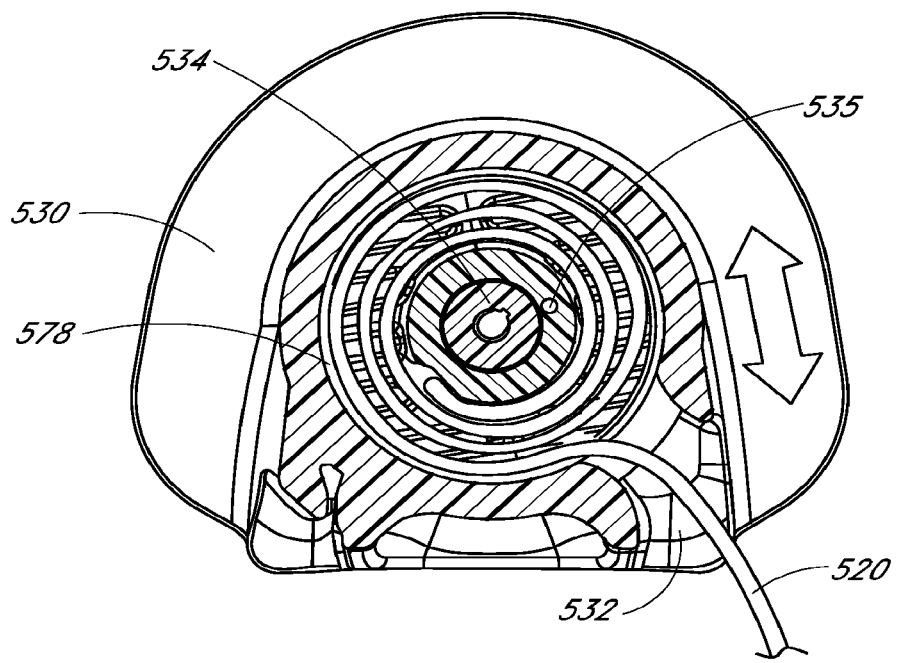
FIG. 39 is a section view of the lacing system illustrated in FIG. 38 taken along the line 39-39.
Figure 40:
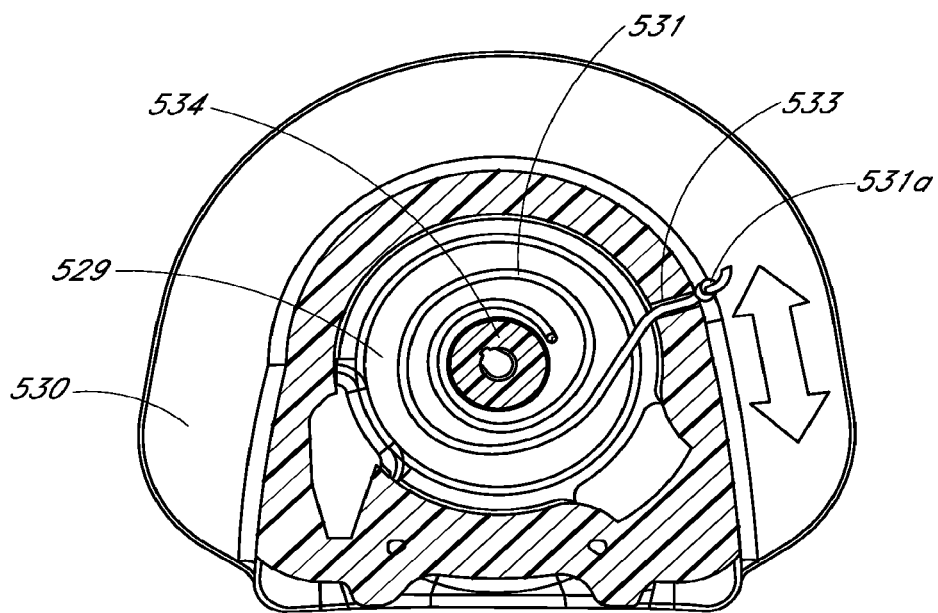
FIG. 40 is a section view of the lacing system illustrated in FIG. 38 taken along the line 40-40.
Figure 41:
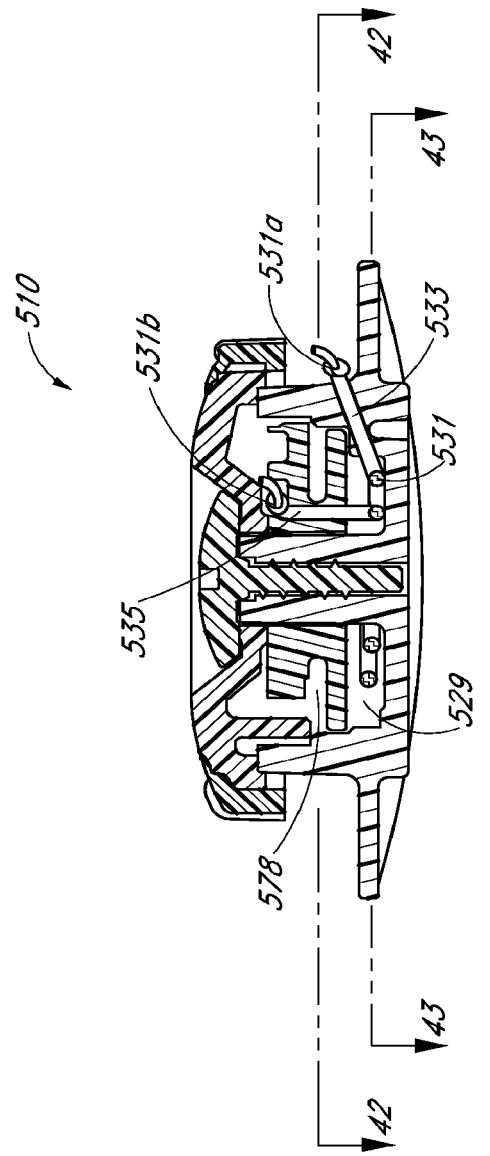
FIG. 41 is another section view of the lacing system illustrated in FIG. 37.
Figure 42:
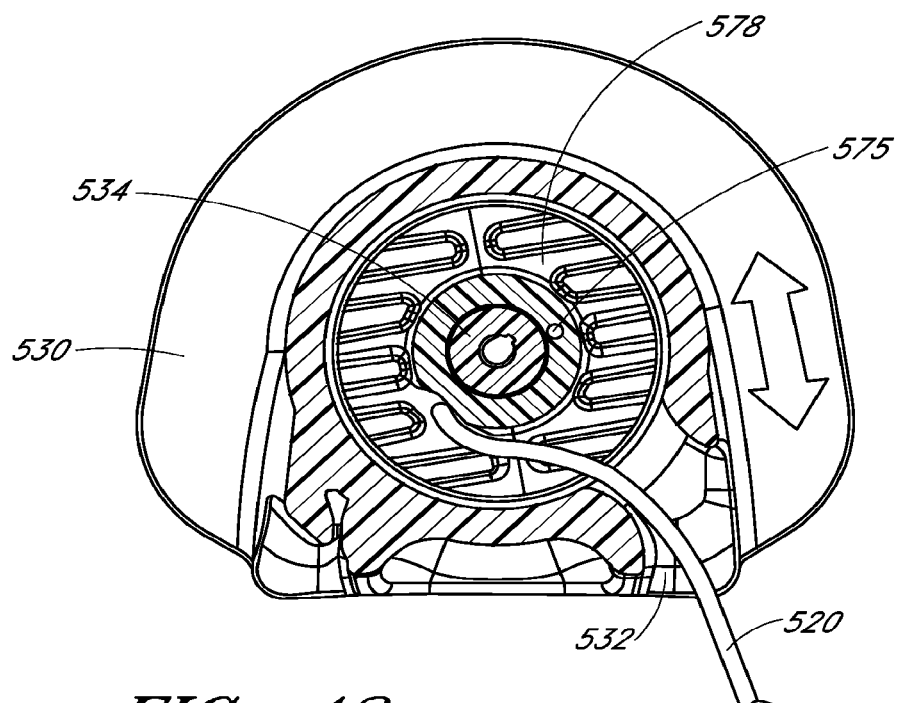
FIG. 42 is a section view of the lacing system illustrated in FIG. 41 taken along the line 42-42.
Figure 43:
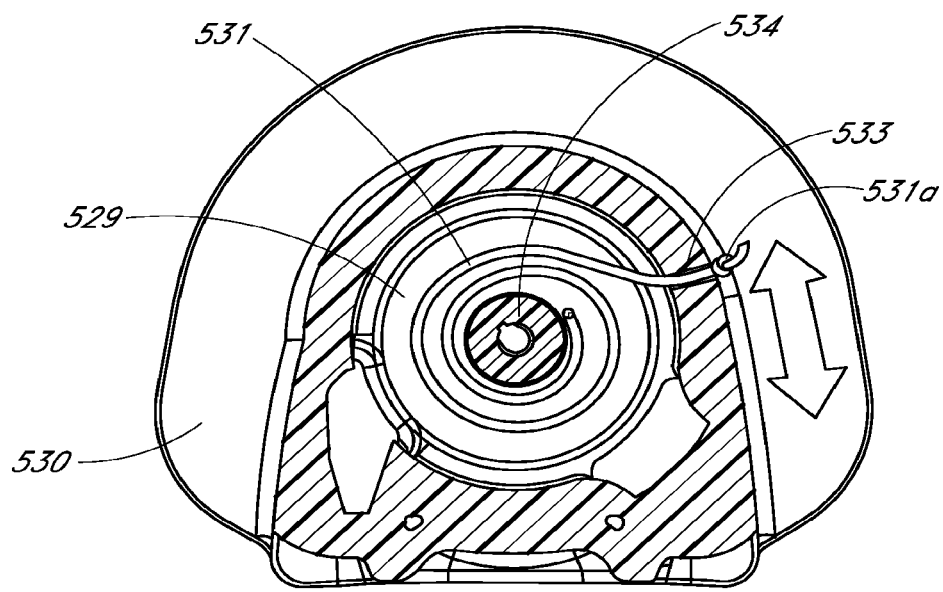
FIG. 43 is a section view of the lacing system illustrated in FIG. 41 taken along the line 43-43.

With reference now to FIGS. 37-43, an embodiment of a lacing system 510 will be described that includes a rotation limiter. In the illustrated embodiment, the rotation limiter can be a stop cord as will be described below. The lacing system 510 can include a housing 512, a spool member 514, a knob 516, and a fastener 518, which, in some respects, can be similar to, or the same as, the housing 12, spool member 14, knob 16, and fastener 18 described above, or any other housing, spool member, knob, or fastener described herein. Also, many features described in connection with the lacing system 510 can be incorporated into other embodiments disclosed herein. FIG. 37 is an exploded perspective view of the housing 512 and spool member 514 of another embodiment of a lacing system 510. For simplicity, the knob 516, fastener 518, and lace 520 are not shown in FIG. 37. FIG. 38 is a section view of the embodiment of the lacing system 510 in a close to fully wound configuration. FIG. 39 is a section view of the embodiment of the lacing system 510 of FIG. 38 taken through the line 39-39. FIG. 40 is a section view of the embodiment of the lacing system 510 of FIG. 38 taken through the line 40-40. FIG. 41 is a section view of the embodiment of the lacing system 510 in a close to fully unwound configuration. FIG. 42 is a section view of the embodiment of the lacing system 510 of FIG. 41 taken along the line 42-42. FIG. 43 is a section view of the embodiment of the lacing system 510 of FIG. 41 taken along the line 43-43.

The housing 512 can include a mounting flange 530 which can be configured to allow the housing 512 to be attached to a shoe or other object using stitching, rivets, screws, or other suitable fasteners. In some embodiments, the mounting flange 530 can be omitted, and the housing can be secured to the shoe or other object, for example, by screws threaded into the housing 512. The housing 512 can include a depression 28, and a shaft 534 that projects from the depression 28. The depression 528 and the shaft 534 can be configured to support the spool member 514 in a manner similar to that discussed above with regard to the housing 12 and spool member 14. The shaft 534 can include an opening 536 which can be configured to receive the fastener 518 to secure the knob 516 to the housing 512, in a manner similar to that described above. In some embodiments, a substantially annular raised ridge 535 can be formed in the periphery of the base of the depression 528 which can contact the bottom peripheral surface of the spool member 514 when the spool member 514 is positioned in the depression 528, thereby maintaining the spool member 514 a distance above the base of the depression 528 and forming a stop cord channel 529 between the bottom surface of the spool member 514 and the base of the depression 528. In the illustrated embodiment, the stop cord 531 can be wound around the shaft 534 as the spool 514 rotates relative to the housing 512. Although not specifically shown in the illustrated embodiment, the stop cord channel 529 can be formed as part of the spool 514. For example, a raised flange can be added to the bottom surface of the spool 514 to form a channel to receive the stop cord. Thus, in some embodiments, the spool 514 can include a lace channel for receiving the lace 520 and a separate stop cord channel for receiving the stop cord 531.

The housing can include one or more lace inlets 532 that can be configured to permit the lace 520 to be threaded into the housing 512. When the lacing system 510 is tightened, the lace 520 can enter the housing 512 through the inlet 532 and coil around the shaft 534 in a channel 578 formed in the spool member 514 in a manner similar to that discussed above in connection with the lacing system 10. When the lace is loosened, the lace 520 can uncoil and exit the housing through the lace inlet 532. In some embodiments, the lacing system 510 can include a second inlet configured to receive a stationary end of the lace 520 which can be secured to the housing such that it does not move in or out of the housing as the lace 520 is tightened or loosened.

The housing 512 can have a generally cylindrical shaped wall 538 projecting generally coaxially with the shaft 538 and substantially surrounding the depression 528. A plurality of radially positioned notches or depressions 40 can be formed on the inside surface of the wall 538 so as to form a series of radially positioned ratchet teeth 541 which can be configured to engage the pawls 562 of the spool member 514 to control the incremental rotation of the spool 514 in a manner similar, for example, to that described above in connection with the lacing system 10.

The lacing system 510 can include a stop cord 531, which can operate to prevent the knob 516 from being over-rotated in the either the tightening direction or in the loosening direction, as will be described in greater detail below. The stop cord 531 can have a first end 531a secured to the housing 512 and a second end 531b secured to the spool member 514, such that the stop cord 531 can coil around the shaft 536 as the spool member 514 rotates relative to the housing 512. In some embodiments, the first end 531a of the stop cord 531 can extend from the channel 529 formed in the depression 528 through a hole 533 formed radially in the wall 538, and a knot can be formed on the outside of the wall 538 thereby preventing the first end 531a of the stop cord 531 from being pulled through the hole 533 and into the depression 528. The first end 531a of the stop cord 531 can be secured to the housing in various other manners, such as, for example, using an adhesive, a clamp, or a friction fitting (e.g., created by passing the stop cord 531 through a plurality of channels in a manner similar to that described above in connection with FIG. 16).

The second end 531b of the stop cord 531 can extend from the channel 529 through a hole 535 formed axially in the spool member 514, and a knot can be formed on the top of the spool member 514 thereby preventing the second end 531b of the stop cord 531 from being pulled through the hole 535 and into the channel 529. The second end 531b of the stop cord 531 can be secured to the spool member 514 in various other manners, such as, for example, using an adhesive, a clamp, or a friction fitting (e.g., created by passing the stop cord 531 through a plurality of channels in a manner similar to that described above in connection with FIG. 16).

The stop cord 531 can be made of any of a variety of materials including steel, monofilament, nylon, Kevlar, or any other suitable material. One example of a suitable stop cord material is sold under the trade name SPECTRA™, manufactured by Honeywell of Morris Township, N.J. In some embodiments, the stop cord 531 can be similar to, or the same as, the lace 520 in construction or size or other regards.

With reference now to FIGS. 38-43, the operation of the stop cord 531 will now be described. As can best be seen in FIG. 39, when the knob 516 is rotated in the tightening direction, the lace 520 is drawn into the channel 78 via the lace inlet 532 and the lace 520 coils around the shaft 534. As additional lace 520 is drawn into the channel 578 the channel 578 becomes full. If the user continues to rotate the knob 516 once the channel 578 is full, the lace 520 can become jammed or the lacing system 510 may be damaged. To prevent over-insertion of the lace 520, the stop cord 531 can be configured to limit the amount of lace which can be drawn into the channel 578 by limiting the amount that the knob 516 can be rotated. As can best be seen in FIG. 40, as the knob 516 is rotated, the stop cord 531 is coiled around the shaft 534 within the channel 529. By selecting an appropriate length for the stop cord 531, the stop cord 531 can become tightly wound around the shaft 534 after a predetermined number of turns of the knob 516. Once the stop cord 531 has become tightly wound it prevents the knob from being tightened further. By selecting a length for the stop cord 531 that corresponds to the size of the channel 578 and the size of the lace 520, the stop cord 531 can "lock" the knob once the channel has become substantially filled. In some embodiments, the stop cord 531 can be configured to "lock" the knob 516 against further tightening when the channel 578 still contains space for additional lace, depending on the particular application of the lacing system 510.

As can best be seen in FIG. 42, when the knob 516 is rotated in the loosening direction, the lace 520 is drawn out of the channel 578 via the lace inlet 532 until the lace 520 is fully uncoiled from around the shaft 534. If the user continues to rotate the knob 516 in the loosening direction once the lace 520 is fully uncoiled, the lace 520 will begin to coil around the shaft in the opposite direction and begin to tighten. In unidirectional spool configurations, the lace tightening system is designed to tighten in a single direction. Thus, the stop cord 531 can be used to prevent the user from turning the knob 516 in the loosening direction after the lace 520 has become fully loosened. As can best be seen in FIG. 43, as the knob 516 is rotated in the loosening direction, the stop cord 531 is coiled around the shaft 534 in the opposite direction from that shown in FIG. 40. By selecting an appropriate length for the stop cord 531, the stop cord 531 can become tightly wound around the shaft 534 when the lace 520 becomes substantially fully loosened, thereby "locking" the knob 516 against further rotation in the loosening direction. It will be understood that the stop cord can be used to "lock" the knob 516 against additional loosening before the lace 520 has become fully loosened, depending on the particular application of the lacing system 510.

In the embodiment of the lacing system 510 shown in FIGS. 37-43, the spool member 514 is a unidirectional spool member. Accordingly, the stop cord 531 can be fully coiled in a first direction when the lace 520 is substantially fully loosened, thereby preventing the knob 516 from being loosened further, and fully coiled in a second, opposite direction when the channel 578 is substantially filled, thereby preventing the knob 516 from being tightened further. Consequently, the stop cord 531 can be substantially uncoiled when the knob 516 is approximately midway between its fully loosened and fully tightened rotational positions. The number of knob revolution between the fully tightened and fully loosened positions can be approximately double the number of times the stop cord 531 can be wrapped around the shaft 534. In the embodiment shown in FIGS. 40 and 43, the stop cord 531 can have a length that allows the stop cord 531 to be wrapped approximately twice around the shaft 534, which translates into approximately four revolutions of the knob 516 and spool member 514 between the fully loosened and fully tightened positions. Many variations are possible following this same approximately 2:1 ratio. For example, to provide for approximately six revolutions between the fully loosened and fully tightened positions, a longer stop cord 531 can be used that can be wrapped around the shaft 534 approximately three times.

In some embodiments, the spool member can be a bidirectional spool member (e.g., the spool member 114 of FIG. 26) such that the lacing system can be tightened by turning the knob in either direction. In some bidirectional embodiments, the stop cord can be fully coiled in a first direction when the knob has been fully tightened in a first direction, and the stop cord can be fully coiled in a second, opposite direction when the knob has been fully tightened in the second direction. Thus, in some bidirectional embodiments, the stop cord can be fully uncoiled at substantially the same position where the lace is fully loosened. In some bidirectional embodiments, the number of knob revolutions between the fully loosened and fully tightened positions can approximately equal the number of time that the stop cord can be wound around the shaft 534.

FIGS. 44-50 illustrate an embodiment of a lace winder 600, which can be used in connection with a lacing system, such the lacing system 10 described above. As will be described in greater detail below, the lace winder 600 can include a spring configured to automatically eliminate loose slack in the lace by maintaining the lace under tension. The lace winder 600 can also include a knob 622 configured to tighten the lace when rotated in a tightening direction and to loosen the lace when rotated in a loosening direction. In some embodiments, the knob 622 can be incrementally rotatable in the loosening direction, allowing for incremental release of the lace from the lace winder 600.

In the illustrated embodiments, the lace winder 600 generally comprises a spool 610 rotatably positioned within a housing member 640 and rotationally biased in a winding direction. The spool 610 is also generally coupled to a knob 622 for manually tightening the lace. Some features of the lace winder 400 can be the same as, or similar to, features of the lacing system 10 discussed above. However, in alternative embodiments, features of the lace winder 600 can be applied to many other tightening mechanisms as desired.

Figure 44:
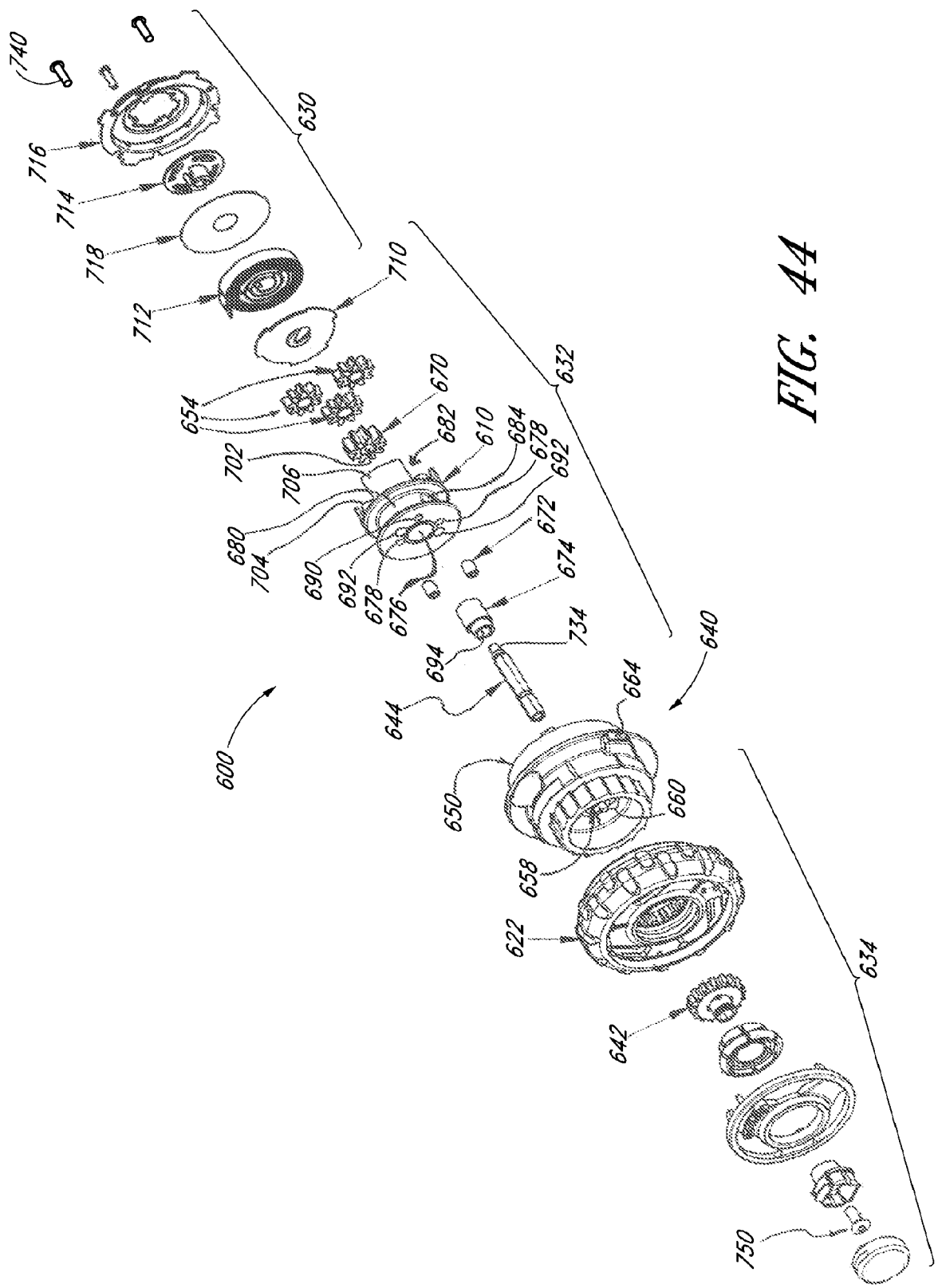
FIG. 44 is an exploded perspective view of an embodiment of a lace winder.

FIG. 44 shows an exploded view of one embodiment of the lace winder 600. The embodiment of FIG. 44 illustrates a spring assembly 630, a spool assembly 632 and a knob assembly 634. The spool assembly 632 and the spring assembly 630 are generally configured to be assembled to one another and placed within a housing 640. The knob assembly 634 can then be assembled with the housing 640 to provide a self-winding lacing device 600. The knob assembly 634 generally comprises a knob 622 and a drive gear 642 configured to rotationally couple the knob 622 to a drive shaft 644 which extends through substantially the entire winder 600.

Figure 45:
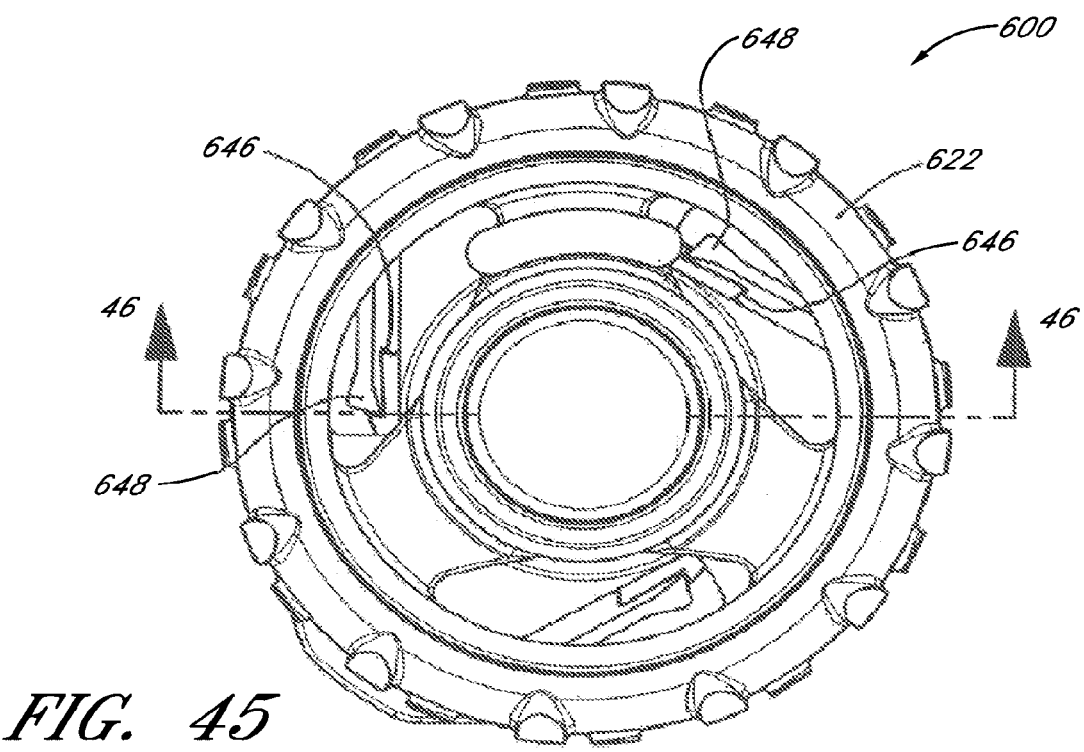
FIG. 45 is a top view of the lace winder illustrated in FIG. 44.
Figure 46:
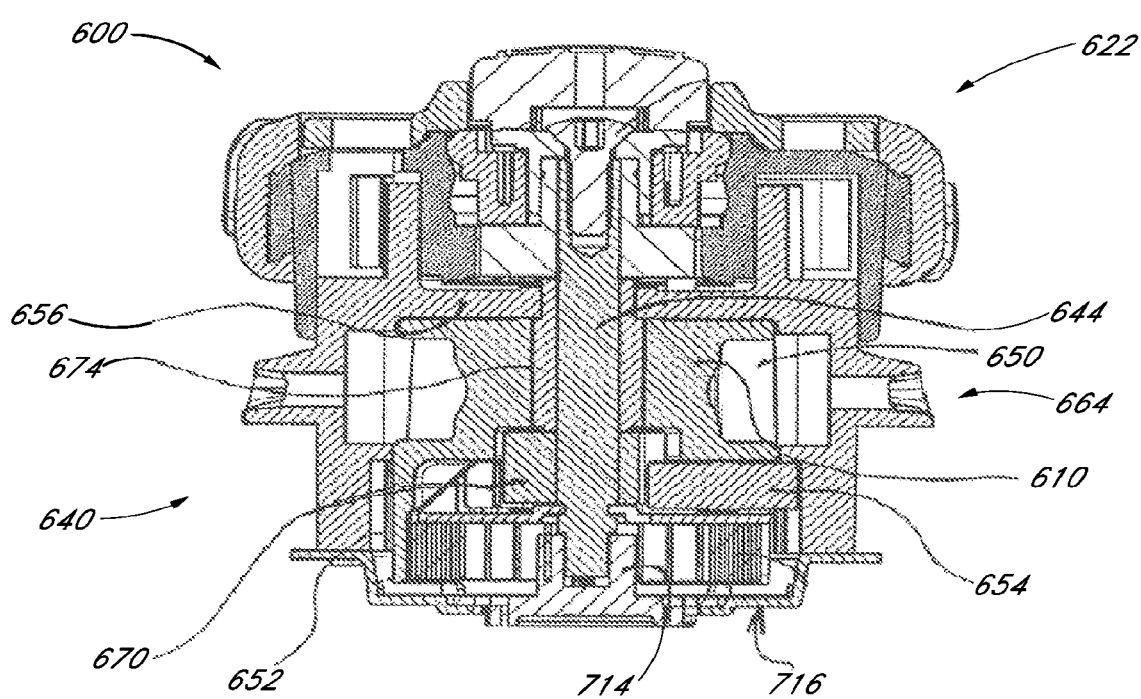
FIG. 46 is a section view of the lace winder illustrated in FIG. 45 taken along the line 46-46.
Figure 47:
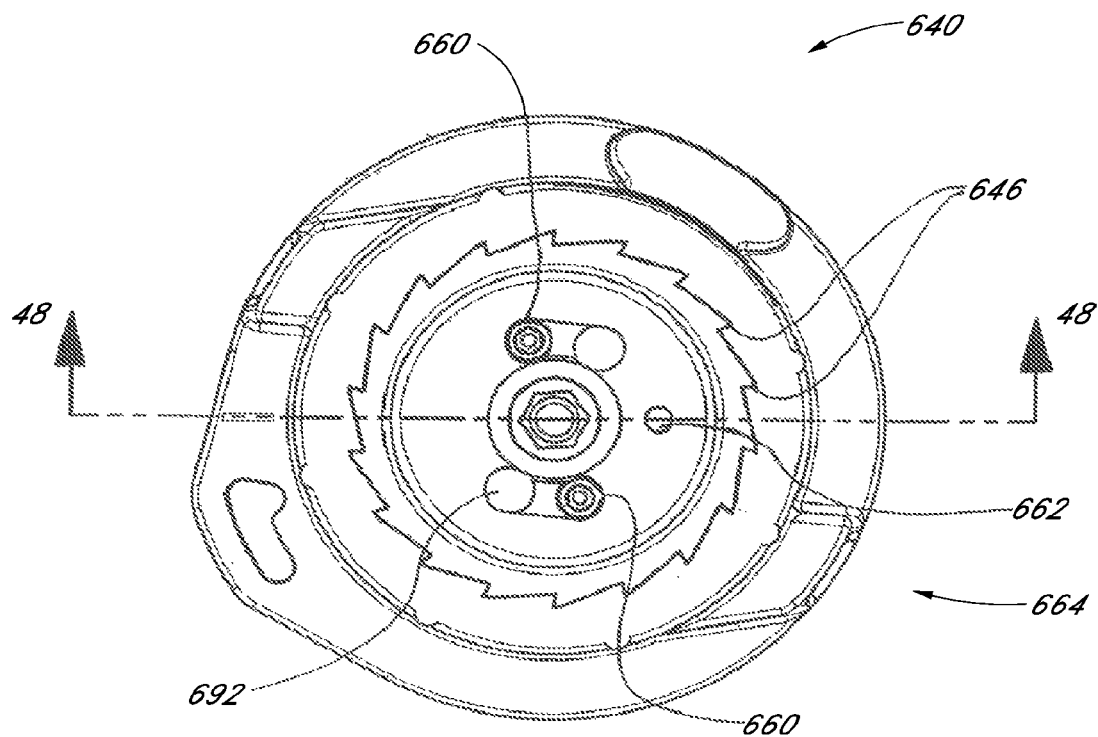
FIG. 47 is a top view of a housing component of the lace winder illustrated in FIG. 44.
Figure 48:
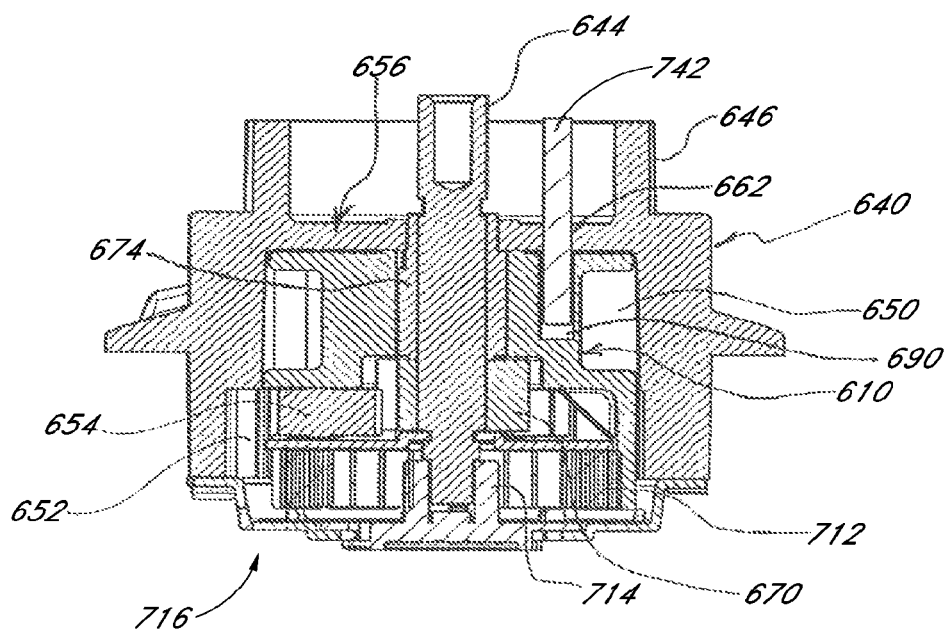
FIG. 48 is a section view of the housing illustrated in FIG. 47 taken along the line 48-48.
Figure 49:
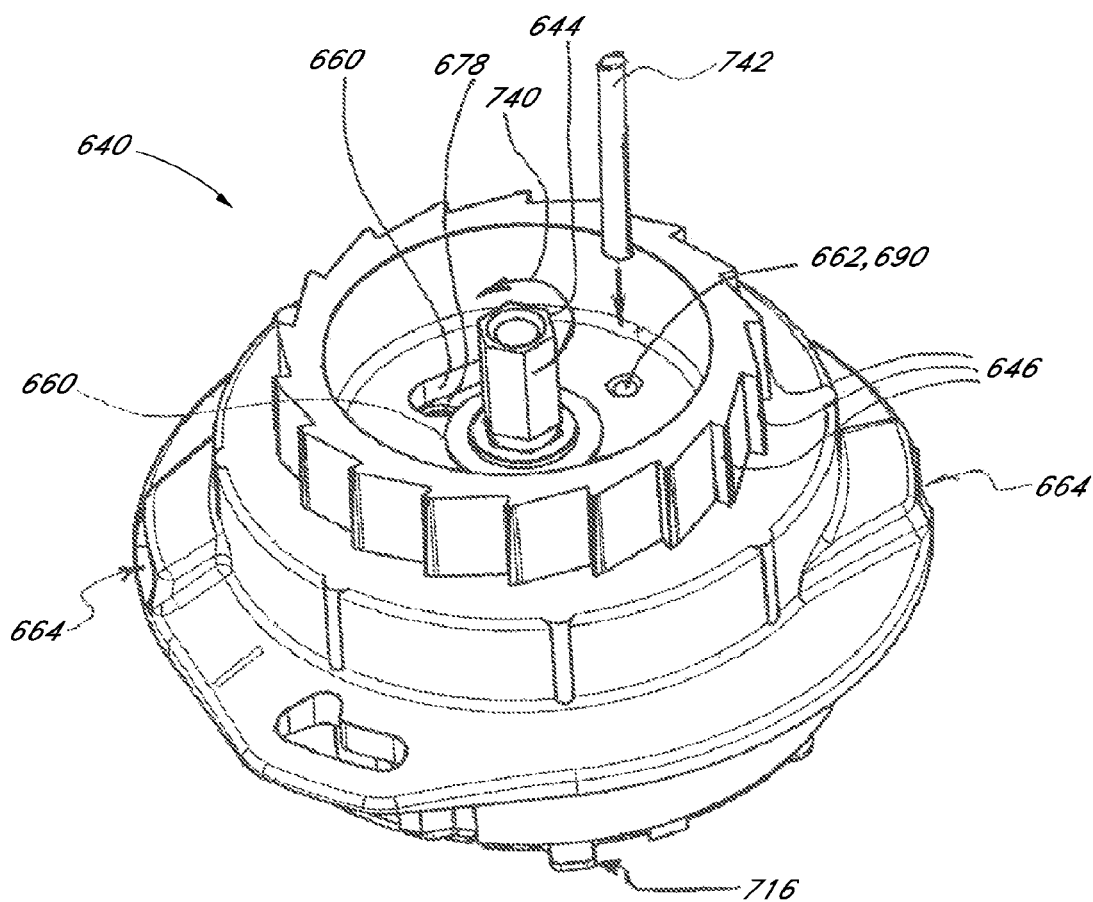
FIG. 49 is a perspective view of the housing illustrated in FIG. 44.

FIG. 45 shows a top view of the lace winder 600 of FIG. 44. FIG. 46 is a section view of the lace winder 600 of FIG. 45 taken along line 46-46. FIG. 49 is a top view of the housing 640 shown in FIG. 44. FIG. 48 is a section view of the housing 640 of FIG. 47 taken along the line 48-48. FIG. 49 is a perspective view of the housing 640 of FIG. 47. With reference to FIG. 45-49, in some embodiments, the housing 640 generally comprises an upper section with a plurality of ratchet teeth 646 configured to engage pawls 648 of the knob 622 (e.g., as shown in FIG. 45). The housing 640 also includes a spool cavity 650 sized and configured to receive the spool assembly 632 and spring assembly 630 therein. A lower portion of the spool cavity 650 generally comprises a plurality of teeth forming a ring gear 652 configured to engage planetary gears 654 of the spool assembly 632.

A transverse surface 656 generally separates the upper portion of the housing 640 from the spool cavity 650. A central aperture 658 in the transverse surface allows the drive shaft 644 to extend from the knob 622, through the housing 640 and through the spool assembly 632. In some embodiments, set-screw apertures 660 and/or a winding pin aperture 662 can also extend through the housing 640 as will be further described below. The housing 640 also typically includes a pair of lace entry holes 664 through which laces can extend.

In some embodiments, a gear train can be provided between the knob 622 and the spool 610 in order to allow a user to apply an torsional force to a spool 610 that is greater than the force applied to the knob. In the embodiment of FIGS. 44-48, such a gear train is provided in the form of an epicyclic gear set including a sun gear 670 and a plurality of planetary gears 654 attached to the spool 610, and a ring gear 650 on an internal surface of the housing 640. The illustrated epicyclic gear train will cause a clockwise rotation of the drive shaft 644 relative to the housing 640 to result in a clockwise rotation of the spool 610 relative to the housing 640, but at a much slower rate, and with a much increased torque. This provides a user with a substantial mechanical advantage in tightening footwear laces using the illustrated device. In the illustrated embodiment, the epicyclic gear train provides a gear ratio of 1:4. In alternative embodiments, other ratios can also be used as desired. For example, gear ratios of anywhere from 1:1 to 1:5 or more could be used in connection with a footwear lace tightening mechanism. In some embodiments, the gear train can be omitted from the lace winder 600.

With reference to FIGS. 44, 46, and 48, embodiments of a spool assembly 632 will now be described. The spool assembly 632 generally comprises a spool body 610, a drive shaft 644, a sun gear 670, a plurality of planetary gears 654, a pair of set screws 672 and a bushing 674. The spool body 610 generally comprises a central aperture 676, a pair of set screw holes 678, a winding section 680 and a transmission section 682. The winding section 680 comprises a pair of lace receiving holes 684 for receiving lace ends which can be secured to the spool using set screws 672 or other means as described in previous embodiments. The lace receiving holes 684 are generally configured to be alignable with the lace entry holes 664 of the housing 640. In some embodiments, the spool body 610 also comprises a winding pin hole 690 configured to receive a winding pin for use in assembling the winder 600 as will be further described below. In some embodiments, the spool 610 can also include sight holes 692 to allow a user to visually verify that a lace 23 has been inserted a sufficient distance into the spool 610 without the need for markings on the lace 23.

The bushing 674 comprises an outer diameter that is slightly smaller than the inner diameter of the spool central aperture 676. The bushing 674 also comprises an inner aperture 694 configured to engage the drive shaft 644 such that the bushing 674 remains rotationally stationary relative to the drive shaft throughout operation of the device. In the illustrated embodiment, the drive shaft 644 comprises a hexagonal shape, and the bushing 674 comprises a corresponding hexagonal shape. In the illustrated embodiment, the sun gear 670 also comprises an hexagonal aperture 702 configured to rotationally couple the sun gear 670 to the drive shaft 644. Alternatively or in addition, the sun gear 670 and/or the bushing 674 can be secured to the drive shaft 644 by a press fit, keys, set screws, adhesives, or other suitable means. In other embodiments, the drive shaft 644, bushing 674 and/or sun gear 670 can comprise other cross-sectional shapes for rotationally coupling the elements.

In an assembled condition, the bushing 674 is positioned within the spool aperture 676, the drive shaft 644 extends through the central aperture 694 of the bushing 674 and through the sun gear 670. In some embodiments, the planetary gears 654 can be secured to axles 704 rigidly mounted to the transmission section 682 of the spool 610. The planetary gears 654, when assembled on the spool 610, generally extend radially outwards from the perimeter of the spool 610 such that they may engage the ring gear 652 in the housing 640. In some embodiments, the spool transmission section 682 comprises walls 706 with apertures located to allow the planetary gears 654 to extend therethrough. If desired, a plate 710 can be positioned between the planetary gears 654 and the spring assembly 630 in order to prevent interference between the moving parts.

The spring assembly 630 generally comprises a coil spring 712, a spring boss 714, and a backing plate 716. In some embodiments, a washer/plate 718 can also be provided within the spring assembly 630 between the coil spring 718 and the spring boss 714 in order to prevent the spring 712 from undesirably hanging up on any protrusions of the spring boss 714.

Figure 50:
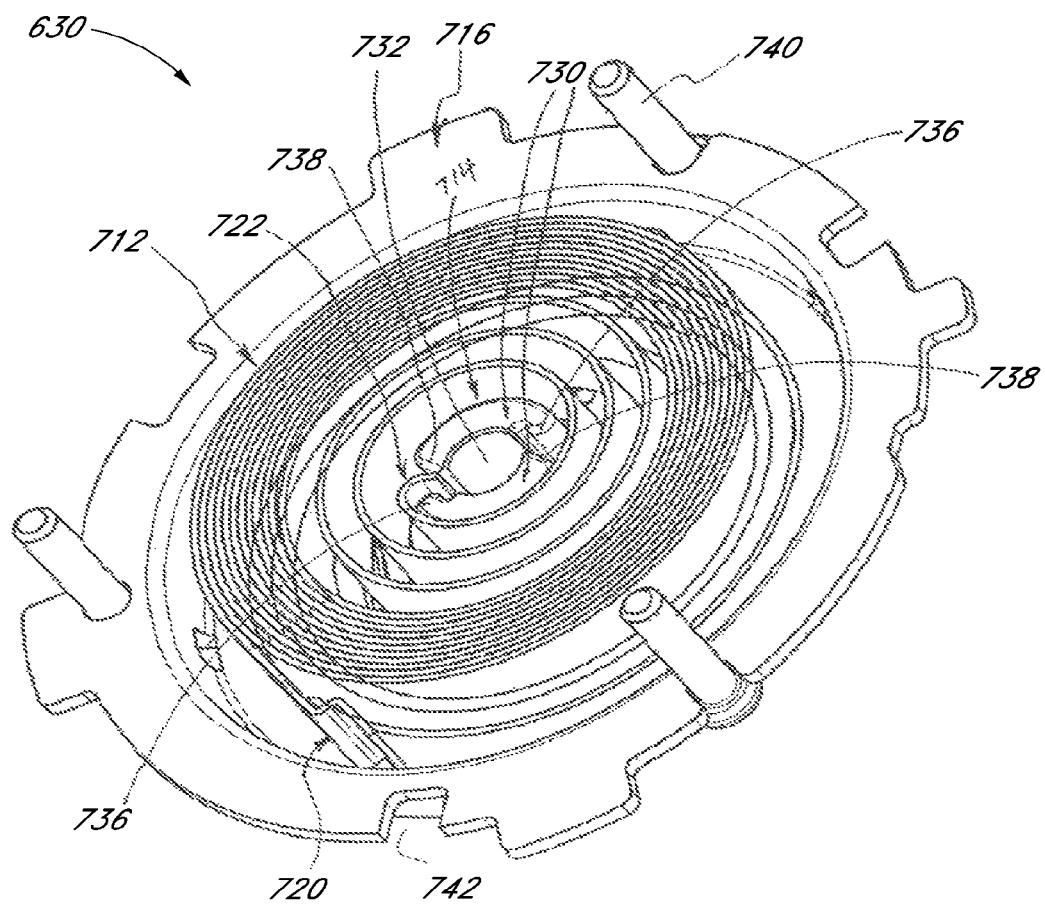
FIG. 50 is a perspective view of a spring element illustrated in FIG. 44.

FIG. 50 is a perspective view of an embodiment of the spring assembly 630 shown in FIG. 44. With particular reference to FIG. 50, in some embodiments, the spring boss 714 is rigidly joined to the backplate 716 and the torsional spring 712 is configured to engage the spring boss 714 in at least one rotational direction. The coil spring 712 generally comprises an outer end 720 located at a periphery of the spring 712, and an inner end 722 at a central portion of the spring 712. The outer end 720 is generally configured to engage a portion of the spool 610. In the illustrated embodiment, the outer end 720 comprises a necked-down portion to engage an aperture in a portion of the spool 610. In alternative embodiments, the outer end 720 of the spring 712 can be secured to the spool by welds, mechanical fasteners, adhesives or any other desired method. The inner end 722 of the spring 712 comprises a hooked portion configured to engage the spring boss 714.

The spring boss 714 comprises a pair of posts 730 extending upwards from the backplate 716. The posts 730 are generally crescent shaped and configured to engage the hooked interior end 722 of the spring 712 in only one rotational direction. Each post 730 comprises a curved end 736 configured to receive the hooked spring end 722 as the spring rotates counter-clockwise relative to the backplate 716. Each post 730 also comprises a flat end 738 configured to deflect the hooked spring end 722 as the spring 712 rotates clockwise relative to the backplate 716. In the illustrated embodiment, the posts 714 and spring 712 are oriented such that a clockwise rotation of the spring 712 relative to the spring boss 714 and backplate 716 will allow the spring to "skip" from one post 714 to the other without resisting such rotation. On the other hand, a counter-clockwise rotation of the spring 712 will cause the hooked end 722 to engage one of the posts 714, thereby holding the interior end 722 of the spring stationary relative to the outer portions of the spring 712. Continued rotation of the outer portions of the spring will deflect the spring, thereby biasing it in the clockwise winding direction.

The space 732 between the posts 730 of the spring boss 714 is generally sized and configured to receive the distal end of the drive shaft, which in some embodiments as shown in FIG. 44, can comprises a circular end 734 configured to freely rotate in the spring boss space 732. In the embodiment illustrated in FIG. 44, the spring boss 714 and the backplate 716 are shown as separately manufactured elements which are later assembled. In alternative embodiments, the backplate 716 and spring boss 714 can be integrally formed as a unitary structure and/or as portions of another structure.

Embodiments of methods for assembling a self-coiling lace winder 600 will now be described with reference to FIGS. 44-49. In one embodiment, the sun and planetary gears 670, 654 are assembled onto the transmission portion 682 of the spool 610, and the bushing 674 and drive shaft 644 are inserted through the aperture 676 in the spool. The spring assembly 630 is assembled by attaching the spring boss 714 to the back plate 716 by any suitable method and placing the spring 712 on the spring boss 714. The spool assembly 632 can then be joined to the spring assembly 630 by attaching the outer end 720 of the spring 712 to the spool 610. In some embodiments, the spring 712 may need to be pre-wound tightly in order to fit within the spool walls 706. The spool assembly 632 and the spring assembly 630 can then be placed within the housing member 640. In some embodiments, the backplate 716 is secured to the housing member 640 by screws 740 or other suitable fasteners such as rivets, welds, adhesives, etc. In some embodiments, the backplate 716 can include notches 742 configured to cooperate with extensions or recesses in the housing member 640 in order to prevent the entirety of the torsional spring load from bearing against the screws 740.

In some embodiments, once the spool assembly 632 and the spring assembly 630 are assembled and placed in the housing 640, the spring 712 can be tensioned prior to attaching the laces. In one embodiment, with reference to FIG. 26, the spring 712 is tensioned by holding the housing 640 stationary and rotating the drive shaft 644 in an unwinding direction 740, thereby increasing the deflection in the spring 712 and correspondingly increasing a biasing force of the spring. Once a desired degree of deflection/spring bias is reached, a winding pin 742 can be inserted through the winding pin aperture 662 in the housing 640 and the winding pin hole 690 in the spool 610.

In one embodiment, the winding pin hole 690 in the spool is aligned relative to the winding pin aperture 662 in the housing such that the set screw holes 678 and the lacing sight holes 692 in the spool 610 will be aligned with corresponding apertures 660 in the housing 640 when the winding pin 742 is inserted (see FIG. 50). The spool 610 and housing 640 are also preferably configured such that the lace receiving holes 684 of the spool 610 are aligned with the lace entry holes 664 of the housing 640 when the winding pin hole 690 and aperture 662 are aligned. In alternative embodiments, the winding pin hole 690 and aperture 662 can be omitted, and the spool can be held in place relative to the housing by some other means, such as by placing a winding pin 742 can be inserted through a set screw hole and aperture or a sight hole/aperture.

Once the spring 712 has been tensioned and a winding pin 742 has been inserted, the lace can be installed in the spool using any suitable means provided. In the embodiment illustrated in the embodiments of FIGS. 44-49, the spool 610 is configured to secure the lace therein with set screws 672. The lace can be inserted through the lace entry holes 664 in the housing 640 and through the lace receiving holes 684 in the spool 610 until a user sees the end of the lace in the appropriate sight hole 692. Once the user visually verifies that the lace is inserted a sufficient distance, the set screws 672 can be tightened, thereby securing the laces in the spool.

Once the laces are secured, the winding pin 742 can be removed, thereby allowing the spring to wind up any slack in the lace. The knob 622 can then be attached to the housing 640, such as by securing a screw 750 to the drive shaft 644. A user can then tighten the lace using the knob 622 as desired.

In alternative embodiments, it may be desirable to pretension the spring 712 after installing the lace in the spool 610. For example, if an end user desires to change the lace in his/her footwear, the old lace can be removed by removing the knob 622, loosening the set screws 672 and pulling out the lace. New lace can then be inserted through the lace entry holes 684 and secured to the spool with the set screws 672, and re-install the knob 622 as described above. In order to tension the spring 712, a user can then simply wind the lace by rotating the knob 622 in the winding direction until the laces are fully tightened (typically without a foot in the footwear). The spring will not resist such forward winding, since the spring boss 714 will allow the spring 712 to freely rotate in the forward direction as described above. In one preferred embodiment, the user tightens the lace as much as possible without a foot in the footwear. Once the laces are fully tightened, the knob can be released, such as by pulling outwards on the knob as described elsewhere herein, and the lace can be pulled out. As the spool rotates in an unwinding direction, the hooked inner end 722 of the spring 712 engages the spring boss 714, and the spring deflects, thereby again biasing the spool 610 in a winding direction.

Figure 51:
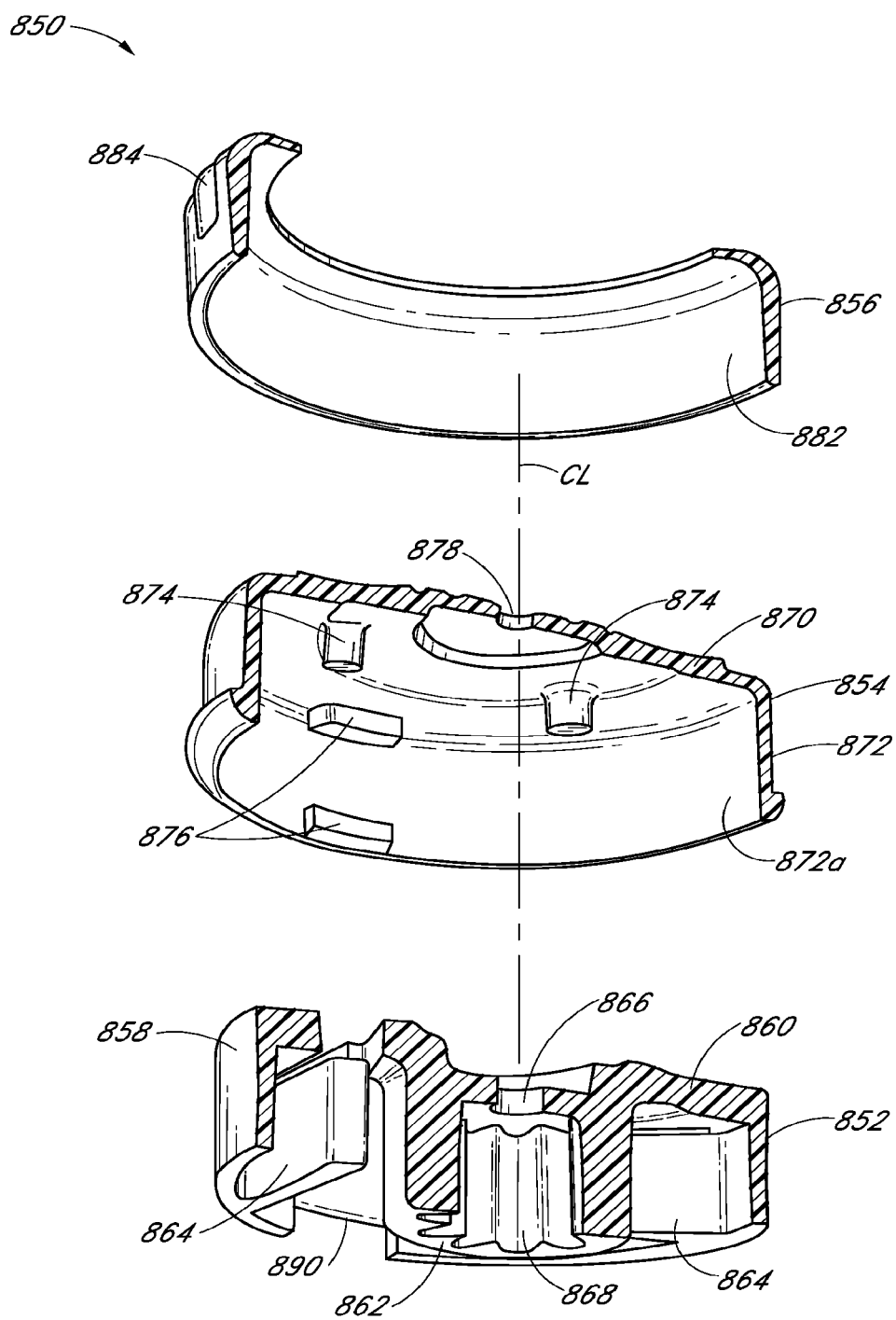
FIG. 51 is a perspective, section view of a partially exploded embodiment of a knob assembly.
Figures 52, 53:
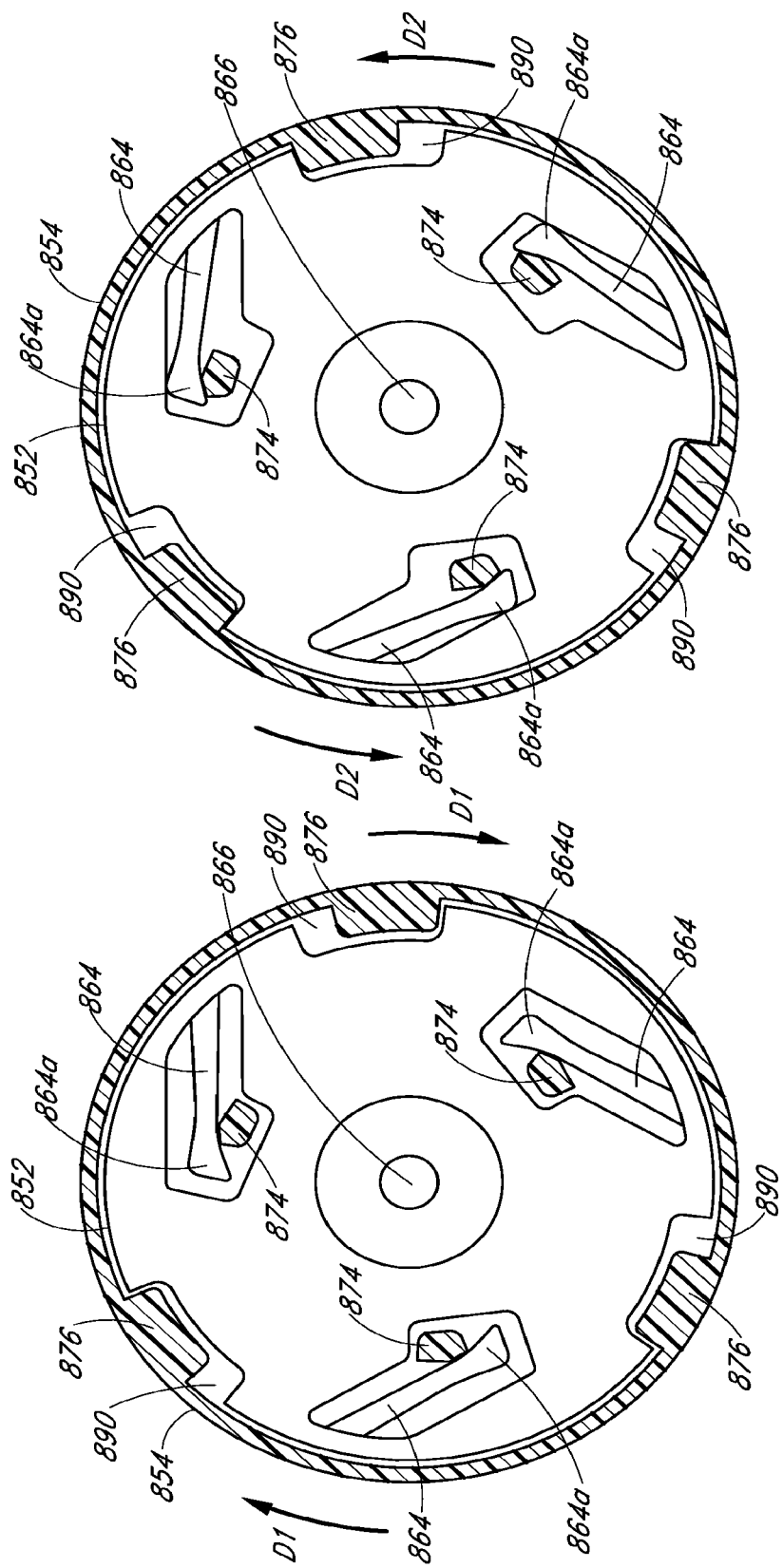
FIG. 52 is a section view of the embodiment of the knob assembly illustrated in FIG. 51, showing the knob assembly in a tightening mode.
FIG. 53 is a section view of the embodiment of the knob assembly illustrated in FIG. 51, showing the knob assembly in a loosening mode.

With reference now to FIGS. 51-53, an additional embodiment of a knob assembly 850 will be described. Some embodiments of the knob assembly 850 can be used, for example, with the lace winder 600 described above. In some embodiments, the knob assembly 850 can be used with a lace winder that can be a modified version of the lace winder 600 having less than all the features or parts of the described embodiment of the lace winder 600 (e.g., no self winding feature) or having additional features other than those described. In some embodiments, features of the knob assembly 850 can also be applied other embodiments disclosed herein. For example, the housing 12 and knob 16 can be modified to operate in a fashion similar to the knob assembly 850.

FIG. 51 is a perspective, section view of a partially exploded embodiment of a knob assembly 850. The embodiment of the knob assembly 850 illustrated in FIG. 51 can comprise a base member 852, a cover member 854, and an overmold or overlay member 856. In some embodiments, the base member 852 can be formed from a rigid or a semi-rigid material, and can comprise a substantially cylindrical outer surface 858, a substantially planar upper surface 860, a coupling portion 862 protruding from the upper surface 858, a substantially planar upper surface 860, a coupling portion 862 protruding from the upper surface 860 in a direction that is substantially perpendicular to the upper surface 860, and one or more engagement tabs 864. Additionally, in some embodiments, the base member 852 can comprise an opening 866 therethrough that is approximately coaxial with the centerline of the base member 858, and a plurality of channels or depressions 868 formed in the coupling portion 362.

In some embodiments, the cover member 854 can have an approximately planar upper surface 870, an approximately cylindrical outer wall 872 projecting substantially perpendicular to the upper surface 870, a plurality of tabs 874 protruding substantially perpendicular to the upper surface 870, and a plurality of protrusions projecting substantially radially inward from the inside surface 872a of the outer wall 872. Additionally, an opening 878 can be formed through the upper wall 870 at the approximate center of the cover member 854.

The overlay member 856 can be configured to be supported by the cover member 854 such that the inner surface 882 of the overlay member 856 is positioned adjacent to the outer surface of the outer wall 872. In some embodiments, the overlay member 856 can be formed from a pliable material such as rubber or any other suitable material, and can have depressions 884 or any other features such as, but not limited to, channels, protrusions, dimples, tabs, or other features configured to increase the user's grip on the knob assembly 850.

FIG. 52 is a section view of the embodiment of the knob assembly 850 illustrated in FIG. 51, taken through the plan that is perpendicular to the centerline of the assembly (represented by line CL in FIG. 51) and that intersects each of the tabs 874 formed on the upper surface 879 of the cover member 854. FIG. 52 illustrates the knob assembly 850 in a tightening mode. FIG. 53 is a section view of the embodiment of the knob assembly 850 illustrated in FIG. 51, taken through a plane that is perpendicular the other centerline of the assembly (represented by line CL in FIG. 51) and that intersects each of the tabs 874 formed on the upper surface 870 of the cover member 854. FIG. 53 illustrates the knob assembly 850 in a loosening mode.

With reference to FIGS. 52-53, the base member 852 and the cover member 854 can be coupled so that the tabs 874 formed on the cover member 854 are positioned adjacent to the engagement tabs 864 supported by the base member 852. When the knob assembly 850 is in tightening mode as illustrated in FIG. 52 (i.e., when the knob assembly 850 is rotated in the first represented by arrow D1 and FIG. 52), the tabs 874 formed on the cover member 854 can be positioned relative to the engagement tabs 864 supported by the base member 852 so that the engagement tabs 864 are not bent or deflected by the contact with the tabs 874 of the cover member 854. Additionally, in the tightening mode as illustrated in FIG. 52, each of the tabs or protrusions 876 formed on the cover member 854 can engage each of the cutouts 890 formed in the base member 852 such that, turning the cover member 854 in a first or tightening direction (represented by arrow D1 in FIG. 52) can cause the tabs 876 to contact on of the walls formed by the cutouts 890 and, accordingly, cause the base member 852 to turn in the first direction D1.

With reference to FIG. 53, the tabs 874 formed on the cover member 854 can be forced against the engagement tabs 864 supported by the base member 852 so that the engagement tabs 864 are deflected outward by the contact with the tabs 874 of the cover member 854. As will be described in greater detail below, when the engagement tabs 864 are deflected outward to a sufficient amount by the contact with the tabs 874, the knob assembly 850 can rotate freely in the second or loosening direction (represented by arrow D2 in FIG. 53), causing the spool member coupled with the knob assembly 850 to also rotate in a second direction D2, loosening the lace in the lacing system. Additionally, in the loosening mode as illustrated in FIG. 53 (i.e., when the knob assembly is rotated in the second direction D2), each of the tabs or protrusions 876 formed on the cover member 854 can engage each of the cutouts 890 formed on the base member 852 such that, turning the cover member 854 in a second or loosening direction D2 can cause the tabs 876 to contact the wall forming cutouts 890 and, accordingly, cause the base member 852 to turn in the second direction D2.

As mentioned above, some embodiments of the knob assembly 850 can be configured to be interchangeable with the knob 622 of the lace winder 600 described above (and further described in U.S. Patent Application Publication No. 2006-0156517 (hereinafter, the '517 Publication)), to enable the lace winder 600 to be incrementally releasable. The knob assembly 850 will be further discussed below with as being incorporated into the lace winder 600 described above. In this configuration, the knob assembly 850 can be configured such that, when the knob assembly is rotated in a first, tightening direction D1 as described above, the knob assembly 850 can rotate the spool assembly 632 of the lace winder 600 in the first, tightening direction.

Similarly, the knob assembly 850 can be configured such that, when the knob assembly 850 is rotated in a second, loosening direction D2 as described above, the engagement tabs 874 of the cover member 854 can deflect the engagement tabs 864 of the base member 852 outwardly so that the free ends 864a of the engagement tabs 864 do not contact the ratchet teeth 646 (see FIGS. 45, 47, and 49) of the lace winder 600 and, accordingly, the knob assembly 850 can rotate the spool assembly 632 of the lace winder 600 in the second, loosening direction. In this manner, the lace winder 600, or other reel or lacing system can be configured to permit incremental release of lace in the lacing system.

In this configuration, the knob assembly 850 can be subjected to a rotational bias tending to cause the spool assembly 632 of the lace winder 600 and the knob assembly 850 to rotate in the second, loosened direction D2 by the tension from the lace on the spool assembly 632 in a tightened or partially tightened lacing system exerted. To counteract the above-mentioned bias and prevent the rotation of the spool assembly 632 in the second, loosening direction, the engagements tabs 864 supported by the base member 852 of the knob assembly 850 can engage with the ratchet teeth 646 of the lace winder 600 to impede or prevent the further rotation of the spool assembly 632 of the lace winder 600 in the second, loosening direction. Additionally, in some embodiments, the knob assembly 850 can be configured to be axially movable relative to the spool assembly 632 of the lace winder 600 so that, when the knob assembly 850 is moved a sufficient distance away from the spool assembly 632 of the lace winder 600, the engagement tabs 864 of the knob assembly 850 can be moved out of contact with the ratchet teeth 646 of the lace winder so that the knob assembly 850 and the spool assembly 632 of the lace winder 600 can be freely rotated in the second, loosening directions.

Figure 54A:
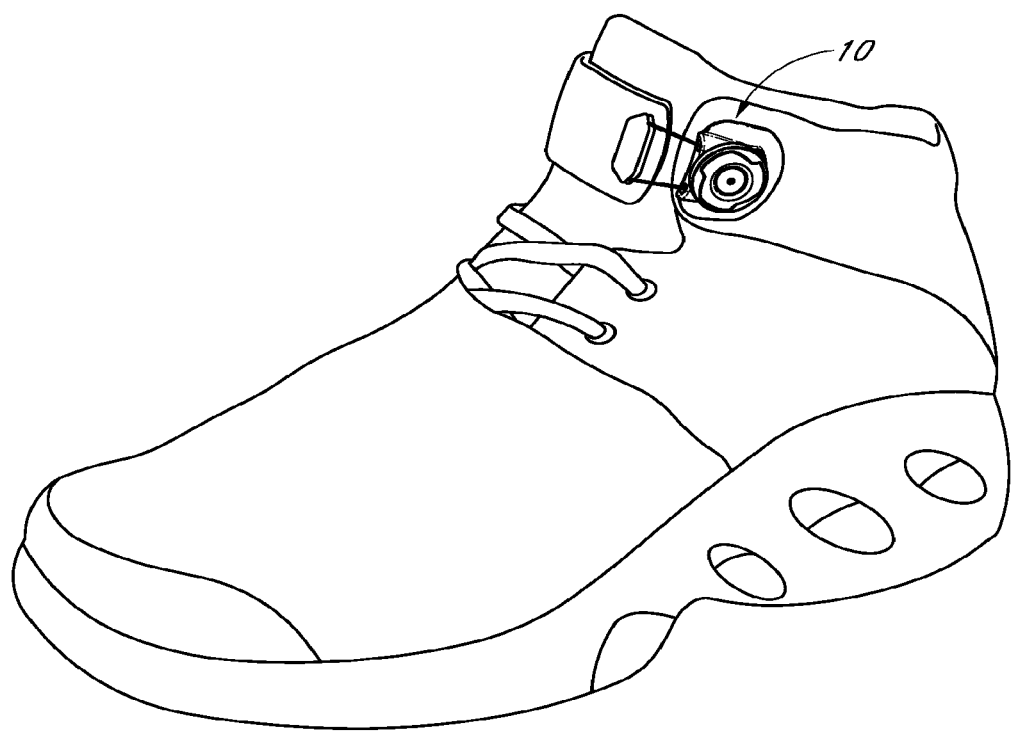
FIGS. 54A-54H are perspective views of various exemplary articles of manufacture suitable for use with any embodiments of the lacing systems disclosed or incorporated herein.

FIGS. 54A-54H are perspective views of various articles of manufacture suitable for use with any embodiments of the lacing systems described herein including, but not limited to, lacing system 10, or any combination of components of the various lacing systems described herein. In particular, as illustrated in FIG. 54A, the lacing system 10 or any other lacing system disclosed herein can be configured for use with the illustrated in FIG. 54A to at least control the tightness of the shoe around at least the ankle portion of a user's body. As illustrated therein, the embodiment of the lacing system 10 can be used in conjunction with a conventional lacing system.

Figure 54B:
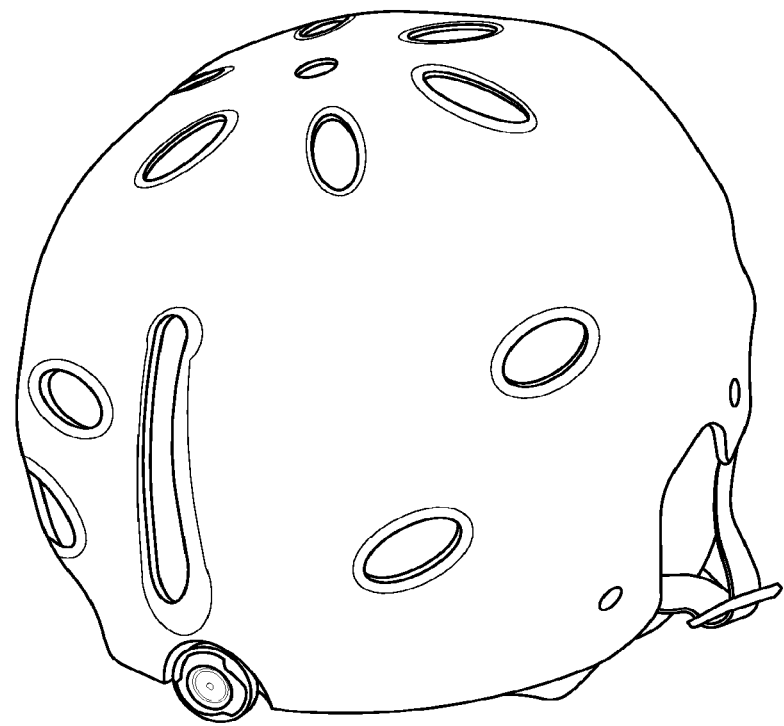

As illustrated in FIG. 54B, the lacing system 10 or any other lacing system disclosed herein can be configured for use with a helmet such as the helmet illustrated in FIG. 54B to at least control the tightness of the strap portion of the helmet.

Figure 54C:
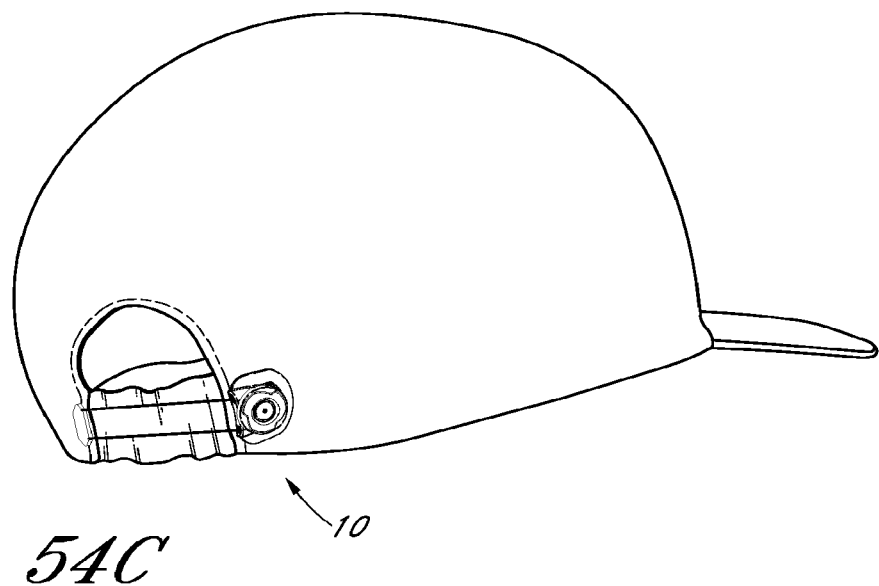

As illustrated in FIG. 54C, the lacing system 10 or any other lacing system disclosed herein can be configured for use with a hat such as the hat illustrated in FIG. 54C to at least control the tightness of the strap portion of the hat.

Figure 54D:
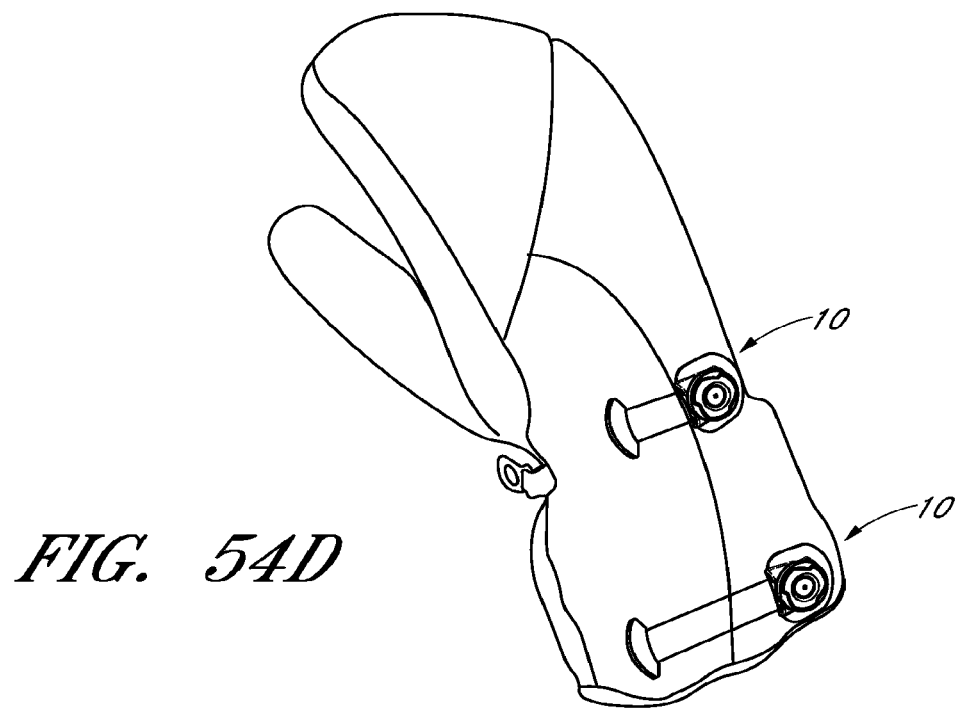

As illustrated in FIG. 54D, the lacing system 10 or any other lacing system disclosed herein can be configured for use with a glove such as the glove illustrated in FIG. 54D to at least control the tightness of the glove around at least the wrist portion of a user's body.

Figure 54E:
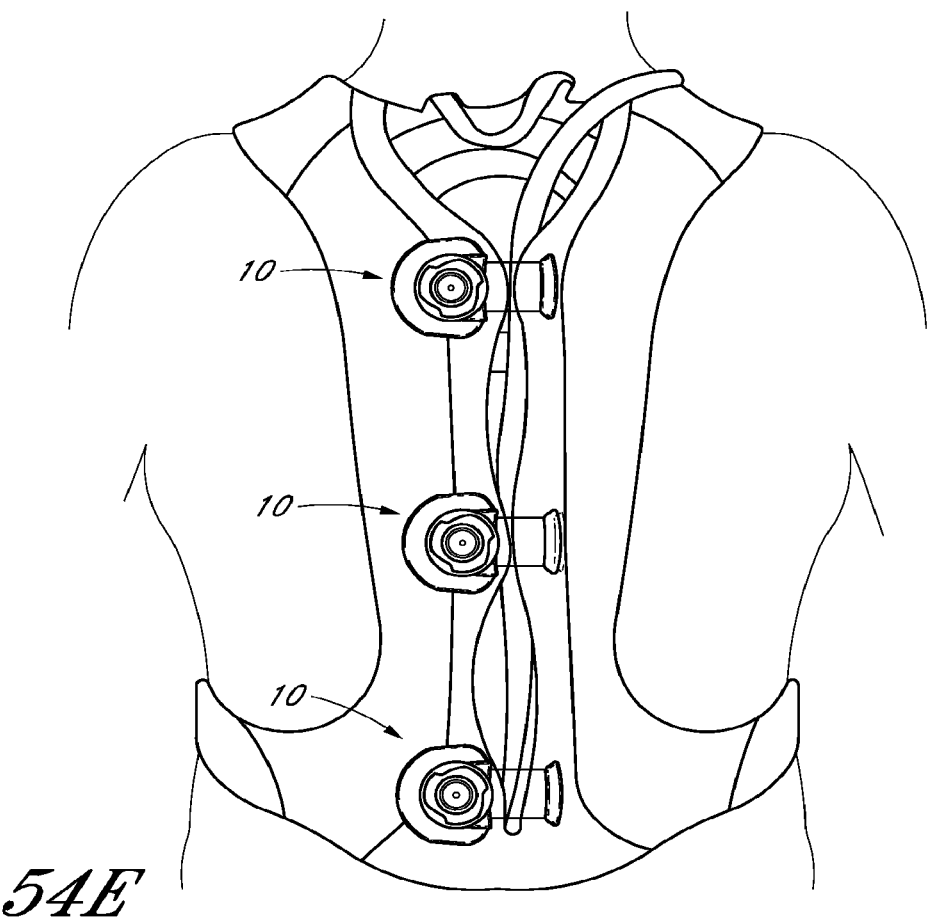

As illustrated in FIG. 54E, the lacing system 10 or any other lacing system disclosed herein can be configured for use with a backpack or a fluid hydration carrier such as the backpack or fluid hydration carrier illustrated in FIG. 54E to at least control the tightness of the backpack or fluid hydration carrier.

Figure 54F:
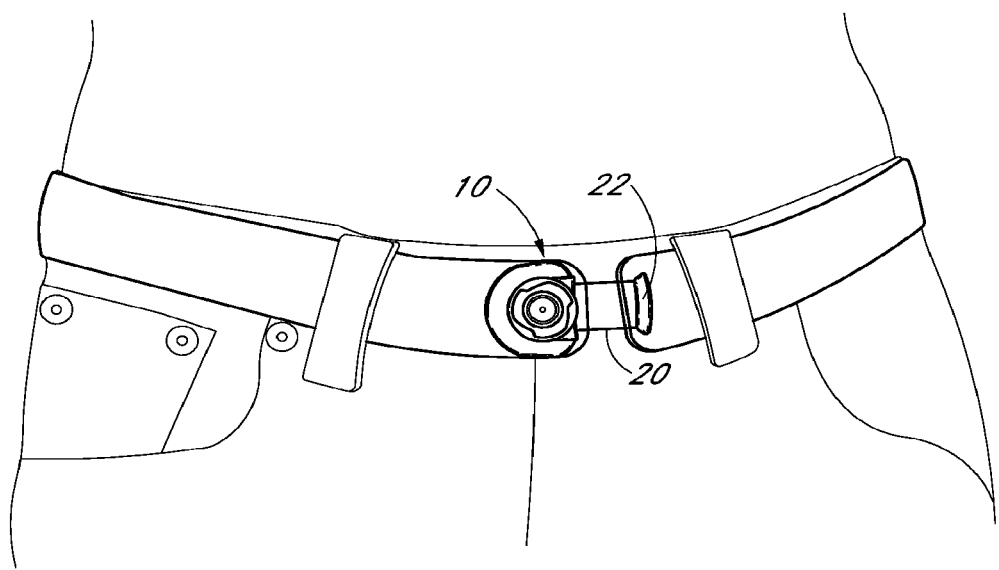

As illustrated in FIG. 54F, the lacing system 10 or any other lacing system disclosed herein can be configured for use with a belt such as the belt illustrated in FIG. 54F to at least control the tightness of the belt around a user's body. In the embodiment of the lacing system 10 illustrated in FIG. 54F, the lacing system 10 can be configured so that the lace 20 is removably supported by the guide member 22.

Figure 54G:
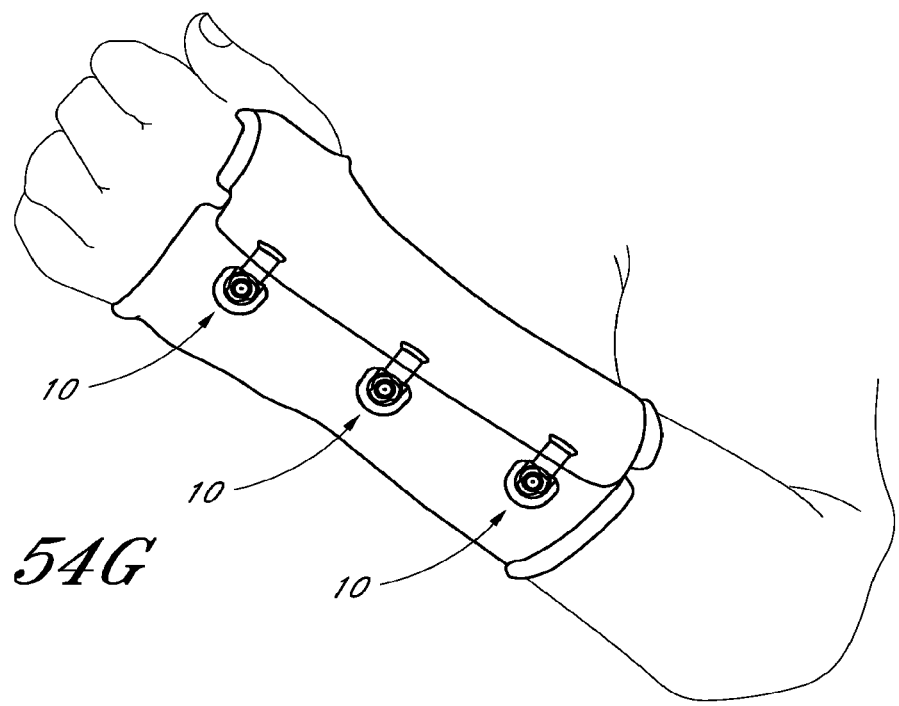

As illustrated in FIG. 54G, the lacing system 10 or any other lacing system disclosed herein can be configured for use with a wrist support, wrist guard, cast, or other suitable objects (hereinafter, collectively referred to as a wrist support) such as the wrist support illustrated in FIG. 54G to at least control the tightness of the wrist support around a portion of the user's arm.

Figure 54H:
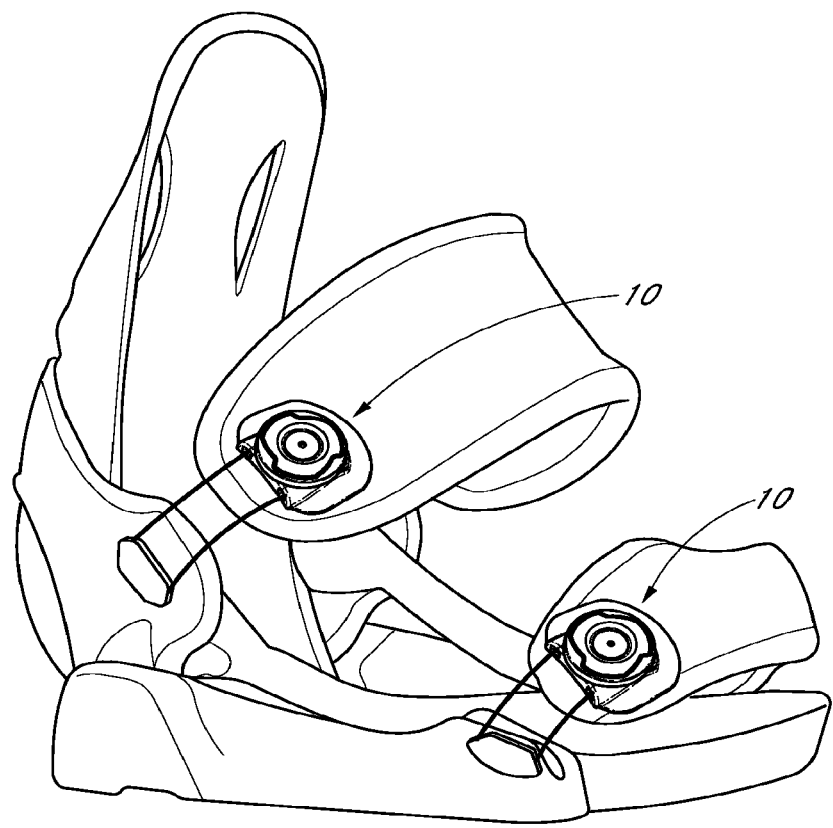

As illustrated in FIG. 54H, the lacing system 10 or any other lacing system disclosed herein can be configured for use with a binding system for snowboarding, water skiing, or any other suitable object such as the binding system illustrated in FIG. 54H to at least control the tightness of the binding system relative to a user's foot.

The components of the lacing systems described herein can be formed from any suitable material such as, but not limited to, plastic, carbon or other fiber reinforced plastic, aluminum, steel, rubber, or any other suitable material or combination of such materials. In some embodiments, the housing, spool, knob, lace guides, or any other suitable components described herein can be injection molded or otherwise formed from any suitable polymeric material, such as nylon, PVC or PET. Some of the components described herein can be formed from a lubricious plastic such as PTFE, or other material as can be determined through routine experimentation, or reducing the friction between a lace and such components is desired. Additionally, some of the components described herein can be coated or layered with a lubricious material to reduce the friction with interacting components or parts.

In some embodiments, the lace or cable (or stop cord disclosed in certain embodiments) can be a highly lubricious cable or fiber having a low modulus of elasticity and a high tensile strength. In some embodiments, the cable can have multiple strands of material woven together. While any suitable lace can be used, some embodiments can utilize a lace formed from extended chain, high modulus polyethylene fibers. One example of a suitable lace material is sold under the trade name SPECTRA™, manufactured by Honeywell of Morris Township, N.J. The extended chain, high modulus polyethylene fibers advantageously have a high strength to weight ratio, are cut resistant, and have very low elasticity. One preferred lace made of this material is tightly woven. The tight weave provides added stiffness to the completed lace. The additional stiffness provided by the weave offers enhanced pushability, such that the lace is easily threaded through the lace guides, and into the reel and spool, or through the guides so as to form a loop of lace that can be easily grasped by a user. Additionally, in some embodiments, the lace can be formed from a molded monofilament polymer. In embodiments that include a stop cord, the stop cord can be made using any of the materials or manners described above in connection with the cable or lace.

The lace or cable can have a diameter of at least about 0.02 inches and/or no more than about 0.04 inches, or at least about 0.025 inches and/or nor more than about 0.035 inches, although diameters outside these ranges can also be used. In some embodiments, the stop cord can have a diameter of within the same ranges as provided for the lace or cable. In some embodiments, the stop cord can have a smaller diameter than the lace. The stop cord can have a diameter of at least about 0.01 inches and/or no more than about 0.03 inches. In some embodiments, the stop cord can have a diameter outside the ranges provided.

Though discussed in terms of footwear, which includes, but is not limited to, ski boots, snow boots, ice skates, horseback riding boots, hiking shoes, running shoes, athletic shoes, specialty shoes, and training shoes, the lacing systems disclosed herein can also provide efficient and effective closure options in a number of various different applications. Such applications can include use in closure or attachment systems on backpacks packs and other similar articles, belts, waistlines and/or cuffs of pants and jackets, neck straps and headbands for helmets, gloves, bindings for water sports, snow sports, and other extreme sports, or in any situation where a system for drawing two objects together can be advantageous.

Although disclosed in the context of certain preferred embodiments and examples, it will be understood by those skilled in the art that the present disclosure extends beyond the specifically disclosed embodiments to other alternative embodiments and/or uses and obvious modifications and equivalents thereof. In addition, while a number of variations have been shown and described in detail, other modifications, which are within the scope of this disclosure, will be readily apparent to those of skill in the art based upon this disclosure. It is also contemplated that various combinations or subcombinations of the specific features and aspects of the embodiments can be made and still fall within the scope of the disclosure. Accordingly, it should be understood that various features and aspects of the disclosed embodiments can be combined with or substituted for one another. Thus, it is intended that the scope of the disclosure should not be limited by the particular disclosed embodiments described above.

What is claimed is:

1. A reel for use with a lacing system for tightening an article comprising:
    a housing having an interior region;
    a spool positioned within the interior region of the housing and rotatable relative thereto;
    a knob rotatable relative to the housing and operably coupled with the spool, the knob being rotatable in a first direction relative to the housing to cause a corresponding incremental rotation of the spool within the interior region of the housing by selective engagement of an arm with a depression, wherein engagement of the arm with the depression substantially impedes the spool from rotating in a second direction within the interior region of the housing, and wherein incremental rotation of the spool in the first direction incrementally winds a tension member about the spool;
    an incremental release mechanism that is operable to allow the spool to incrementally rotate in the second direction within the interior region of the housing by selective disengagement of the arm from the depression, wherein incremental rotation of the spool in the second direction incrementally unwinds the tension member from about the spool; and
    a full release mechanism that is configured upon actuation to fully disengage the arm from the depression to allow the spool to freely rotate in the second direction within the interior region of the housing and thereby enable full unwinding of the tension member from about the spool.

2. The reel of claim 1, wherein the reel is configured so as to not substantially impede rotation of the spool in the first direction within the interior region of the housing.

3. The reel of claim 1, wherein a control effects operation of the incremental release mechanism and the full release mechanism, wherein a first operation of the control causes the incremental release mechanism to selectively disengage the arm from the depression, and wherein a second operation of the control causes the full release mechanism to fully disengage the arm from the depression.

4. The reel of claim 3, wherein the first operation of the control is a movement of the control in a first direction and wherein the second operation of the control is a movement of the control in a second direction that is different than the first direction.

5. The reel of claim 3, wherein the control is the knob.

6. The reel of claim 1, further comprising a rotation limiting component that prevents the spool from being rotated in the second direction after the tension member has been substantially fully loosened.

7. The reel of claim 6, wherein the rotation limiting component comprises a stop cord that is operably coupled with the spool.

8. A mechanism for tightening an article comprising:
a housing having an interior region;
a spool positioned within the interior region of the housing and rotatable relative thereto;
an incremental tightening mechanism that is operably coupled with the spool to cause the spool to incrementally rotate within the interior region of the housing in a first direction by sequential engagement of an arm with a plurality of depressions in a ratchet like manner, wherein incremental rotation of the spool in the first direction incrementally winds a tension member about the spool;
an incremental release mechanism that is operably coupled with the spool to cause the spool to incrementally rotate within the interior region of the housing in a second direction by sequential disengagement of the arm from the plurality of depressions, wherein incremental rotation of the spool in the second direction incrementally unwinds the tension member from about the spool; and
a full release mechanism that is configured upon actuation to enable free rotation of the spool in the second direction by fully disengaging the arm from the plurality of depressions and thereby enable full unwinding of the tension member from about the spool.

9. The mechanism of claim 8, wherein the mechanism is configured so as to not substantially impede rotation of the spool in the first direction within the interior region of the housing; and wherein the mechanism is configured so as to substantially impede the spool from rotating in the second direction within the interior region of the housing except upon actuation of the incremental release mechanism or the full release mechanism.

10. The mechanism of claim 8, wherein a control effects operation of the incremental release mechanism and the full release mechanism, wherein a first operation of the control causes the incremental release mechanism to sequentially disengage the arm from the plurality of depressions and a second operation of the control causes the full release mechanism to fully disengage the arm from the plurality of depressions.

11. The mechanism of claim 10, wherein the control further effects operation of the incremental tightening mechanism, wherein a third operation of the control causes the incremental tightening mechanism to selectively engage the arm and the depression.

12. The mechanism of claim 11, wherein the control is a knob that is operably coupled with the spool.

13. The mechanism of claim 10, wherein the first operation of the control is a movement of the control member in a first direction and the second operation of the control is a movement of the control in a second direction that is different than the first direction.

14. The mechanism of claim 11, wherein the first operation of the control is a movement of the control in a first direction, the second operation of the control is a movement of the control in a second direction that is different than the first direction, and the third operation of the control is a movement of the control in a third direction that is different than the first direction and the second direction.

15. The mechanism of claim 8, further comprising a rotation limiting component that prevents the spool from being rotated in the second direction after the tension member has been substantially fully loosened.

16. A method of winding and unwinding a tension member about a spool of a reel, the reel being used for tightening an article, the method comprising:
accessing a reel comprising:
    a housing having an interior region;
    a spool positioned within the interior region of the housing and rotatable relative thereto;
    a knob rotatable relative to the housing and operably coupled with the spool to cause the spool to rotate within the interior region of the housing;
    an incremental release mechanism; and
    a full release mechanism;
rotating the knob in a first direction relative to the housing to cause a corresponding rotation of the spool within the interior region of the housing and a sequential engagement of an arm with a plurality of depressions in a ratchet like manner to thereby incrementally wind the tension member about the spool;
operating the incremental release mechanism to cause the spool to incrementally rotate in a second direction within the interior region of the housing by sequential disengagement of the arm from the plurality of depressions to thereby incrementally unwind the tension member from about the spool; and
actuating the full release mechanism to fully disengage the arm from the plurality of depressions and thereby enable full unwinding of the tension member from about the spool upon free rotation of the spool in the second direction within the interior region of the housing.

17. The method of claim 16, wherein operating the incremental release mechanism comprises a first operation of a control.

18. The method of claim 17, wherein actuating the full release mechanism comprises a second operation of the control that is different than the first operation.

19. The method of claim 16, wherein the reel further comprises a rotation limiting component that prevents the spool from being rotated in the second direction after the tension member has been substantially fully loosened.

* * * * *